United States Patent [19]
Reyes et al.

[11] Patent Number: 5,885,768
[45] Date of Patent: Mar. 23, 1999

[54] HEPATITIS E VIRUS PEPTIDE ANTIGEN AND ANTIBODIES

[75] Inventors: Gregory R. Reyes, Palo Alto, Calif.; Daniel W. Bradley, Lawrenceville, Ga.; Albert W. Tam, San Francisco, Calif.; Mitchell Carl, Silver Spring, Md.

[73] Assignee: The United States of America as Represented by the Department of Health and Human Services, Washington, D.C.

[21] Appl. No.: 876,941

[22] Filed: May 1, 1992

Related U.S. Application Data

[63] Continuation-in-part of Ser. No. 822,335, Jan. 17, 1992, abandoned, which is a continuation-in-part of Ser. No. 681,078, Apr. 5, 1991, abandoned, which is a continuation-in-part of Ser. No. 505,888, Apr. 5, 1990, abandoned, which is a continuation-in-part of Ser. No. 420,921, Oct. 13, 1989, abandoned, which is a continuation-in-part of Ser. No. 367,486, Jun. 16, 1989, abandoned, which is a continuation-in-part of Ser. No. 336,672, Apr. 11, 1989, abandoned, which is a continuation-in-part of Ser. No. 208,997, Jun. 17, 1988, abandoned.

[51] Int. Cl.$^6$ .............................. C12Q 1/70; C07K 7/08; C07K 14/08

[52] U.S. Cl. ............................. 435/5; 530/324; 530/326; 530/327; 530/403; 424/189.1

[58] Field of Search ............................. 424/189.1, 228.1; 530/327, 326, 325, 324, 403; 435/5; 930/223

[56] References Cited

PUBLICATIONS

Tam et al, *Virology*, 185:120–131 (1991).
Huang et al, *Virology*, :1 –9 (1992).
Bradley et al, *Proc. Natl. Acad. Sci. USA*, 84:6277–6281 (1987).
Purdy et al, *Arch Virol*, 123:335–349 (1992).
Yarbough et al, *J. Virology*, 65:5790–5797 (1991).
Reyes et al, *Reports*, :1335–1339 (1990).

*Primary Examiner*—Mary E. Mosher
*Attorney, Agent, or Firm*—Charles K. Sholtz; Gary R. Fabian; Peter J. Dehlinger

[57] ABSTRACT

Immunogenic peptides derived from the ORF1, ORF2, and ORF3 regions of hepatitis E virus (HEV), diagnostic reagents containing the peptide antigens, vaccine compositions containing the antigens, and antibodies which are immunoreactive with the antigens are disclosed.

8 Claims, 13 Drawing Sheets

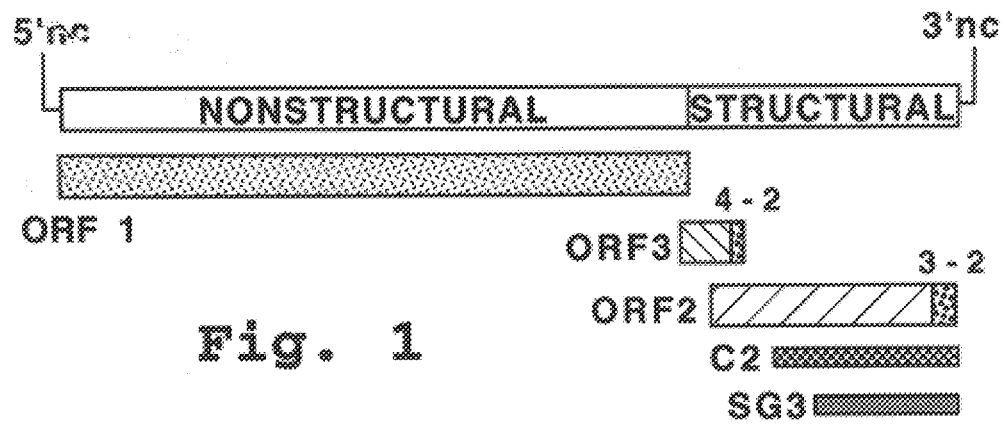
Fig. 1
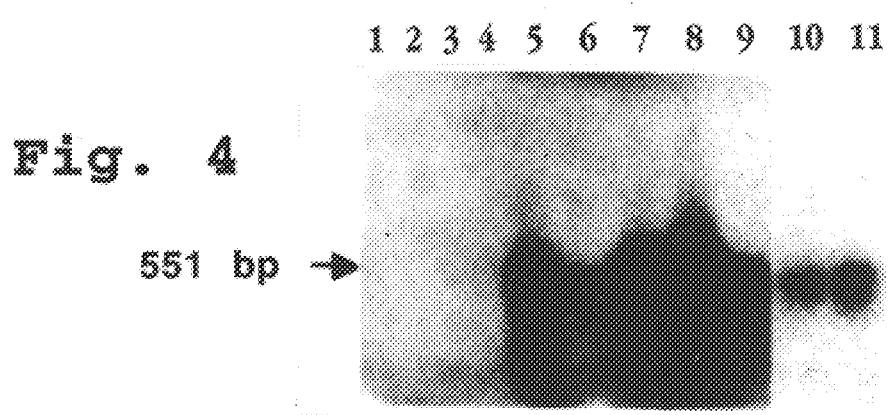
Fig. 4
551 bp →
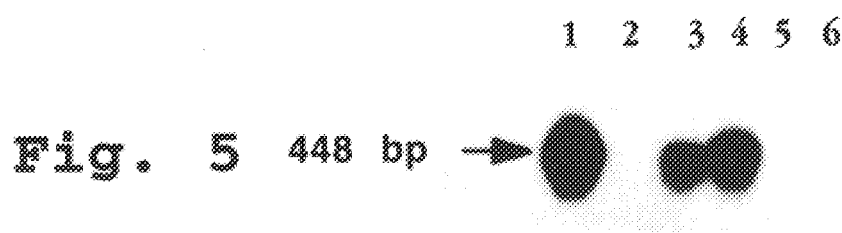
Fig. 5    448 bp →
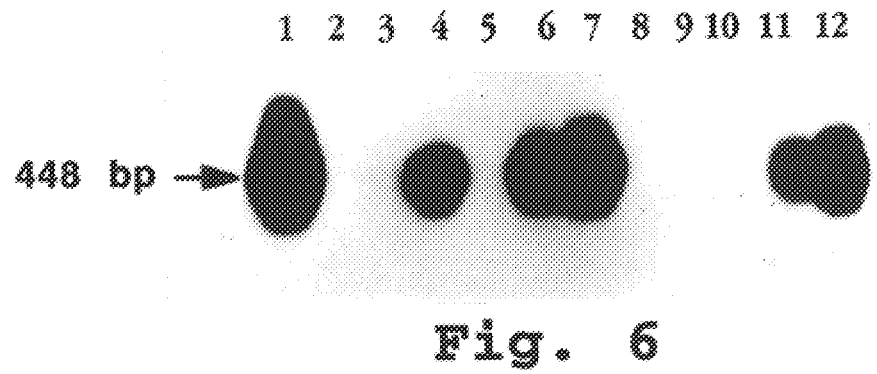
448 bp →
Fig. 6

↓--ORF3-->                                              ↓--ORF2-->

```
      5110v      5120v      5130v      5140v      5150v      5160v
TGGAATGAATAACATGTCTTTTGCTGCGCCCATGGGTTCGCGACCATGCGCCCTCGGCCT
  GAATGAATAACATGT   TTTGCTGCGCCCATGGGTTCGC ACCATGCGCCCT GGCCT
CTGAATGAATAACATGTGGTTTGCTGCGCCCATGGGTTCGCCACCATGCGCCCTAGGCCT 5170v      5180v      5190v      5200v      5210v      5220v
ATTTTGTTGCTGCTCCTCATGTTTTTGCCTATGCTGCCCGCGCCACCGCCCGGTCAGCCG
  TTTTG TG  TG  TCCTC TGTTT TGCCTATG TGCCCGCGCCACCG CCGGTCAGCCG
CTTTTGCTGTTGTTCCTCTTGTTTCTGCCTATGTTGCCCGCGCCACCGACCGGTCAGCCG 5230v      5240v      5250v      5260v      5270v      5280v
TCTGGCCGCCGTCGTGGGCGGCGCAGCGGCGGTTCCGGCGGTGGTTTCTGGGGTGACCGG
TCTGGCCGCCGTCGTGGGCGGCGCAGCGGCGGT CCGGCGGTGGTTTCTGGGGTGACCGG
TCTGGCCGCCGTCGTGGGCGGCGCAGCGGCGGTACCGGCGGTGGTTTCTGGGGTGACCGG 5290v      5300v      5310v      5320v      5330v      5340v
GTTGATTCTCAGCCCTTCGCAATCCCCTATATTCATCCAACCAACCCCTTCGCCCCCGAT
GTTGATTCTCAGCCCTTCGCAATCCCCTATATTCATCCAACCAACCCCTT GCCCC GA
GTTGATTCTCAGCCCTTCGCAATCCCCTATATTCATCCAACCAACCCCTTTGCCCCAGAC
```

↓--406.4-2-->

```
      5350v      5360v      5370v      5380v      5390v      5400v
GTCACCGCTGCGGCCGGGGCTGGACCTCGTGTTCGCCAACCCGCCCGACCACTCGGCTCC
GT  CCGCTGCG CCGGG CTGGACCTCG TTCGCCAACC GCCCG CCACT GGCTCC
GTTGCCGCTGCGTCCGGGTCTGGACCTCGCCTTCGCCAACCAGCCCGGCCACTTGGCTCC 5410v      5420v      5430v      5440v      5450v      5460v
GCTTGGCGTGACCAGGCCCAGCGCCCCGCCGTTGCCTCACGTCGTAGACCTACCACAGCT
 CTTGGCG GA CAGGCCCAGCGCCCC CCG TGCCTC CGTCG  GACCT CCACAGC
ACTTGGCGAGATCAGGCCCAGCGCCCCTCCGCTGCCTCCCGTCGCCGACCTGCCACAGCC
```

<--406.4-2--|
  <--ORF3-↓

```
      5470v      5480v      5490v      5500v      5510v      5520v
GGGGCCGCGCCGCTAACCGCGGTCGCTCCGGCCCATGACACCCCGCCAGTGCCTGATGTC
GGGGC GCG CGCT AC GC GT GC CC GCCCATGACACC C CC GT CC GA GT
GGGGCTGCGGCGCTGACGGCTGTGGCGCCTGCCCATGACACCTCACCCGTCCCGGACGTT 5530v      5540v      5550v      5560v      5570v      5580v
GACTCCCGCGGCGCCATCTTGCGCCGGCAGTATAACCTATCAACATCTCCCCTTACCTCT
GA TC CGCGG GC AT  T CGCCG CAGTATAA  T TC AC TC CCCCT AC TC
GATTCTCGCGGTGCAATTCTACGCCGCCAGTATAATTTGTCTACTTCACCCCTGACATCC
```

Fig. 7A

```
       5590v      5600v      5610v      5620v      5630v      5640v
TCCGTGGCCACCGGCACTAACCTGGTTCTTTATGCCGCCCCTCTTAGTCCGCTTTTACCC
TC GTGGCC C GGCACTAA  T GT CT TATGC GCCCC CTTA TCCGC T T CC
TCTGTGGCCTCTGGCACTAATTTAGTCCTGTATGCAGCCCCCCTTAATCCGCCTCTGCCG 5650v      5660v      5670v      5680v      5690v      5700v
CTTCAGGACGGCACCAATACCCATATAATGGCCACGGAAGCTTCTAATTATGCCCAGTAC
CT CAGGACGG AC AATAC CA AT ATGGCCAC GA GC TC AATTATGC CAGTAC
CTGCAGGACGGTACTAATACTCACATTATGGCCACAGAGGCCTCCAATTATGCACAGTAC 5710v      5720v      5730v      5740v      5750v      5760v
CGGGTTGCCCGTGCCACAATCCGTTACCGCCCGCTGGTCCCCAATGCTGTCGGCGGTTAC
CGGGTTGCCCG GC AC ATCCGTTACCG CC CT GT CC AATGC GT GG GG TA
CGGGTTGCCCGCGCTACTATCCGTTACCGGCCCCTAGTGCCTAATGCAGTTGGAGGCTAT (C2) ↓→

5770v      5780v      5790v      5800v      5810v      5820v
GCCATCTCCATCTCATTCTGGCCACAGACCACCACCACCCCGACGTCCGTTGATATGAAT
GC AT TCCAT TC TTCTGGCC CA AC ACCAC ACCCC AC TC GTTGA ATGAAT
GCTATATCCATTTCTTTCTGGCCTCAAACAACCACAACCCCTACATCTGTTGACATGAAT 5830v      5840v      5850v      5860v      5870v      5880v
TCAATAACCTCGACGGATGTTCGTATTTTAGTCCAGCCCGGCATAGCCTCTGAGCTTGTG
TC AT AC TC AC GATGT  G ATT T GT CA CC GGCATAGC TCTGA  T GT
TCCATTACTTCCACTGATGTCAGGATTCTTGTTCAACCTGGCATAGCATCTGAATTGGTC 5890v      5900v      5910v      5920v      5930v      5940v
ATCCCAAGTGAGCGCCTACACTATCGTAACCAAGGCTGGCGCTCCGTCGAGACCTCTGGG
ATCCCAAG GAGCGCCT CACTA CG AA CAAGG TGGCGCTC GT GAGAC TCTGG
ATCCCAAGCGAGCGCCTTCACTACCGCAATCAAGGTTGGCGCTCGGTTGAGACATCTGGT 5950v      5960v      5970v      5980v      5990v      6000v
GTGGCTGAGGAGGAGGCTACCTCTGGTCTTGTTATGCTTTGCATACATGGCTCACTCGTA
GT GCTGAGGAGGA GC ACCTC GGTCTTGT ATG T TGCATACATGGCTC C  GT
GTTGCTGAGGAGGAAGCCACCTCCGGTCTTGTCATGTTATGCATACATGGCTCTCCAGTT 6010v      6020v      6030v      6040v      6050v      6060v
AATTCCTATACTAATACACCCTATACCGGTGCCCTCGGGCTGTTGGACTTTGCCCTTGAG
AA TCCTATAC AATAC CC TATACCGGTGCCCT GG  T TGGACTTTGCC T GAG
AACTCCTATACCAATACCCCTTATACCGGTGCCCTTGGCTTACTGGACTTTGCCTTAGAG 6070v      6080v      6090v      6100v      6110v      6120v
CTTGAGTTTCGCAACCTTACCCCCGGTAACACCAATACGCGGGTCTCCCGTTATTCCAGC
CTTGAGTTTCGCAA CT ACC CC GTAACACCAATAC CG GT TCCCGTTA TCCAGC
CTTGAGTTTCGCAATCTCACCACCTGTAACACCAATACACGTGTGTCCCGTTACTCCAGC
```

```
         6130v       6140v       6150v       6160v       6170v       6180v
ACTGCTCGCCACCGCCTTCGTCGCGGTGCGGACGGGACTGCCGAGCTCACCACCACGGCT
ACTGCTCG CAC  C    CG   G G        GACGGGACTGC GAGCT ACCAC AC GC
ACTGCTCGTCACTCCGCCCGAGGGGCC---GACGGGACTGCGGAGCTGACCACAACTGCA 6190v       6200v       6210v       6220v       6230v       6240v
GCTACCCGCTTTATGAAGGACCTCTATTTTACTAGTACTAATGGTGTCGGTGAGATCGGC
GC ACC  G TT ATGAA GA CTC A TTTAC  G    TAATGG GT GGTGA TCGGC
GCCACCAGGTTCATGAAAGATCTCCACTTTACCGGCCTTAATGGGGTAGGTGAAGTCGGC 6250v       6260v       6270v       6280v       6290v       6300v
CGCGGGATAGCCCTCACCCTGTTCAACCTTGCTGACACTCTGCTTGGCGGCCTGCCGACA
CGCGGGATAGC CT AC  T  T AACCTTGCTGACAC CT CT GGCGG CT CCGACA
CGCGGGATAGCTCTAACATTACTTAACCTTGCTGACACGCTCCTCGGCGGGCTCCCGACA 6310v       6320v       6330v       6340v       6350v       6360v
GAATTGATTTCGTCGGCTGGTGGCCAGCTGTTCTACTCCCGTCCCGTTGTCTCAGCCAAT
GAATT  ATTTCGTCGGCTGG GG CA CTGTT  TA TCCCG CC GTTGTCTCAGCCAAT
GAATTAATTTCGTCGGCTGGCGGGCAACTGTTTTATTCCCGCCCGGTTGTCTCAGCCAAT 6370v       6380v       6390v       6400v       6410v       6420v
GGCGAGCCGACTGTTAAGTTGTATACATCTGTAGAGAATGCTCAGCAGGATAAGGGTATT
GGCGAGCC AC GT AAG T TATACATC GT GAGAATGCTCAGCAGGATAAGGGT TT
GGCGAGCCAACCGTGAAGCTCTATACATCAGTGGAGAATGCTCAGCAGGATAAGGGTGTT 6430v       6440v       6450v       6460v       6470v       6480v
GCAATCCCGCATGACATTGACCTCGGAGAATCTCGTGTGGTTATTCAGGATTATGATAAC
GC ATCCC CA GA AT GA CT GG GA TC CGTGTGGT ATTCAGGATTATGA AAC
GCTATCCCCACGATATCGATCTTGGTGATTCGCGTGTGGTCATTCAGGATTATGACAAC 6490v       6500v       6510v       6520v       6530v       6540v
CAACATGAACAAGATCGGCCGACGCCTTCTCCAGCCCCATCGCGCCCTTTCTCTGTCCTT
CA CATGA CA GATCGGCC AC CC TC CC GC CCATC CG CCTTT TCTGT CT
CAGCATGAGCAGGATCGGCCCACCCCGTCGCCTGCGCCATCTCGGCCTTTTTCTGTTCTC 6550v       6560v       6570v       6580v       6590v       6600v
CGAGCTAATGATGTGCTTTGGCTCTCTCTCACCGCTGCCGAGTATGACCAGTCCACTTAT
CGAGC AATGATGT CTTTGGCT TC CTCAC GC GCCGAGTATGACCAGTCCACTTA
CGAGCAAATGATGTACTTTGGCTGTCCCTCACTGCAGCCGAGTATGACCAGTCCACTTAC 6610v       6620v       6630v       6640v       6650v       6660v
GGCTCTTCGACTGGCCCAGTTTATGTTTCTGACTCTGTGACCTTGGTTAATGTTGCGACC
GG TC TC ACTGGCCC GTTTAT T TC GAC   GTGAC TTGGT AATGTTGCGAC
GGGTCGTCAACTGGCCCGGTTTATATCTCGGACAGCGTGACTTTGGTGAATGTTGCGACT 6670v       6680v       6690v       6700v       6710v       6720v
GGCGCGCAGGCCGTTGCCCGGTCGCTCGATTGGACCAAGGTCACACTTGACGGTCGCCCC
GGCGCGCAGGCCGT  GCCCG TCGCT GA TGG CCAA GTCAC CT GACGG CG CCC
GGCGCGCAGGCCGTAGCCCGATCGCTTGACTGGTCCAAAGTCACCCTCGACGGGCGGCCC
```

Fig. 7C

```
       6730v      6740v      6750v      6760v      6770v      6780v
CTCTCCACCATCCAGCAGTACTCGAAGACCTTCTTTGTCCTGCCGCTCCGCGGTAAGCTC
CTC C AC  T   AGCA TA TC AAGAC TTCTTTGT CT CC CT CG GG AAGCTC
CTCCCGACTGTTGAGCAATATTCCAAGACATTCTTTGTGCTCCCCCTTCGTGGCAAGCTC 6790v      6800v      6810v      6820v      6830v      6840v
TCTTTCTGGGAGGCAGGCACAACTAAAGCCGGGTACCCTTATAATTATAACACCACTGCT
TC TT TGGGAGGC GGCACAAC AAAGC GG TA CCTTATAATTATAA AC ACTGCT
TCCTTTTGGGAGGCCGGCACAACAAAAGCAGGTTATCCTTATAATTATAATACTACTGCT 6850v      6860v      6870v      6880v      6890v      6900v
AGCGACCAACTGCTTGTCGAGAATGCCGCCGGGCACCGGGTCGCTATTTCCACTTACACC
AG GACCA   T CT  T GA AATGC GCCGG CA CGGGTCGC ATTTC AC TA ACC
AGTGACCAGATTCTGATTGAAAATGCTGCCGGCCATCGGGTCGCCATTTCAACCTATACC 6910v      6920v      6930v      6940v      6950v      6960v
ACTAGCCTGGGTGCTGGTCCCGTCTCCATTTCTGCGGTTGCCGTTTTAGCCCCCCACTCT
AC AG CT GG GC GGTCC GTC CCATTTCTGCGG  GC GTTTT GC CC C CTC
ACCAGGCTTGGGGCCGGTCCGGTCGCCATTTCTGCGGCCGCGGTTTTGGCTCCACGCTCC

↓--406.3-2-->
       6970v      6980v      6990v      7000v      7010v      7020v
GCGCTAGCATTGCTTGAGGATACCTTGGACTACCCTGCCCGCGCCCATACTTTTGATGAT
GC CT GC  TGCT GAGGATAC TT GA TA CC G  CG GC CA AC TTTGATGA
GCCCTGGCTCTGCTGGAGGATACTTTTGATTATCCGGGGCGGGCGCACACATTTGATGAC 7030v      7040v      7050v      7060v      7070v      7080v
TTCTGCCCAGAGTGCCGCCCCCTTGGCCTTCAGGGCTGCGCTTTCCAGTCTACTGTCGCT
TTCTGCCC GA TGCCGC C  T GGCCT CAGGG TG GCTTTCCAGTC ACTGTCGCT
TTCTGCCCTGAATGCCGCGCTTTAGGCCTCCAGGGTTGTGCTTTCCAGTCAACTGTCGCT

<--SG3
                                              <--406.3-2
                                                 <--C2
       7090v      7100v      7110v      7120v      7130v      7140v
GAGCTTCAGCGCCTTAAGATGAAGGTGGGTAAAACTCGGGAGTTGTAGTTTATTTGCTTG
GAGCT CAGCGCCTTAA  T AAGGTGGGTAAAACTCGGGAGTTGTAGTTTATTTG  TG
GAGCTCCAGCGCCTTAAAGTTAAGGTGGGTAAAACTCGGGAGTTGTAGTTTATTTGGCTG 7150v      7160v                 7170v      7180v      7190v
TGCCCCCTTCTTTCTGTTGC---------TTATTTCTCATTTCTGCGTTCCGCGCTCCC
TGCCC CCT CTT       TGC         TTATTTC   TTTCT GT CCGCGCTCCC
TGCCCACCTACTTATATCTGCTGATTTCCTTTATTTCCTTTTTCTCGGTCCCGCGCTCCC

<-I ORF2 v 7195
TGA
TGA
TGA
```

Fig. 7D

```
         10        20        30        40        50        60
MNNMSFAAPMGSRPCALGLFCCCSSCFCLCCPRHRPVSRLAAVVGGAAAVPAVVSGVTGL
X:::   :::::::.:::::::::::::::::::::::::::::::::::::::::::::
MNNMWFAAPMGSPPCALGLFCCCSSCFCLCCPRHRPVSRLAAVVGGAAAVPAVVSGVTGL
         10        20        30        40        50        60

↓406.4-2-->
              406.4-2
         70        80        90       100       110       120
ILSPSQSPIFIQPTPSPPMSPLRPGLDLVFANPPDHSAPLGVTRPSAPPLPHVVDLPQLG
:::::::::::::::: :.  ::::::::.:::..:  ::::  .::::::::.:.:::  :
ILSPSQSPIFIQPTPLPQTLPLRPGLDLAFANQPGHLAPLGEIRPSAPPLPPVADLPQPG
         70        80        90       100       110       120
<--↓406.4-2
PRRZ
 ::X
LRRZ
```

Fig. 8

```
          10        20        30        40        50        60
MRPRPILLLLLMFLPMLPAPPPGQPSGRRRGRRSGGSGGGFWGDRVDSQPFAIPYIHPTN
X:::::.:::.:.:::::::::::::::::::.::::::::::::::::::::::::::
MRPRPLLLLFLLFLPMLPAPPTGQPSGRRRGRRSGGTGGGFWGDRVDSQPFAIPYIHPTN
          10        20        30        40        50        60

70        80        90       100       110       120
PFAPDVTAAAGAGPRVRQPARPLGSAWRDQAQRPAVASRRRPTTAGAAPLTAVAPAHDTP
:::::::..::..:::.:::::::::::.:::::::::..::::::.:::::::::::.
PFAPDVAAASGSGPRLRQPARPLGSTWRDQAQRPSAASRRRPATAGAAALTAVAPAHDTS
          70        80        90       100       110       120

130       140       150       160       170       180
PVPDVDSRGAILRRQYNLSTSPLTSSVATGTNLVLYAAPLSPLLPLQDGTNTHIMATEAS
::::::::::::::::::::::::::::.::::::::::::.::::::::::::::::::
PVPDVDSRGAILRRQYNLSTSPLTSSVASGTNLVLYAAPLNPPLPLQDGTNTHIMATEAS
         130       140       150       160       170       180

↓ C-2-->
         190       200       210       220  ↓ 230       240
NYAQYRVARATIRYRPLVPNAVGGYAISISFWPQTTTTPTSVDMNSITSTDVRILVQPGI
::::::::::::::::::::::::::::::::::::::::::::::::::::::::::::
NYAQYRVARATIRYRPLVPNAVGGYAISISFWPQTTTTPTSVDMNSITSTDVRILVQPGI
         190       200       210       220       230       240

250       260       270       280       290       300
ASELVIPSERLHYRNQGWRSVETSGVAEEEATSGLVMLCIHGSLVNSYTNTPYTGALGLL
:::::::::::::::::::::::::::::::::::::::::::: :::::::::::::::
ASELVIPSERLHYRNQGWRSVETSGVAEEEATSGLVMLCIHGSPVNSYTNTPYTGALGLL
         250       260       270       280       290       300

↓ SG3-->
         310       320       330  ↓ 340       350       360
DFALELEFRNLTPGNTNTRVSRYSSTARHRLRRGADGTAELTTTAATRFMKDLYFTSTNG
:::::::::::.. ::::::::::::::::.  :::::::::::::::::::::.:: ::
DFALELEFRNLTTCNTNTRVSRYSSTARHS-ARGADGTAELTTTAATRFMKDLHFTGLNG
         310       320       330       340       350

370       380       390       400       410       420
VGEIGRGIALTLFNLADTLLGGLPTELISSAGGQLFYSRPVVSANGEPTVKLYTSVENAQ
:::.:::::::::.::::::::::::::::::::::::::::::::::::::::::::::
VGEVGRGIALTLLNLADTLLGGLPTELISSAGGQLFYSRPVVSANGEPTVKLYTSVENAQ
360      370       380       390       400       410

430       440       450       460       470       480
QDKGIAIPHDIDLGESRVVIQDYDNQHEQDRPTPSPAPSRPFSVLRANDVLWLSLTAAEY
::::.:::::::::::.:::::::::::::::::::::::::::::::::::::::::::
QDKGVAIPHDIDLGDSRVVIQDYDNQHEQDRPTPSPAPSRPFSVLRANDVLWLSLTAAEY
420      430       440       450       460       470
```

Fig. 9A

```
          490       500       510       520       530       540
DQSTYGSSTGPVYVSDSVTLVNVATGAQAVARSLDWTKVTLDGRPLSTIQQYSKTFFVLP
::::::::::::::::.:::::::::::::::::::::::::.::::::::::.::::::::::
DQSTYGSSTGPVYISDSVTLVNVATGAQAVARSLDWSKVTLDGRPLPTVEQYSKTFFVLP
    480       490       500       510       520       530

550       560       570       580       590       600
LRGKLSFWEAGTTKAGYPYNYNTTASDQLLVENAAGHRVAISTYTTSLGAGPVSISAVAV
::::::::::::::::::::::::::::::.::::::::::::::::::::::.::::::.::
LRGKLSFWEAGTTKAGYPYNYNTTASDQILIENAAGHRVAISTYTTRLGAGPVAISAAAV
    540       550       560       570       580       590

<--SG3
              ↓ 406.3-2-->                              <--406.3-2
         610  ▼     620       630       640       650   <--C2  ↓

LAPHSALALLEDTLDYPARAHTFDDFCPECRPLGLQGCAFQSTVAELQRLKMKVGKTRELZ
::::.:::::::::::.:::::.::::::::::::::::::::::::::::::.:::::::::
LAPRSALALLEDTFDYPGRAHTFDDFCPECRALGLQGCAFQSTVAELQRLKVKVGKTRELZ
    600       610       620       630       640       650
```

Fig. 9B

| PEPTIDE | AMINO ACIDS POSITION | SEQUENCE | SEQ ID NO. |
|---|---|---|---|
| ORF1 | | | |
| 1 | 169-182 | MSPSDVAEAMFRHG | 23 |
| 2 | 221-234 | YEGDTSAGYNHDVS | 24 |
| 3 | 461-474 | TAIRKALSKFCCFM | 25 |
| 4 | 597-618 | SQSTMAAGPFSLTYAASAAGLE | 26 |
| 5 | 901-914 | AWERNHRPGDELYL | 27 |
| 6 | 1185-1198 | DAPGLLREVGISDA | 28 |
| 7 | 1205-1222 | LAGGEIGHQRPSVIPRGN | 29 |
| 8 | 1237-1254 | CQISAFHQLAEELGHRPV | 30 |
| 9 | 1285-1362 | TFELTDIVHCRMAAPSQRKAVLST-LVGRYGGRTKLYNASHSDVRDSLA-RFIPAIGPVQVTTCELYELVEAMVE-KGQDG | 31 |
| 10 | 1377-1410 | RITFFQKDCNKFTTGETIAHGKVGQ-GISAWSKTF | 32 |
| 11 | 1429-1446 | IEKAILALLPQGVFYGDAFDDTVFSA | 33 |
| 12 | 1505-1518 | PKESLRGFWKKHSG | 34 |
| ORF2 | | | |
| 1 | 25-38 | PSGRRRGRRSGGSG | 35 |
| 2 | 341-354 | LTTTAATRFMKDLY | 36 |
| 3 | 517-530 | TKVTLDGRPLSTIQ | 37 |
| ORF3 | | | |
| 1 | 105-122 | PSAPPLPHVVDLPQLGPR | 38 |

Fig. 11

SEQUENCE LISTING ( 1 ) GENERAL INFORMATION:

( i i i ) NUMBER OF SEQUENCES: 76

( 2 ) INFORMATION FOR SEQ ID NO:1:

( i ) SEQUENCE CHARACTERISTICS:
        ( A ) LENGTH: 2094 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: BURMA SEQUENCE, FIGURE 7

( x i ) SEQUENCE DESCRIPTION: SEQ ID NO:1:

```
TGGAATGAAT  AACATGTCTT  TTGCTGCGCC  CATGGGTTCG  CGACCATGCG  CCCTCGGCCT      60

ATTTTGTTGC  TGCTCCTCAT  GTTTTTGCCT  ATGCTGCCCG  CGCCACCGCC  CGGTCAGCCG     120

TCTGGCCGCC  GTCGTGGGCG  GCGCAGCGGC  GGTTCCGGCG  GTGGTTTCTG  GGGTGACCGG     180

GTTGATTCTC  AGCCCTTCGC  AATCCCCTAT  ATTCATCCAA  CCAACCCCTT  CGCCCCCGAT     240

GTCACCGCTG  CGGCCGGGGC  TGGACCTCGT  GTTCGCCAAC  CCGCCCGACC  ACTCGGCTCC     300

GCTTGGCGTG  ACCAGGCCCA  GCGCCCCGCC  GTTGCCTCAC  GTCGTAGACC  TACCACAGCT     360

GGGGCCGCGC  CGCTAACCGC  GGTCGCTCCG  GCCCATGACA  CCCCGCCAGT  GCCTGATGTC     420

GACTCCCGCG  GCGCCATCTT  GCGCCGGCAG  TATAACCTAT  CAACATCTCC  CCTTACCTCT     480

TCCGTGGCCA  CCGGCACTAA  CCTGGTTCTT  TATGCCGCCC  CTCTTAGTCC  GCTTTTACCC     540

CTTCAGGACG  GCACCAATAC  CCATATAATG  GCCACGGAAG  CTTCTAATTA  TGCCCAGTAC     600
```

```
CGGGTTGCCC  GTGCCACAAT  CCGTTACCGC  CCGCTGGTCC  CCAATGCTGT  CGGCGGTTAC        660

GCCATCTCCA  TCTCATTCTG  GCCACAGACC  ACCACCACCC  CGACGTCCGT  TGATATGAAT        720

TCAATAACCT  CGACGGATGT  TCGTATTTTA  GTCCAGCCCG  GCATAGCCTC  TGAGCTTGTG        780

ATCCCAAGTG  AGCGCCTACA  CTATCGTAAC  CAAGGCTGGC  GCTCCGTCGA  GACCTCTGGG        840

GTGGCTGAGG  AGGAGGCTAC  CTCTGGTCTT  GTTATGCTTT  GCATACATGG  CTCACTCGTA        900

AATTCCTATA  CTAATACACC  CTATACCGGT  GCCCTCGGGC  TGTTGGACTT  TGCCCTTGAG        960

CTTGAGTTTC  GCAACCTTAC  CCCCGGTAAC  ACCAATACGC  GGGTCTCCCG  TTATTCCAGC       1020

ACTGCTCGCC  ACCGCCTTCG  TCGCGGTGCG  GACGGGACTG  CCGAGCTCAC  CACCACGGCT       1080

GCTACCCGCT  TTATGAAGGA  CCTCTATTTT  ACTAGTACTA  ATGGTGTCGG  TGAGATCGGC       1140

CGCGGGATAG  CCCTCACCCT  GTTCAACCTT  GCTGACACTC  TGCTTGGCGG  CCTGCCGACA       1200

GAATTGATTT  CGTCGGCTGG  TGGCCAGCTG  TTCTACTCCC  GTCCGTTGT  CTCAGCCAAT       1260

GGCGAGCCGA  CTGTTAAGTT  GTATACATCT  GTAGAGAATG  CTCAGCAGGA  TAAGGGTATT       1320

GCAATCCCGC  ATGACATTGA  CCTCGGAGAA  TCTCGTGTGG  TTATTCAGGA  TTATGATAAC       1380

CAACATGAAC  AAGATCGGCC  GACGCCTTCT  CCAGCCCCAT  CGCGCCCTTT  CTCTGTCCTT       1440

CGAGCTAATG  ATGTGCTTTG  GCTCTCTCTC  ACCGCTGCCG  AGTATGACCA  GTCCACTTAT       1500

GGCTCTTCGA  CTGGCCCAGT  TTATGTTTCT  GACTCTGTGA  CCTTGGTTAA  TGTTGCGACC       1560

GGCGCGCAGG  CCGTTGCCCG  GTCGCTCGAT  TGGACCAAGG  TCACACTTGA  CGGTCGCCCC       1620

CTCTCCACCA  TCCAGCAGTA  CTCGAAGACC  TTCTTTGTCC  TGCCGCTCCG  CGGTAAGCTC       1680

TCTTTCTGGG  AGGCAGGCAC  AACTAAAGCC  GGGTACCCTT  ATAATTATAA  CACCACTGCT       1740

AGCGACCAAC  TGCTTGTCGA  GAATGCCGCC  GGGCACCGGG  TCGCTATTTC  CACTTACACC       1800

ACTAGCCTGG  GTGCTGGTCC  CGTCTCCATT  TCTGCGGTTG  CCGTTTTAGC  CCCCCACTCT       1860

GCGCTAGCAT  TGCTTGAGGA  TACCTTGGAC  TACCCTGCCC  GCGCCCATAC  TTTTGATGAT       1920

TTCTGCCCAG  AGTGCCGCCC  CCTTGGCCTT  CAGGGCTGCG  CTTTCCAGTC  TACTGTCGCT       1980

GAGCTTCAGC  GCCTTAAGAT  GAAGGTGGGT  AAAACTCGGG  AGTTGTAGTT  TATTTGCTTG       2040

TGCCCCCCTT  CTTTCTGTTG  CTTATTTCTC  ATTTCTGCGT  TCCGCGCTCC  CTGA             2094
```

( 2 ) INFORMATION FOR SEQ ID NO:2:

( i ) SEQUENCE CHARACTERISTICS:
        ( A ) LENGTH: 2100 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: MEXICO, FIGURE 7

( x i ) SEQUENCE DESCRIPTION: SEQ ID NO:2:

```
CTGAATGAAT  AACATGTGGT  TTGCTGCGCC  CATGGGTTCG  CCACCATGCG  CCCTAGGCCT         60

CTTTTGCTGT  TGTTCCTCTT  GTTTCTGCCT  ATGTTGCCCG  CGCCACCGAC  CGGTCAGCCG        120

TCTGGCCGCC  GTCGTGGGCG  GCGCAGCGGC  GGTACCGGCG  GTGGTTTCTG  GGGTGACCGG        180

GTTGATTCTC  AGCCCTTCGC  AATCCCCTAT  ATTCATCCAA  CCAACCCCTT  TGCCCCAGAC        240

GTTGCCGCTG  CGTCCGGGTC  TGGACCTCGC  CTTCGCCAAC  CAGCCCGGCC  ACTTGGCTCC        300

ACTTGGCGAG  ATCAGGCCCA  GCGCCCCTCC  GCTGCCTCCC  GTCGCCGACC  TGCCACAGCC        360
```

| | | | | | | |
|---|---|---|---|---|---|---|
| GGGGCTGCGG | CGCTGACGGC | TGTGGCGCCT | GCCCATGACA | CCTCACCCGT | CCCGGACGTT | 420 |
| GATTCTCGCG | GTGCAATTCT | ACGCCGCCAG | TATAATTTGT | CTACTTCACC | CCTGACATCC | 480 |
| TCTGTGGCCT | CTGGCACTAA | TTTAGTCCTG | TATGCAGCCC | CCCTTAATCC | GCCTCTGCCG | 540 |
| CTGCAGGACG | GTACTAATAC | TCACATTATG | GCCACAGAGG | CCTCCAATTA | TGCACAGTAC | 600 |
| CGGGTTGCCC | GCGCTACTAT | CCGTTACCGG | CCCCTAGTGC | CTAATGCAGT | GGAGGCTAT | 660 |
| GCTATATCCA | TTTCTTTCTG | GCCTCAAACA | ACCACAACCC | CTACATCTGT | TGACATGAAT | 720 |
| TCCATTACTT | CCACTGATGT | CAGGATTCTT | GTTCAACCTG | GCATAGCATC | TGAATTGGTC | 780 |
| ATCCCAAGCG | AGCGCCTTCA | CTACCGCAAT | CAAGGTTGGC | GCTCGGTTGA | GACATCTGGT | 840 |
| GTTGCTGAGG | AGGAAGCCAC | CTCCGGTCTT | GTCATGTTAT | GCATACATGG | CTCTCCAGTT | 900 |
| AACTCCTATA | CCAATACCCC | TTATACCGGT | GCCCTTGGCT | TACTGGACTT | TGCCTTAGAG | 960 |
| CTTGAGTTTC | GCAATCTCAC | CACCTGTAAC | ACCAATACAC | GTGTGTCCCG | TTACTCCAGC | 1020 |
| ACTGCTCGTC | ACTCCGCCCG | AGGGGCCGAC | GGGACTGCGG | AGCTGACCAC | AACTGCAGCC | 1080 |
| ACCAGGTTCA | TGAAAGATCT | CCACTTTACC | GGCCTTAATG | GGTAGGTGA | AGTCGGCCGC | 1140 |
| GGGATAGCTC | TAACATTACT | TAACCTTGCT | GACACGCTCC | TCGGCGGGCT | CCCGACAGAA | 1200 |
| TTAATTTCGT | CGGCTGGCGG | GCAACTGTTT | TATTCCCGCC | CGGTTGTCTC | AGCCAATGGC | 1260 |
| GAGCCAACCG | TGAAGCTCTA | TACATCAGTG | GAGAATGCTC | AGCAGGATAA | GGGTGTTGCT | 1320 |
| ATCCCCACG | ATATCGATCT | TGGTGATTCG | CGTGTGGTCA | TTCAGGATTA | TGACAACCAG | 1380 |
| CATGAGCAGG | ATCGGCCCAC | CCCGTCGCCT | GCGCCATCTC | GGCCTTTTC | TGTTCTCCGA | 1440 |
| GCAAATGATG | TACTTTGGCT | GTCCCTCACT | GCAGCCGAGT | ATGACCAGTC | CACTTACGGG | 1500 |
| TCGTCAACTG | GCCCGGTTTA | TATCTCGGAC | AGCGTGACTT | TGGTGAATGT | TGCGACTGGC | 1560 |
| GCGCAGGCCG | TAGCCCGATC | GCTTGACTGG | TCCAAAGTCA | CCCTCGACGG | GCGGCCCCTC | 1620 |
| CCGACTGTTG | AGCAATATTC | CAAGACATTC | TTTGTGCTCC | CCCTTCGTGG | CAAGCTCTCC | 1680 |
| TTTTGGGAGG | CCGGCACAAC | AAAAGCAGGT | TATCCTTATA | ATTATAATAC | TACTGCTAGT | 1740 |
| GACCAGATTC | TGATTGAAAA | TGCTGCCGGC | CATCGGGTCG | CCATTTCAAC | CTATACCACC | 1800 |
| AGGCTTGGGG | CCGGTCCGGT | CGCCATTTCT | GCGGCCGCGG | TTTTGGCTCC | ACGCTCCGCC | 1860 |
| CTGGCTCTGC | TGGAGGATAC | TTTTGATTAT | CCGGGGCGGG | CGCACACATT | TGATGACTTC | 1920 |
| TGCCCTGAAT | GCCGCGCTTT | AGGCCTCCAG | GGTTGTGCTT | TCCAGTCAAC | TGTCGCTGAG | 1980 |
| CTCCAGCGCC | TTAAAGTTAA | GGTGGGTAAA | ACTCGGGAGT | TGTAGTTTAT | TTGGCTGTGC | 2040 |
| CCACCTACTT | ATATCTGCTG | ATTTCCTTTA | TTTCCTTTTT | CTCGGTCCCG | CGCTCCCTGA | 2100 |

( 2 ) INFORMATION FOR SEQ ID NO:3:

( i ) SEQUENCE CHARACTERISTICS:
        ( A ) LENGTH: 2049 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: ORF 2, BURMA, FIGURE 7

( x i ) SEQUENCE DESCRIPTION: SEQ ID NO:3:

| | | | | | | |
|---|---|---|---|---|---|---|
| ATGCGCCCTC | GGCCTATTTT | GTTGCTGCTC | CTCATGTTTT | TGCCTATGCT | GCCCGCGCCA | 60 |
| CCGCCCGGTC | AGCCGTCTGG | CCGCCGTCGT | GGGCGGCGCA | GCGGCGGTTC | CGGCGGTGGT | 120 |

```
TTCTGGGGTG  ACCGGGTTGA  TTCTCAGCCC  TTCGCAATCC  CCTATATTCA  TCCAACCAAC   180

CCCTTCGCCC  CCGATGTCAC  CGCTGCGGCC  GGGGCTGGAC  CTCGTGTTCG  CCAACCCGCC   240

CGACCACTCG  GCTCCGCTTG  GCGTGACCAG  GCCCAGCGCC  CCGCCGTTGC  CTCACGTCGT   300

AGACCTACCA  CAGCTGGGGC  CGCGCCGCTA  ACCGCGGTCG  CTCCGGCCCA  TGACACCCCG   360

CCAGTGCCTG  ATGTCGACTC  CCGCGGCGCC  ATCTTGCGCC  GGCAGTATAA  CCTATCAACA   420

TCTCCCCTTA  CCTCTTCCGT  GGCCACCGGC  ACTAACCTGG  TTCTTTATGC  CGCCCCTCTT   480

AGTCCGCTTT  TACCCCTTCA  GGACGGCACC  AATACCCATA  TAATGGCCAC  GGAAGCTTCT   540

AATTATGCCC  AGTACCGGGT  TGCCCGTGCC  ACAATCCGTT  ACCGCCCGCT  GGTCCCCAAT   600

GCTGTCGGCG  GTTACGCCAT  CTCCATCTCA  TTCTGGCCAC  AGACCACCAC  CACCCCGACG   660

TCCGTTGATA  TGAATTCAAT  AACCTCGACG  GATGTTCGTA  TTTTAGTCCA  GCCCGGCATA   720

GCCTCTGAGC  TTGTGATCCC  AAGTGAGCGC  CTACACTATC  GTAACCAAGG  CTGGCGCTCC   780

GTCGAGACCT  CTGGGGTGGC  TGAGGAGGAG  GCTACCTCTG  GTCTTGTTAT  GCTTTGCATA   840

CATGGCTCAC  TCGTAAATTC  CTATACTAAT  ACACCCTATA  CCGGTGCCCT  CGGGCTGTTG   900

GACTTTGCCC  TTGAGCTTGA  GTTTCGCAAC  CTTACCCCCG  GTAACACCAA  TACGCGGGTC   960

TCCCGTTATT  CCAGCACTGC  TCGCCACCGC  CTTCGTCGCG  GTGCGGACGG  GACTGCCGAG  1020

CTCACCACCA  CGGCTGCTAC  CCGCTTTATG  AAGGACCTCT  ATTTACTAG   TACTAATGGT  1080

GTCGGTGAGA  TCGGCCGCGG  GATAGCCCTC  ACCCTGTTCA  ACCTTGCTGA  CACTCTGCTT  1140

GGCGGCCTGC  CGACAGAATT  GATTTCGTCG  GCTGGTGGCC  AGCTGTTCTA  CTCCCGTCCC  1200

GTTGTCTCAG  CCAATGGCGA  GCCGACTGTT  AAGTTGTATA  CATCTGTAGA  GAATGCTCAG  1260

CAGGATAAGG  GTATTGCAAT  CCCGCATGAC  ATTGACCTCG  GAGAATCTCG  TGTGGTTATT  1320

CAGGATTATG  ATAACCAACA  TGAACAAGAT  CGGCCGACGC  CTTCTCCAGC  CCCATCGCGC  1380

CCTTTCTCTG  TCCTTCGAGC  TAATGATGTG  CTTTGGCTCT  CTCTCACCGC  TGCCGAGTAT  1440

GACCAGTCCA  CTTATGGCTC  TTCGACTGGC  CCAGTTTATG  TTTCTGACTC  TGTGACCTTG  1500

GTTAATGTTG  CGACCGGCGC  GCAGGCCGTT  GCCCGGTCGC  TCGATTGGAC  CAAGGTCACA  1560

CTTGACGGTC  GCCCCCTCTC  CACCATCCAG  CAGTACTCGA  AGACCTTCTT  TGTCCTGCCG  1620

CTCCGCGGTA  AGCTCTCTTT  CTGGGAGGCA  GGCACAACTA  AAGCCGGGTA  CCCTTATAAT  1680

TATAACACCA  CTGCTAGCGA  CCAACTGCTT  GTCGAGAATG  CCGCCGGGCA  CCGGGTCGCT  1740

ATTTCCACTT  ACACCACTAG  CCTGGGTGCT  GGTCCGTCT   CCATTCTGC   GGTTGCCGTT  1800

TTAGCCCCCC  ACTCTGCGCT  AGCATTGCTT  GAGGATACCT  TGGACTACCC  TGCCCGCGCC  1860

CATACTTTTG  ATGATTTCTG  CCCAGAGTGC  CGCCCCTTG   GCCTTCAGGG  CTGCGCTTTC  1920

CAGTCTACTG  TCGCTGAGCT  TCAGCGCCTT  AAGATGAAGG  TGGGTAAAAC  TCGGGAGTTG  1980

TAGTTTATTT  GCTTGTGCCC  CCCTTCTTTC  TGTTGCTTAT  TTCTCATTTC  TGCGTTCCGC  2040

GCTCCCTGA                                                              2049
```

(2) INFORMATION FOR SEQ ID NO:4:

(i) SEQUENCE CHARACTERISTICS:
        (A) LENGTH: 2055 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (vi) ORIGINAL SOURCE:

( C ) INDIVIDUAL ISOLATE: ORF 2, MEXICO, FIGURE 7

( x i ) SEQUENCE DESCRIPTION: SEQ ID NO:4:

| | | | | | | |
|---|---|---|---|---|---|---|
| ATGCGCCCTA | GGCCTCTTTT | GCTGTTGTTC | CTCTTGTTTC | TGCCTATGTT | GCCCGCGCCA | 60 |
| CCGACCGGTC | AGCCGTCTGG | CCGCCGTCGT | GGGCGGCGCA | GCGGCGGTAC | CGGCGGTGGT | 120 |
| TTCTGGGGTG | ACCGGGTTGA | TTCTCAGCCC | TTCGCAATCC | CCTATATTCA | TCCAACCAAC | 180 |
| CCCTTTGCCC | CAGACGTTGC | CGCTGCGTCC | GGGTCTGGAC | CTCGCCTTCG | CCAACCAGCC | 240 |
| CGGCCACTTG | GCTCCACTTG | GCGAGATCAG | GCCCAGCGCC | CCTCCGCTGC | CTCCGTCGC | 300 |
| CGACCTGCCA | CAGCCGGGGC | TGCGGCGCTG | ACGGCTGTGG | CGCCTGCCCA | TGACACCTCA | 360 |
| CCCGTCCCGG | ACGTTGATTC | TCGCGGTGCA | ATTCTACGCC | GCCAGTATAA | TTTGTCTACT | 420 |
| TCACCCCTGA | CATCCTCTGT | GGCCTCTGGC | ACTAATTTAG | TCCTGTATGC | AGCCCCCTT | 480 |
| AATCCGCCTC | TGCCGCTGCA | GGACGGTACT | AATACTCACA | TTATGGCCAC | AGAGGCCTCC | 540 |
| AATTATGCAC | AGTACCGGGT | TGCCCGCGCT | ACTATCCGTT | ACCGGCCCCT | AGTGCCTAAT | 600 |
| GCAGTTGGAG | GCTATGCTAT | ATCCATTTCT | TTCTGGCCTC | AAACAACCAC | AACCCCTACA | 660 |
| TCTGTTGACA | TGAATTCCAT | TACTTCCACT | GATGTCAGGA | TTCTTGTTCA | ACCTGGCATA | 720 |
| GCATCTGAAT | TGGTCATCCC | AAGCGAGCGC | CTTCACTACC | GCAATCAAGG | TTGGCGCTCG | 780 |
| GTTGAGACAT | CTGGTGTTGC | TGAGGAGGAA | GCCACCTCCG | TCTTGTCAT | GTTATGCATA | 840 |
| CATGGCTCTC | CAGTTAACTC | CTATACCAAT | ACCCCTTATA | CCGGTGCCCT | TGGCTTACTG | 900 |
| GACTTTGCCT | TAGAGCTTGA | GTTTCGCAAT | CTCACCACCT | GTAACACCAA | TACACGTGTG | 960 |
| TCCCGTTACT | CCAGCACTGC | TCGTCACTCC | GCCCGAGGGG | CCGACGGGAC | TGCGGAGCTG | 1020 |
| ACCACAACTG | CAGCCACCAG | GTTCATGAAA | GATCTCCACT | TACCGGCCT | TAATGGGGTA | 1080 |
| GGTGAAGTCG | GCCGCGGGAT | AGCTCTAACA | TTACTTAACC | TTGCTGACAC | GCTCCTCGGC | 1140 |
| GGGCTCCCGA | CAGAATTAAT | TTCGTCGGCT | GGCGGGCAAC | TGTTTTATTC | CCGCCCGGTT | 1200 |
| GTCTCAGCCA | ATGGCGAGCC | AACCGTGAAG | CTCTATACAT | CAGTGGAGAA | TGCTCAGCAG | 1260 |
| GATAAGGGTG | TTGCTATCCC | CCACGATATC | GATCTTGGTG | ATTCGCGTGT | GGTCATTCAG | 1320 |
| GATTATGACA | ACCAGCATGA | GCAGGATCGG | CCCACCCCGT | CGCCTGCGCC | ATCTCGGCCT | 1380 |
| TTTTCTGTTC | TCCGAGCAAA | TGATGTACTT | TGGCTGTCCC | TCACTGCAGC | CGAGTATGAC | 1440 |
| CAGTCCACTT | ACGGGTCGTC | AACTGGCCCG | GTTTATATCT | CGGACAGCGT | GACTTTGGTG | 1500 |
| AATGTTGCGA | CTGGCGCGCA | GGCCGTAGCC | CGATCGCTTG | ACTGGTCCAA | AGTCACCCTC | 1560 |
| GACGGGCGGC | CCCTCCCGAC | TGTTGAGCAA | TATTCCAAGA | CATTCTTTGT | GCTCCCCTT | 1620 |
| CGTGGCAAGC | TCTCCTTTTG | GGAGGCCGGC | ACAACAAAAG | CAGGTTATCC | TTATAATTAT | 1680 |
| AATACTACTG | CTAGTGACCA | GATTCTGATT | GAAAATGCTG | CCGGCCATCG | GGTCGCCATT | 1740 |
| TCAACCTATA | CCACCAGGCT | TGGGGCCGGT | CCGGTCGCCA | TTTCTGCGGC | CGCGGTTTTG | 1800 |
| GCTCCACGCT | CCGCCCTGGC | TCTGCTGGAG | GATACTTTTG | ATTATCCGGG | GCGGGCGCAC | 1860 |
| ACATTTGATG | ACTTCTGCCC | TGAATGCCGC | GCTTTAGGCC | TCCAGGGTTG | TGCTTTCCAG | 1920 |
| TCAACTGTCG | CTGAGCTCCA | GCGCCTTAAA | GTTAAGGTGG | GTAAAACTCG | GGAGTTGTAG | 1980 |
| TTTATTTGGC | TGTGCCCACC | TACTTATATC | TGCTGATTTC | CTTTATTTCC | TTTTTCTCGG | 2040 |
| TCCCGCGCTC | CCTGA | | | | | 2055 |

( 2 ) INFORMATION FOR SEQ ID NO:5:

( i ) SEQUENCE CHARACTERISTICS:
( A ) LENGTH: 147 base pairs
( B ) TYPE: nucleic acid (C) STRANDEDNESS: double
(D) TOPOLOGY: linear (i i) MOLECULE TYPE: cDNA to mRNA (i i i) HYPOTHETICAL: NO (v i) ORIGINAL SOURCE:
(C) INDIVIDUAL ISOLATE: 406.3-2, BURMA, FIGURE 7

(x i) SEQUENCE DESCRIPTION: SEQ ID NO:5:

```
ACCTTGGACT ACCCTGCCCG CGCCCATACT TTTGATGATT TCTGCCCAGA GTGCCGCCCC      60
CTTGGCCTTC AGGGCTGCGC TTTCCAGTCT ACTGTCGCTG AGCTTCAGCG CCTTAAGATG     120
AAGGTGGGTA AAACTCGGGA GTTGTAG                                         147
```

(2) INFORMATION FOR SEQ ID NO:6:

(i) SEQUENCE CHARACTERISTICS:
(A) LENGTH: 147 base pairs
(B) TYPE: nucleic acid
(C) STRANDEDNESS: double
(D) TOPOLOGY: linear (i i) MOLECULE TYPE: cDNA to mRNA (i i i) HYPOTHETICAL: NO (v i) ORIGINAL SOURCE:
(C) INDIVIDUAL ISOLATE: 406.3-2, MEXICO, FIGURE 7

(x i) SEQUENCE DESCRIPTION: SEQ ID NO:6:

```
ACTTTTGATT ATCCGGGGCG GGCGCACACA TTTGATGACT TCTGCCCTGA ATGCCGCGCT      60
TTAGGCCTCC AGGGTTGTGC TTTCCAGTCA ACTGTCGCTG AGCTCCAGCG CCTTAAAGTT     120
AAGGTGGGTA AAACTCGGGA GTTGTAG                                         147
```

(2) INFORMATION FOR SEQ ID NO:7:

(i) SEQUENCE CHARACTERISTICS:
(A) LENGTH: 984 base pairs
(B) TYPE: nucleic acid
(C) STRANDEDNESS: double
(D) TOPOLOGY: linear (i i) MOLECULE TYPE: cDNA to mRNA (i i i) HYPOTHETICAL: NO (v i) ORIGINAL SOURCE:
(C) INDIVIDUAL ISOLATE: SG3, BURMA, FIGURE 7

(x i) SEQUENCE DESCRIPTION: SEQ ID NO:7:

```
GGTGCGGACG GGACTGCCGA GCTCACCACC ACGGCTGCTA CCCGCTTTAT GAAGGACCTC      60
TATTTTACTA GTACTAATGG TGTCGGTGAG ATCGGCCGCG GGATAGCCCT CACCCTGTTC     120
AACCTTGCTG ACACTCTGCT TGGCGGCCTG CCGACAGAAT TGATTTCGTC GGCTGGTGGC     180
CAGCTGTTCT ACTCCCGTCC CGTTGTCTCA GCCAATGGCG AGCCGACTGT TAAGTTGTAT     240
ACATCTGTAG AGAATGCTCA GCAGGATAAG GGTATTGCAA TCCCGCATGA CATTGACCTC     300
GGAGAATCTC GTGTGGTTAT TCAGGATTAT GATAACCAAC ATGAACAAGA TCGGCCGACG     360
CCTTCTCCAG CCCCATCGCG CCCTTTCTCT GTCCTTCGAG CTAATGATGT GCTTTGGCTC     420
TCTCTCACCG CTGCCGAGTA TGACCAGTCC ACTTATGGCT CTTCGACTGG CCCAGTTTAT     480
GTTTCTGACT CTGTGACCTT GGTTAATGTT GCGACCGGCG CGCAGGCCGT TGCCCGGTCG     540
CTCGATTGGA CCAAGGTCAC ACTTGACGGT CGCCCCCTCT CCACCATCCA GCAGTACTCG     600
```

| | | | | | | |
|---|---|---|---|---|---|---|
| AAGACCTTCT | TTGTCCTGCC | GCTCCGCGGT | AAGCTCTCTT | TCTGGGAGGC | AGGCACAACT | 660 |
| AAAGCCGGGT | ACCCTTATAA | TTATAACACC | ACTGCTAGCG | ACCAACTGCT | TGTCGAGAAT | 720 |
| GCCGCCGGGC | ACCGGGTCGC | TATTTCCACT | TACACCACTA | GCCTGGGTGC | TGGTCCCGTC | 780 |
| TCCATTTCTG | CGGTTGCCGT | TTTAGCCCCC | CACTCTGCGC | TAGCATTGCT | TGAGGATACC | 840 |
| TTGGACTACC | CTGCCCGCGC | CCATACTTTT | GATGATTTCT | GCCCAGAGTG | CCGCCCCTT | 900 |
| GGCCTTCAGG | GCTGCGCTTT | CCAGTCTACT | GTCGCTGAGC | TTCAGCGCCT | TAAGATGAAG | 960 |
| GTGGGTAAAA | CTCGGGAGTT | GTAG | | | | 984 |

( 2 ) INFORMATION FOR SEQ ID NO:8:

( i ) SEQUENCE CHARACTERISTICS:
        ( A ) LENGTH: 981 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: SG3, MEXICO, FIGURE 7

( x i ) SEQUENCE DESCRIPTION: SEQ ID NO:8:

| | | | | | | |
|---|---|---|---|---|---|---|
| GCCGACGGGA | CTGCGGAGCT | GACCACAACT | GCAGCCACCA | GGTTCATGAA | AGATCTCCAC | 60 |
| TTTACCGGCC | TTAATGGGGT | AGGTGAAGTC | GGCCGCGGGA | TAGCTCTAAC | ATTACTTAAC | 120 |
| CTTGCTGACA | CGCTCCTCGG | CGGGCTCCCG | ACAGAATTAA | TTTCGTCGGC | TGGCGGGCAA | 180 |
| CTGTTTTATT | CCCGCCCGGT | TGTCTCAGCC | AATGGCGAGC | CAACCGTGAA | GCTCTATACA | 240 |
| TCAGTGGAGA | ATGCTCAGCA | GGATAAGGGT | GTTGCTATCC | CCCACGATAT | CGATCTTGGT | 300 |
| GATTCGCGTG | TGGTCATTCA | GGATTATGAC | AACCAGCATG | AGCAGGATCG | GCCCACCCCG | 360 |
| TCGCCTGCGC | CATCTCGGCC | TTTTTCTGTT | CTCCGAGCAA | ATGATGTACT | TTGGCTGTCC | 420 |
| CTCACTGCAG | CCGAGTATGA | CCAGTCCACT | TACGGGTCGT | CAACTGGCCC | GGTTTATATC | 480 |
| TCGGACAGCG | TGACTTTGGT | GAATGTTGCG | ACTGGCGCGC | AGGCCGTAGC | CCGATCGCTT | 540 |
| GACTGGTCCA | AAGTCACCCT | CGACGGGCGG | CCCCTCCCGA | CTGTTGAGCA | ATATTCCAAG | 600 |
| ACATTCTTTG | TGCTCCCCCT | TCGTGGCAAG | CTCTCCTTTT | GGGAGGCCGG | CACAACAAAA | 660 |
| GCAGGTTATC | CTTATAATTA | TAATACTACT | GCTAGTGACC | AGATTCTGAT | TGAAAATGCT | 720 |
| GCCGGCCATC | GGGTCGCCAT | TTCAACCTAT | ACCACCAGGC | TTGGGGCCGG | TCCGGTCGCC | 780 |
| ATTTCTGCGG | CCGCGGTTTT | GGCTCCACGC | TCCGCCCTGG | CTCTGCTGGA | GGATACTTTT | 840 |
| GATTATCCGG | GGCGGGCGCA | CACATTTGAT | GACTTCTGCC | CTGAATGCCG | CGCTTTAGGC | 900 |
| CTCCAGGGTT | GTGCTTTCCA | GTCAACTGTC | GCTGAGCTCC | AGCGCCTTAA | AGTTAAGGTG | 960 |
| GGTAAAACTC | GGGAGTTGTA | G | | | | 981 |

( 2 ) INFORMATION FOR SEQ ID NO:9:

( i ) SEQUENCE CHARACTERISTICS:
        ( A ) LENGTH: 1311 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:

(C) INDIVIDUAL ISOLATE: C2, BURMA, FIGURE 7

(x i) SEQUENCE DESCRIPTION: SEQ ID NO:9:

| | | | | | | |
|---|---|---|---|---|---|---|
| AATTCAATAA | CCTCGACGGA | TGTTCGTATT | TTAGTCCAGC | CCGGCATAGC | CTCTGAGCTT | 60 |
| GTGATCCCAA | GTGAGCGCCT | ACACTATCGT | AACCAAGGCT | GGCGCTCCGT | CGAGACCTCT | 120 |
| GGGGTGGCTG | AGGAGGAGGC | TACCTCTGGT | CTTGTTATGC | TTTGCATACA | TGGCTCACTC | 180 |
| GTAAATTCCT | ATACTAATAC | ACCCTATACC | GGTGCCCTCG | GGCTGTTGGA | CTTTGCCCTT | 240 |
| GAGCTTGAGT | TTCGCAACCT | TACCCCCGGT | AACACCAATA | CGCGGGTCTC | CCGTTATTCC | 300 |
| AGCACTGCTC | GCCACCGCCT | TCGTCGCGGT | GCGGACGGGA | CTGCCGAGCT | CACCACCACG | 360 |
| GCTGCTACCC | GCTTTATGAA | GGACCTCTAT | TTTACTAGTA | CTAATGGTGT | CGGTGAGATC | 420 |
| GGCCGCGGGA | TAGCCCTCAC | CCTGTTCAAC | CTTGCTGACA | CTCTGCTTGG | CGGCCTGCCG | 480 |
| ACAGAATTGA | TTTCGTCGGC | TGGTGGCCAG | CTGTTCTACT | CCCGTCCCGT | TGTCTCAGCC | 540 |
| AATGGCGAGC | CGACTGTTAA | GTTGTATACA | TCTGTAGAGA | ATGCTCAGCA | GGATAAGGGT | 600 |
| ATTGCAATCC | CGCATGACAT | TGACCTCGGA | GAATCTCGTG | TGGTTATTCA | GGATTATGAT | 660 |
| AACCAACATG | AACAAGATCG | GCCGACGCCT | TCTCCAGCCC | CATCGCGCCC | TTTCTCTGTC | 720 |
| CTTCGAGCTA | ATGATGTGCT | TTGGCTCTCT | CTCACCGCTG | CCGAGTATGA | CCAGTCCACT | 780 |
| TATGGCTCTT | CGACTGGCCC | AGTTTATGTT | TCTGACTCTG | TGACCTTGGT | TAATGTTGCG | 840 |
| ACCGGCGCGC | AGGCCGTTGC | CCGGTCGCTC | GATTGGACCA | AGGTCACACT | TGACGGTCGC | 900 |
| CCCCTCTCCA | CCATCCAGCA | GTACTCGAAG | ACCTTCTTTG | TCCTGCCGCT | CCGCGGTAAG | 960 |
| CTCTCTTTCT | GGGAGGCAGG | CACAACTAAA | GCCGGGTACC | CTTATAATTA | TAACACCACT | 1020 |
| GCTAGCGACC | AACTGCTTGT | CGAGAATGCC | GCCGGGCACC | GGGTCGCTAT | TTCCACTTAC | 1080 |
| ACCACTAGCC | TGGGTGCTGG | TCCCGTCTCC | ATTTCTGCGG | TTGCCGTTTT | AGCCCCCCAC | 1140 |
| TCTGCGCTAG | CATTGCTTGA | GGATACCTTG | GACTACCCTG | CCCGCGCCCA | TACTTTTGAT | 1200 |
| GATTTCTGCC | CAGAGTGCCG | CCCCCTTGGC | CTTCAGGGCT | GCGCTTTCCA | GTCTACTGTC | 1260 |
| GCTGAGCTTC | AGCGCCTTAA | GATGAAGGTG | GGTAAAACTC | GGGAGTTGTA | G | 1311 |

(2) INFORMATION FOR SEQ ID NO:10:

(i) SEQUENCE CHARACTERISTICS:
        (A) LENGTH: 1308 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (v i) ORIGINAL SOURCE:
        (C) INDIVIDUAL ISOLATE: C2, MEXICO, FIGURE 7

(x i) SEQUENCE DESCRIPTION: SEQ ID NO:10:

| | | | | | | |
|---|---|---|---|---|---|---|
| AATTCCATTA | CTTCCACTGA | TGTCAGGATT | CTTGTTCAAC | CTGGCATAGC | ATCTGAATTG | 60 |
| GTCATCCCAA | GCGAGCGCCT | TCACTACCGC | AATCAAGGTT | GGCGCTCGGT | TGAGACATCT | 120 |
| GGTGTTGCTG | AGGAGGAAGC | CACCTCCGGT | CTTGTCATGT | TATGCATACA | TGGCTCTCCA | 180 |
| GTTAACTCCT | ATACCAATAC | CCCTTATACC | GGTGCCCTTG | GCTTACTGGA | CTTTGCCTTA | 240 |
| GAGCTTGAGT | TTCGCAATCT | CACCACCTGT | AACACCAATA | CACGTGTGTC | CCGTTACTCC | 300 |
| AGCACTGCTC | GTCACTCCGC | CCGAGGGGCC | GACGGGACTG | CGGAGCTGAC | CACAACTGCA | 360 |
| GCCACCAGGT | TCATGAAAGA | TCTCCACTTT | ACCGGCCTTA | ATGGGGTAGG | TGAAGTCGGC | 420 |

| | | | | | |
|---|---|---|---|---|---|
| CGCGGGATAG | CTCTAACATT | ACTTAACCTT | GCTGACACGC | TCCTCGGCGG | GCTCCCGACA | 480 |
| GAATTAATTT | CGTCGGCTGG | CGGGCAACTG | TTTTATTCCC | GCCCGGTTGT | CTCAGCCAAT | 540 |
| GGCGAGCCAA | CCGTGAAGCT | CTATACATCA | GTGGAGAATG | CTCAGCAGGA | TAAGGGTGTT | 600 |
| GCTATCCCCC | ACGATATCGA | TCTTGGTGAT | TCGCGTGTGG | TCATTCAGGA | TTATGACAAC | 660 |
| CAGCATGAGC | AGGATCGGCC | CACCCCGTCG | CCTGCGCCAT | CTCGGCCTTT | TTCTGTTCTC | 720 |
| CGAGCAAATG | ATGTACTTTG | GCTGTCCCTC | ACTGCAGCCG | AGTATGACCA | GTCCACTTAC | 780 |
| GGGTCGTCAA | CTGGCCCGGT | TTATATCTCG | GACAGCGTGA | CTTTGGTGAA | TGTTGCGACT | 840 |
| GGCGCGCAGG | CCGTAGCCCG | ATCGCTTGAC | TGGTCCAAAG | TCACCCTCGA | CGGGCGGCCC | 900 |
| CTCCCGACTG | TTGAGCAATA | TTCCAAGACA | TTCTTTGTGC | TCCCCCTTCG | TGGCAAGCTC | 960 |
| TCCTTTTGGG | AGGCCGGCAC | AACAAAAGCA | GGTTATCCTT | ATAATTATAA | TACTACTGCT | 1020 |
| AGTGACCAGA | TTCTGATTGA | AAATGCTGCC | GGCCATCGGG | TCGCCATTTC | AACCTATACC | 1080 |
| ACCAGGCTTG | GGGCCGGTCC | GGTCGCCATT | TCTGCGGCCG | CGGTTTTGGC | TCCACGCTCC | 1140 |
| GCCCTGGCTC | TGCTGGAGGA | TACTTTTGAT | TATCCGGGGC | GGGCGCACAC | ATTTGATGAC | 1200 |
| TTCTGCCCTG | AATGCCGCGC | TTTAGGCCTC | CAGGGTTGTG | CTTTCCAGTC | AACTGTCGCT | 1260 |
| GAGCTCCAGC | GCCTTAAAGT | TAAGGTGGGT | AAAACTCGGG | AGTTGTAG | | 1308 |

( 2 ) INFORMATION FOR SEQ ID NO:11:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: 406.4-2, BURMA, FIGURE 7

( x i ) SEQUENCE DESCRIPTION: SEQ ID NO:11:

| | | | | | |
|---|---|---|---|---|---|
| GCCAACCCGC | CCGACCACTC | GGCTCCGCTT | GGCGTGACCA | GGCCCAGCGC | CCCGCCGTTG | 60 |
| CCTCACGTCG | TAGACCTACC | ACAGCTGGGG | CCGCGCCGCT | AA | | 102 |

( 2 ) INFORMATION FOR SEQ ID NO:12:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( C ) INDIVIDUAL ISOLATE: 406.4-2, MEXICO, FIGURE 7

( x i ) SEQUENCE DESCRIPTION: SEQ ID NO:12:

| | | | | | |
|---|---|---|---|---|---|
| GCCAACCAGC | CCGGCCACTT | GGCTCCACTT | GGCGAGATCA | GGCCCAGCGC | CCCTCCGCTG | 60 |
| CCTCCCGTCG | CCGACCTGCC | ACAGCCGGGG | CTGCGGCGCT | GA | | 102 |

( 2 ) INFORMATION FOR SEQ ID NO:13:

( i ) SEQUENCE CHARACTERISTICS:
        ( A ) LENGTH: 48 amino acids
        ( B ) TYPE: amino acid (D) TOPOLOGY: linear (ii) MOLECULE TYPE: protein (iii) HYPOTHETICAL: NO (vi) ORIGINAL SOURCE:
    (C) INDIVIDUAL ISOLATE: ORF2, 406.3-2, BURMA, FIGURE 9

(xi) SEQUENCE DESCRIPTION: SEQ ID NO:13:

| Thr | Leu | Asp | Tyr | Pro | Ala | Arg | Ala | His | Thr | Phe | Asp | Asp | Phe | Cys | Pro |
|---|---|---|---|---|---|---|---|---|---|---|---|---|---|---|---|
| 1 | | | | 5 | | | | | 10 | | | | | 15 | |
| Glu | Cys | Arg | Pro | Leu | Gly | Leu | Gln | Gly | Cys | Ala | Phe | Gln | Ser | Thr | Val |
| | | | 20 | | | | | 25 | | | | | 30 | | |
| Ala | Glu | Leu | Gln | Arg | Leu | Lys | Met | Lys | Val | Gly | Lys | Thr | Arg | Glu | Leu |
| | | | 35 | | | | | 40 | | | | | 45 | | |

(2) INFORMATION FOR SEQ ID NO:14:

(i) SEQUENCE CHARACTERISTICS:
    (A) LENGTH: 48 amino acids
    (B) TYPE: amino acid
    (D) TOPOLOGY: linear (ii) MOLECULE TYPE: protein (iii) HYPOTHETICAL: NO (vi) ORIGINAL SOURCE:
    (C) INDIVIDUAL ISOLATE: ORF2, 406.3-2, MEXICO, FIGURE 9

(xi) SEQUENCE DESCRIPTION: SEQ ID NO:14:

| Thr | Phe | Asp | Tyr | Pro | Gly | Arg | Ala | His | Thr | Phe | Asp | Asp | Phe | Cys | Pro |
|---|---|---|---|---|---|---|---|---|---|---|---|---|---|---|---|
| 1 | | | | 5 | | | | | 10 | | | | | 15 | |
| Glu | Cys | Arg | Ala | Leu | Gly | Leu | Gln | Gly | Cys | Ala | Phe | Gln | Ser | Thr | Val |
| | | | 20 | | | | | 25 | | | | | 30 | | |
| Ala | Glu | Leu | Gln | Arg | Leu | Lys | Val | Lys | Val | Gly | Lys | Thr | Arg | Glu | Leu |
| | | | 35 | | | | | 40 | | | | | 45 | | |

(2) INFORMATION FOR SEQ ID NO:15:

(i) SEQUENCE CHARACTERISTICS:
    (A) LENGTH: 327 amino acids
    (B) TYPE: amino acid
    (D) TOPOLOGY: linear (ii) MOLECULE TYPE: protein (iii) HYPOTHETICAL: NO (vi) ORIGINAL SOURCE:
    (C) INDIVIDUAL ISOLATE: SG3, BURMA, FIGURE 9

(xi) SEQUENCE DESCRIPTION: SEQ ID NO:15:

| Gly | Ala | Asp | Gly | Thr | Ala | Glu | Leu | Thr | Thr | Thr | Ala | Ala | Thr | Arg | Phe |
|---|---|---|---|---|---|---|---|---|---|---|---|---|---|---|---|
| 1 | | | | 5 | | | | | 10 | | | | | 15 | |
| Met | Lys | Asp | Leu | Tyr | Phe | Thr | Ser | Thr | Asn | Gly | Val | Gly | Glu | Ile | Gly |
| | | | 20 | | | | | 25 | | | | | 30 | | |
| Arg | Gly | Ile | Ala | Leu | Thr | Leu | Phe | Asn | Leu | Ala | Asp | Thr | Leu | Leu | Gly |
| | | | 35 | | | | | 40 | | | | | 45 | | |
| Gly | Leu | Pro | Thr | Glu | Leu | Ile | Ser | Ser | Ala | Gly | Gly | Gln | Leu | Phe | Tyr |
| | | | 50 | | | | | 55 | | | | | 60 | | |
| Ser | Arg | Pro | Val | Val | Ser | Ala | Asn | Gly | Glu | Pro | Thr | Val | Lys | Leu | Tyr |
| 65 | | | | | 70 | | | | | 75 | | | | | 80 |
| Thr | Ser | Val | Glu | Asn | Ala | Gln | Gln | Asp | Lys | Gly | Ile | Ala | Ile | Pro | His |
| | | | | 85 | | | | | 90 | | | | | 95 | |

```
Asp  Ile  Asp  Leu  Gly  Glu  Ser  Arg  Val  Val  Ile  Gln  Asp  Tyr  Asp  Asn
               100                 105                      110

Gln  His  Glu  Gln  Asp  Arg  Pro  Thr  Pro  Ser  Pro  Ala  Pro  Ser  Arg  Pro
          115                      120                      125

Phe  Ser  Val  Leu  Arg  Ala  Asn  Asp  Val  Leu  Trp  Leu  Ser  Leu  Thr  Ala
     130                      135                      140

Ala  Glu  Tyr  Asp  Gln  Ser  Thr  Tyr  Gly  Ser  Ser  Thr  Gly  Pro  Val  Tyr
145                      150                      155                      160

Val  Ser  Asp  Ser  Val  Thr  Leu  Val  Asn  Val  Ala  Thr  Gly  Ala  Gln  Ala
               165                      170                      175

Val  Ala  Arg  Ser  Leu  Asp  Trp  Thr  Lys  Val  Thr  Leu  Asp  Gly  Arg  Pro
               180                      185                      190

Leu  Ser  Thr  Ile  Gln  Gln  Tyr  Ser  Lys  Thr  Phe  Phe  Val  Leu  Pro  Leu
          195                      200                      205

Arg  Gly  Lys  Leu  Ser  Phe  Trp  Glu  Ala  Gly  Thr  Thr  Lys  Ala  Gly  Tyr
     210                      215                      220

Pro  Tyr  Asn  Tyr  Asn  Thr  Thr  Ala  Ser  Asp  Gln  Leu  Leu  Val  Glu  Asn
225                      230                      235                      240

Ala  Ala  Gly  His  Arg  Val  Ala  Ile  Ser  Thr  Tyr  Thr  Thr  Ser  Leu  Gly
               245                      250                      255

Ala  Gly  Pro  Val  Ser  Ile  Ser  Ala  Val  Ala  Val  Leu  Ala  Pro  His  Ser
               260                      265                      270

Ala  Leu  Ala  Leu  Leu  Glu  Asp  Thr  Leu  Asp  Tyr  Pro  Ala  Arg  Ala  His
          275                      280                      285

Thr  Phe  Asp  Asp  Phe  Cys  Pro  Glu  Cys  Arg  Pro  Leu  Gly  Leu  Gln  Gly
     290                      295                      300

Cys  Ala  Phe  Gln  Ser  Thr  Val  Ala  Glu  Leu  Gln  Arg  Leu  Lys  Met  Lys
305                      310                      315                      320

Val  Gly  Lys  Thr  Arg  Glu  Leu
                    325
```

( 2 ) INFORMATION FOR SEQ ID NO:16:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SG3, MEXICO, FIGURE 9

( x i ) SEQUENCE DESCRIPTION: SEQ ID NO:16:

```
Gly  Ala  Asp  Gly  Thr  Ala  Glu  Leu  Thr  Thr  Thr  Ala  Ala  Thr  Arg  Phe
1              5                        10                       15

Met  Lys  Asp  Leu  His  Phe  Thr  Gly  Leu  Asn  Gly  Val  Gly  Glu  Val  Gly
               20                       25                       30

Arg  Gly  Ile  Ala  Leu  Thr  Leu  Leu  Asn  Leu  Ala  Asp  Thr  Leu  Leu  Gly
          35                       40                       45

Gly  Leu  Pro  Thr  Glu  Leu  Ile  Ser  Ser  Ala  Gly  Gln  Leu  Phe  Tyr
     50                       55                       60

Ser  Arg  Pro  Val  Val  Ser  Ala  Asn  Gly  Glu  Pro  Thr  Val  Lys  Leu  Tyr
65                       70                       75                       80

Thr  Ser  Val  Glu  Asn  Ala  Gln  Gln  Asp  Lys  Gly  Val  Ala  Ile  Pro  His
               85                       90                       95
```

```
Asp  Ile  Asp  Leu  Gly  Asp  Ser  Arg  Val  Val  Ile  Gln  Asp  Tyr  Asp  Asn
               100                      105                     110

Gln  His  Glu  Gln  Asp  Arg  Pro  Thr  Pro  Ser  Pro  Ala  Pro  Ser  Arg  Pro
          115                      120                     125

Phe  Ser  Val  Leu  Arg  Ala  Asn  Asp  Val  Leu  Trp  Leu  Ser  Leu  Thr  Ala
     130                      135                          140

Ala  Glu  Tyr  Asp  Gln  Ser  Thr  Tyr  Gly  Ser  Ser  Thr  Gly  Pro  Val  Tyr
145                           150                     155                     160

Ile  Ser  Asp  Ser  Val  Thr  Leu  Val  Asn  Val  Ala  Thr  Gly  Ala  Gln  Ala
                    165                      170                     175

Val  Ala  Arg  Ser  Leu  Asp  Trp  Ser  Lys  Val  Thr  Leu  Asp  Gly  Arg  Pro
               180                      185                          190

Leu  Pro  Thr  Val  Glu  Gln  Tyr  Ser  Lys  Thr  Phe  Phe  Val  Leu  Pro  Leu
          195                      200                     205

Arg  Gly  Lys  Leu  Ser  Phe  Trp  Glu  Ala  Gly  Thr  Thr  Lys  Ala  Gly  Tyr
               210                      215                     220

Pro  Tyr  Asn  Tyr  Asn  Thr  Thr  Ala  Ser  Asp  Gln  Ile  Leu  Ile  Glu  Asn
225                           230                     235                     240

Ala  Ala  Gly  His  Arg  Val  Ala  Ile  Ser  Thr  Tyr  Thr  Thr  Arg  Leu  Gly
                    245                      250                     255

Ala  Gly  Pro  Val  Ala  Ile  Ser  Ala  Ala  Val  Leu  Ala  Pro  Arg  Ser
               260                      265                     270

Ala  Leu  Ala  Leu  Leu  Glu  Asp  Thr  Phe  Asp  Tyr  Pro  Gly  Arg  Ala  His
          275                      280                     285

Thr  Phe  Asp  Asp  Phe  Cys  Pro  Glu  Cys  Arg  Ala  Leu  Gly  Leu  Gln  Gly
          290                      295                     300

Cys  Ala  Phe  Gln  Ser  Thr  Val  Ala  Glu  Leu  Gln  Arg  Leu  Lys  Val  Lys
305                      310                      315                     320

Val  Gly  Lys  Thr  Arg  Glu  Leu
                    325
```

( 2 ) INFORMATION FOR SEQ ID NO:17:

( i ) SEQUENCE CHARACTERISTICS:
        ( A ) LENGTH: 436 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: C2, BURMA, FIGURE 9

( x i ) SEQUENCE DESCRIPTION: SEQ ID NO:17:

```
Asn  Ser  Ile  Thr  Ser  Thr  Asp  Val  Arg  Ile  Leu  Val  Gln  Pro  Gly  Ile
1              5                         10                      15

Ala  Ser  Glu  Leu  Val  Ile  Pro  Ser  Glu  Arg  Leu  His  Tyr  Arg  Asn  Gln
               20                      25                      30

Gly  Trp  Arg  Ser  Val  Glu  Thr  Ser  Gly  Val  Ala  Glu  Glu  Glu  Ala  Thr
               35                      40                      45

Ser  Gly  Leu  Val  Met  Leu  Cys  Ile  His  Gly  Ser  Leu  Val  Asn  Ser  Tyr
          50                      55                      60

Thr  Asn  Thr  Pro  Tyr  Thr  Gly  Ala  Leu  Gly  Leu  Leu  Asp  Phe  Ala  Leu
65                       70                      75                      80

Glu  Leu  Glu  Phe  Arg  Asn  Leu  Thr  Pro  Gly  Asn  Thr  Asn  Thr  Arg  Val
               85                      90                      95
```

| | | | | | | | | | | | | | |
|---|---|---|---|---|---|---|---|---|---|---|---|---|---|
| Ser | Arg | Tyr | Ser<br>100 | Ser | Thr | Ala | Arg | His<br>105 | Arg | Leu | Arg | Arg<br>110 | Gly | Ala | Asp |
| Gly | Thr | Ala<br>115 | Glu | Leu | Thr | Thr | Thr<br>120 | Ala | Ala | Thr | Arg<br>125 | Phe | Met | Lys | Asp |
| Leu | Tyr<br>130 | Phe | Thr | Ser | Thr | Asn<br>135 | Gly | Val | Gly | Glu | Ile<br>140 | Gly | Arg | Gly | Ile |
| Ala<br>145 | Leu | Thr | Leu | Phe | Asn<br>150 | Leu | Ala | Asp | Thr | Leu<br>155 | Leu | Gly | Gly | Leu | Pro<br>160 |
| Thr | Glu | Leu | Ile | Ser<br>165 | Ser | Ala | Gly | Gly | Gln<br>170 | Leu | Phe | Tyr | Ser | Arg<br>175 | Pro |
| Val | Val | Ser | Ala<br>180 | Asn | Gly | Glu | Pro | Thr<br>185 | Val | Lys | Leu | Tyr | Thr<br>190 | Ser | Val |
| Glu | Asn | Ala<br>195 | Gln | Gln | Asp | Lys | Gly<br>200 | Ile | Ala | Ile | Pro | His<br>205 | Asp | Ile | Asp |
| Leu | Gly<br>210 | Glu | Ser | Arg | Val | Val<br>215 | Ile | Gln | Asp | Tyr | Asp<br>220 | Asn | Gln | His | Glu |
| Gln<br>225 | Asp | Arg | Pro | Thr | Pro<br>230 | Ser | Pro | Ala | Pro | Ser<br>235 | Arg | Pro | Phe | Ser | Val<br>240 |
| Leu | Arg | Ala | Asn | Asp<br>245 | Val | Leu | Trp | Leu | Ser<br>250 | Leu | Thr | Ala | Ala | Glu<br>255 | Tyr |
| Asp | Gln | Ser | Thr<br>260 | Tyr | Gly | Ser | Ser | Thr<br>265 | Gly | Pro | Val | Tyr | Val<br>270 | Ser | Asp |
| Ser | Val | Thr<br>275 | Leu | Val | Asn | Val | Ala<br>280 | Thr | Gly | Ala | Gln | Ala<br>285 | Val | Ala | Arg |
| Ser | Leu<br>290 | Asp | Trp | Thr | Lys | Val<br>295 | Thr | Leu | Asp | Gly | Arg<br>300 | Pro | Leu | Ser | Thr |
| Ile<br>305 | Gln | Gln | Tyr | Ser | Lys<br>310 | Thr | Phe | Phe | Val | Leu<br>315 | Pro | Leu | Arg | Gly | Lys<br>320 |
| Leu | Ser | Phe | Trp | Glu<br>325 | Ala | Gly | Thr | Thr | Lys<br>330 | Ala | Gly | Tyr | Pro | Tyr<br>335 | Asn |
| Tyr | Asn | Thr | Thr<br>340 | Ala | Ser | Asp | Gln | Leu<br>345 | Leu | Val | Glu | Asn | Ala<br>350 | Ala | Gly |
| His | Arg | Val<br>355 | Ala | Ile | Ser | Thr | Tyr<br>360 | Thr | Thr | Ser | Leu | Gly<br>365 | Ala | Gly | Pro |
| Val | Ser<br>370 | Ile | Ser | Ala | Val | Ala<br>375 | Val | Leu | Ala | Pro | His<br>380 | Ser | Ala | Leu | Ala |
| Leu<br>385 | Leu | Glu | Asp | Thr | Leu<br>390 | Asp | Tyr | Pro | Ala | Arg<br>395 | Ala | His | Thr | Phe | Asp<br>400 |
| Asp | Phe | Cys | Pro | Glu<br>405 | Cys | Arg | Pro | Leu | Gly<br>410 | Leu | Gln | Gly | Cys | Ala<br>415 | Phe |
| Gln | Ser | Thr | Val<br>420 | Ala | Glu | Leu | Gln | Arg<br>425 | Leu | Lys | Met | Lys | Val<br>430 | Gly | Lys |
| Thr | Arg | Glu | Leu<br>435 | | | | | | | | | | | | |

(2) INFORMATION FOR SEQ ID NO:18:

(i) SEQUENCE CHARACTERISTICS:
        (A) LENGTH: 435 amino acids
        (B) TYPE: amino acid
        (D) TOPOLOGY: linear (ii) MOLECULE TYPE: protein (iii) HYPOTHETICAL: NO (vi) ORIGINAL SOURCE:

(C) INDIVIDUAL ISOLATE: C2, MEXICO, FIGURE 9

(xi) SEQUENCE DESCRIPTION: SEQ ID NO:18:

```
Asn  Ser  Ile  Thr  Ser  Thr  Asp  Val  Arg  Ile  Leu  Val  Gln  Pro  Gly  Ile
1              5                        10                       15

Ala  Ser  Glu  Leu  Val  Ile  Pro  Ser  Glu  Arg  Leu  His  Tyr  Arg  Asn  Gln
               20                       25                  30

Gly  Trp  Arg  Ser  Val  Glu  Thr  Ser  Gly  Val  Ala  Glu  Glu  Ala  Thr
          35                      40                       45

Ser  Gly  Leu  Val  Met  Leu  Cys  Ile  His  Gly  Ser  Pro  Val  Asn  Ser  Tyr
     50                       55                      60

Thr  Asn  Thr  Pro  Tyr  Thr  Gly  Ala  Leu  Gly  Leu  Leu  Asp  Phe  Ala  Leu
65                       70                  75                       80

Glu  Leu  Glu  Phe  Arg  Asn  Leu  Thr  Thr  Cys  Asn  Thr  Asn  Thr  Arg  Val
               85                       90                       95

Ser  Arg  Tyr  Ser  Ser  Thr  Ala  Arg  His  Ser  Ala  Arg  Gly  Ala  Asp  Gly
               100                      105                      110

Thr  Ala  Glu  Leu  Thr  Thr  Thr  Ala  Ala  Thr  Arg  Phe  Met  Lys  Asp  Leu
               115                      120                 125

His  Phe  Thr  Gly  Leu  Asn  Gly  Val  Gly  Glu  Val  Gly  Arg  Gly  Ile  Ala
     130                      135                      140

Leu  Thr  Leu  Leu  Asn  Leu  Ala  Asp  Thr  Leu  Leu  Gly  Gly  Leu  Pro  Thr
145                      150                      155                      160

Glu  Leu  Ile  Ser  Ser  Ala  Gly  Gly  Gln  Leu  Phe  Tyr  Ser  Arg  Pro  Val
                    165                      170                      175

Val  Ser  Ala  Asn  Gly  Glu  Pro  Thr  Val  Lys  Leu  Tyr  Thr  Ser  Val  Glu
                    180                      185                      190

Asn  Ala  Gln  Gln  Asp  Lys  Gly  Val  Ala  Ile  Pro  His  Asp  Ile  Asp  Leu
               195                      200                 205

Gly  Asp  Ser  Arg  Val  Val  Ile  Gln  Asp  Tyr  Asp  Asn  Gln  His  Glu  Gln
     210                      215                      220

Asp  Arg  Pro  Thr  Pro  Ser  Pro  Ala  Pro  Ser  Arg  Pro  Phe  Ser  Val  Leu
225                      230                      235                      240

Arg  Ala  Asn  Asp  Val  Leu  Trp  Leu  Ser  Leu  Thr  Ala  Ala  Glu  Tyr  Asp
               245                      250                      255

Gln  Ser  Thr  Tyr  Gly  Ser  Ser  Thr  Gly  Pro  Val  Tyr  Ile  Ser  Asp  Ser
               260                      265                      270

Val  Thr  Leu  Val  Asn  Val  Ala  Thr  Gly  Ala  Gln  Ala  Val  Ala  Arg  Ser
          275                      280                      285

Leu  Asp  Trp  Ser  Lys  Val  Thr  Leu  Asp  Gly  Arg  Pro  Leu  Pro  Thr  Val
     290                      295                      300

Glu  Gln  Tyr  Ser  Lys  Thr  Phe  Phe  Val  Leu  Pro  Leu  Arg  Gly  Lys  Leu
305                      310                      315                      320

Ser  Phe  Trp  Glu  Ala  Gly  Thr  Thr  Lys  Ala  Gly  Tyr  Pro  Tyr  Asn  Tyr
               325                      330                      335

Asn  Thr  Thr  Ala  Ser  Asp  Gln  Ile  Leu  Ile  Glu  Asn  Ala  Ala  Gly  His
               340                      345                      350

Arg  Val  Ala  Ile  Ser  Thr  Tyr  Thr  Thr  Arg  Leu  Gly  Ala  Gly  Pro  Val
          355                      360                      365

Ala  Ile  Ser  Ala  Ala  Ala  Val  Leu  Ala  Pro  Arg  Ser  Ala  Leu  Ala  Leu
     370                      375                      380

Leu  Glu  Asp  Thr  Phe  Asp  Tyr  Pro  Gly  Arg  Ala  His  Thr  Phe  Asp  Asp
385                      390                      395                      400

Phe  Cys  Pro  Glu  Cys  Arg  Ala  Leu  Gly  Leu  Gln  Gly  Cys  Ala  Phe  Gln
```

|           |           |           | 405       |           |           |           | 410       |           |           |           | 415       |           |
| Ser | Thr | Val | Ala | Glu | Leu | Gln | Arg | Leu | Lys | Val | Lys | Val | Gly | Lys | Thr |
|     |     |     | 420 |     |     |     | 425 |     |     |     |     |     | 430 |     |     |

Arg Glu Leu
        435

( 2 ) INFORMATION FOR SEQ ID NO:19:

( i ) SEQUENCE CHARACTERISTICS:
    ( A ) LENGTH: 660 amino acids
    ( B ) TYPE: amino acid
    ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: ORF 2, BURMA, FIGURE 9

( x i ) SEQUENCE DESCRIPTION: SEQ ID NO:19:

| Met | Arg | Pro | Arg | Pro | Ile | Leu | Leu | Leu | Leu | Leu | Met | Phe | Leu | Pro | Met |
| 1   |     |     |     | 5   |     |     |     |     | 10  |     |     |     |     | 15  |     |
| Leu | Pro | Ala | Pro | Pro | Gly | Gln | Pro | Ser | Gly | Arg | Arg | Arg | Gly | Arg |
|     |     |     | 20  |     |     |     | 25  |     |     |     |     | 30  |     |     |
| Arg | Ser | Gly | Gly | Ser | Gly | Gly | Gly | Phe | Trp | Gly | Asp | Arg | Val | Asp | Ser |
|     |     |     | 35  |     |     |     |     | 40  |     |     |     |     | 45  |     |     |
| Gln | Pro | Phe | Ala | Ile | Pro | Tyr | Ile | His | Pro | Thr | Asn | Pro | Phe | Ala | Pro |
|     |     |     | 50  |     |     |     | 55  |     |     |     |     | 60  |     |     |     |
| Asp | Val | Thr | Ala | Ala | Ala | Gly | Ala | Gly | Pro | Arg | Val | Arg | Gln | Pro | Ala |
| 65  |     |     |     |     | 70  |     |     |     |     | 75  |     |     |     |     | 80  |
| Arg | Pro | Leu | Gly | Ser | Ala | Trp | Arg | Asp | Gln | Ala | Gln | Arg | Pro | Ala | Val |
|     |     |     |     | 85  |     |     |     |     | 90  |     |     |     |     | 95  |     |
| Ala | Ser | Arg | Arg | Arg | Pro | Thr | Thr | Ala | Gly | Ala | Ala | Pro | Leu | Thr | Ala |
|     |     |     |     | 100 |     |     |     |     | 105 |     |     |     |     | 110 |     |
| Val | Ala | Pro | Ala | His | Asp | Thr | Pro | Pro | Val | Pro | Asp | Val | Asp | Ser | Arg |
|     |     |     |     | 115 |     |     |     |     | 120 |     |     |     |     | 125 |     |
| Gly | Ala | Ile | Leu | Arg | Arg | Gln | Tyr | Asn | Leu | Ser | Thr | Ser | Pro | Leu | Thr |
|     |     |     | 130 |     |     |     |     | 135 |     |     |     |     | 140 |     |     |
| Ser | Ser | Val | Ala | Thr | Gly | Thr | Asn | Leu | Val | Leu | Tyr | Ala | Ala | Pro | Leu |
| 145 |     |     |     |     | 150 |     |     |     |     | 155 |     |     |     |     | 160 |
| Ser | Pro | Leu | Leu | Pro | Leu | Gln | Asp | Gly | Thr | Asn | Thr | His | Ile | Met | Ala |
|     |     |     |     | 165 |     |     |     |     | 170 |     |     |     |     | 175 |     |
| Thr | Glu | Ala | Ser | Asn | Tyr | Ala | Gln | Tyr | Arg | Val | Ala | Arg | Ala | Thr | Ile |
|     |     |     |     | 180 |     |     |     |     | 185 |     |     |     |     | 190 |     |
| Arg | Tyr | Arg | Pro | Leu | Val | Pro | Asn | Ala | Val | Gly | Gly | Tyr | Ala | Ile | Ser |
|     |     |     | 195 |     |     |     |     | 200 |     |     |     |     | 205 |     |     |
| Ile | Ser | Phe | Trp | Pro | Gln | Thr | Thr | Thr | Pro | Thr | Ser | Val | Asp | Met |
|     |     |     | 210 |     |     |     |     | 215 |     |     |     |     | 220 |     |     |
| Asn | Ser | Ile | Thr | Ser | Thr | Asp | Val | Arg | Ile | Leu | Val | Gln | Pro | Gly | Ile |
| 225 |     |     |     |     | 230 |     |     |     |     | 235 |     |     |     |     | 240 |
| Ala | Ser | Glu | Leu | Val | Ile | Pro | Ser | Glu | Arg | Leu | His | Tyr | Arg | Asn | Gln |
|     |     |     |     | 245 |     |     |     |     | 250 |     |     |     |     | 255 |     |
| Gly | Trp | Arg | Ser | Val | Glu | Thr | Ser | Gly | Val | Ala | Glu | Glu | Ala | Thr |
|     |     |     | 260 |     |     |     |     | 265 |     |     |     |     | 270 |     |     |
| Ser | Gly | Leu | Val | Met | Leu | Cys | Ile | His | Gly | Ser | Leu | Val | Asn | Ser | Tyr |
|     |     |     | 275 |     |     |     |     | 280 |     |     |     |     | 285 |     |     |
| Thr | Asn | Thr | Pro | Tyr | Thr | Gly | Ala | Leu | Gly | Leu | Leu | Asp | Phe | Ala | Leu |

-continued

```
                290                              295                              300
    Glu  Leu  Glu  Phe  Arg  Asn  Leu  Thr  Pro  Gly  Asn  Thr  Asn  Thr  Arg  Val
    305                      310                      315                      320

Ser  Arg  Tyr  Ser  Ser  Thr  Ala  Arg  His  Arg  Leu  Arg  Arg  Gly  Ala  Asp
                        325                      330                      335

Gly  Thr  Ala  Glu  Leu  Thr  Thr  Thr  Ala  Ala  Thr  Arg  Phe  Met  Lys  Asp
                   340                      345                      350

Leu  Tyr  Phe  Thr  Ser  Thr  Asn  Gly  Val  Gly  Glu  Ile  Gly  Arg  Gly  Ile
              355                      360                      365

Ala  Leu  Thr  Leu  Phe  Asn  Leu  Ala  Asp  Thr  Leu  Leu  Gly  Gly  Leu  Pro
    370                      375                      380

Thr  Glu  Leu  Ile  Ser  Ser  Ala  Gly  Gly  Gln  Leu  Phe  Tyr  Ser  Arg  Pro
    385                      390                      395                      400

Val  Val  Ser  Ala  Asn  Gly  Glu  Pro  Thr  Val  Lys  Leu  Tyr  Thr  Ser  Val
                        405                      410                      415

Glu  Asn  Ala  Gln  Gln  Asp  Lys  Gly  Ile  Ala  Ile  Pro  His  Asp  Ile  Asp
                   420                      425                      430

Leu  Gly  Glu  Ser  Arg  Val  Val  Ile  Gln  Asp  Tyr  Asp  Asn  Gln  His  Glu
              435                      440                      445

Gln  Asp  Arg  Pro  Thr  Pro  Ser  Pro  Ala  Pro  Ser  Arg  Pro  Phe  Ser  Val
    450                      455                      460

Leu  Arg  Ala  Asn  Asp  Val  Leu  Trp  Leu  Ser  Leu  Thr  Ala  Ala  Glu  Tyr
    465                      470                      475                      480

Asp  Gln  Ser  Thr  Tyr  Gly  Ser  Ser  Thr  Gly  Pro  Val  Tyr  Val  Ser  Asp
                        485                      490                      495

Ser  Val  Thr  Leu  Val  Asn  Val  Ala  Thr  Gly  Ala  Gln  Ala  Val  Ala  Arg
                   500                      505                      510

Ser  Leu  Asp  Trp  Thr  Lys  Val  Thr  Leu  Asp  Gly  Arg  Pro  Leu  Ser  Thr
              515                      520                      525

Ile  Gln  Gln  Tyr  Ser  Lys  Thr  Phe  Phe  Val  Leu  Pro  Leu  Arg  Gly  Lys
    530                      535                      540

Leu  Ser  Phe  Trp  Glu  Ala  Gly  Thr  Thr  Lys  Ala  Gly  Tyr  Pro  Tyr  Asn
    545                      550                      555                      560

Tyr  Asn  Thr  Thr  Ala  Ser  Asp  Gln  Leu  Leu  Val  Glu  Asn  Ala  Ala  Gly
                        565                      570                      575

His  Arg  Val  Ala  Ile  Ser  Thr  Tyr  Thr  Thr  Ser  Leu  Gly  Ala  Gly  Pro
                   580                      585                      590

Val  Ser  Ile  Ser  Ala  Val  Ala  Val  Leu  Ala  Pro  His  Ser  Ala  Leu  Ala
              595                      600                      605

Leu  Leu  Glu  Asp  Thr  Leu  Asp  Tyr  Pro  Ala  Arg  Ala  His  Thr  Phe  Asp
    610                      615                      620

Asp  Phe  Cys  Pro  Glu  Cys  Arg  Pro  Leu  Gly  Leu  Gln  Gly  Cys  Ala  Phe
    625                      630                      635                      640

Gln  Ser  Thr  Val  Ala  Glu  Leu  Gln  Arg  Leu  Lys  Met  Lys  Val  Gly  Lys
                        645                      650                      655

Thr  Arg  Glu  Leu
                   660
```

( 2 ) INFORMATION FOR SEQ ID NO:20:

( i ) SEQUENCE CHARACTERISTICS:
        ( A ) LENGTH: 659 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
    ( C ) INDIVIDUAL ISOLATE: ORF 2, MEXICO, FIGURE 9

( x i ) SEQUENCE DESCRIPTION: SEQ ID NO:20:

```
Met Arg Pro Arg Pro Leu Leu Leu Leu Phe Leu Leu Phe Leu Pro Met
 1               5                  10                 15

Leu Pro Ala Pro Pro Thr Gly Gln Pro Ser Gly Arg Arg Arg Gly Arg
             20              25              30

Arg Ser Gly Gly Thr Gly Gly Gly Phe Trp Gly Asp Arg Val Asp Ser
         35              40              45

Gln Pro Phe Ala Ile Pro Tyr Ile His Pro Thr Asn Pro Phe Ala Pro
     50              55              60

Asp Val Ala Ala Ala Ser Gly Ser Gly Pro Arg Leu Arg Gln Pro Ala
 65              70              75              80

Arg Pro Leu Gly Ser Thr Trp Arg Asp Gln Ala Gln Arg Pro Ser Ala
             85              90              95

Ala Ser Arg Arg Arg Pro Ala Thr Ala Gly Ala Ala Ala Leu Thr Ala
             100             105             110

Val Ala Pro Ala His Asp Thr Ser Pro Val Pro Asp Val Asp Ser Arg
             115             120             125

Gly Ala Ile Leu Arg Ar

```
Glu  Leu  Ile  Ser  Ser  Ala  Gly  Gly  Gln  Leu  Phe  Tyr  Ser  Arg  Pro  Val
385                      390                      395                      400

Val  Ser  Ala  Asn  Gly  Glu  Pro  Thr  Val  Lys  Leu  Tyr  Thr  Ser  Val  Glu
                    405                      410                      415

Asn  Ala  Gln  Gln  Asp  Lys  Gly  Val  Ala  Ile  Pro  His  Asp  Ile  Asp  Leu
               420                      425                      430

Gly  Asp  Ser  Arg  Val  Val  Ile  Gln  Asp  Tyr  Asp  Asn  Gln  His  Glu  Gln
          435                      440                      445

Asp  Arg  Pro  Thr  Pro  Ser  Pro  Ala  Pro  Ser  Arg  Pro  Phe  Ser  Val  Leu
     450                      455                      460

Arg  Ala  Asn  Asp  Val  Leu  Trp  Leu  Ser  Leu  Thr  Ala  Ala  Glu  Tyr  Asp
465                      470                      475                      480

Gln  Ser  Thr  Tyr  Gly  Ser  Ser  Thr  Gly  Pro  Val  Tyr  Ile  Ser  Asp  Ser
                    485                      490                      495

Val  Thr  Leu  Val  Asn  Val  Ala  Thr  Gly  Ala  Gln  Ala  Val  Ala  Arg  Ser
               500                      505                      510

Leu  Asp  Trp  Ser  Lys  Val  Thr  Leu  Asp  Gly  Arg  Pro  Leu  Pro  Thr  Val
          515                      520                      525

Glu  Gln  Tyr  Ser  Lys  Thr  Phe  Phe  Val  Leu  Pro  Leu  Arg  Gly  Lys  Leu
     530                      535                      540

Ser  Phe  Trp  Glu  Ala  Gly  Thr  Thr  Lys  Ala  Gly  Tyr  Pro  Tyr  Asn  Tyr
545                      550                      555                      560

Asn  Thr  Thr  Ala  Ser  Asp  Gln  Ile  Leu  Ile  Glu  Asn  Ala  Ala  Gly  His
                    565                      570                      575

Arg  Val  Ala  Ile  Ser  Thr  Tyr  Thr  Thr  Arg  Leu  Gly  Ala  Gly  Pro  Val
               580                      585                      590

Ala  Ile  Ser  Ala  Ala  Ala  Val  Leu  Ala  Pro  Arg  Ser  Ala  Leu  Ala  Leu
          595                      600                      605

Leu  Glu  Asp  Thr  Phe  Asp  Tyr  Pro  Gly  Arg  Ala  His  Thr  Phe  Asp  Asp
     610                      615                      620

Phe  Cys  Pro  Glu  Cys  Arg  Ala  Leu  Gly  Leu  Gln  Gly  Cys  Ala  Phe  Gln
625                      630                      635                      640

Ser  Thr  Val  Ala  Glu  Leu  Gln  Arg  Leu  Lys  Val  Lys  Val  Gly  Lys  Thr
                    645                      650                      655

Arg  Glu  Leu
```

( 2 ) INFORMATION FOR SEQ ID NO:21:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: ORF3, 406.4- 2, BURMA, FIGURE 8

( x i ) SEQUENCE DESCRIPTION: SEQ ID NO:21:

```
Ala  Asn  Pro  Pro  Asp  His  Ser  Ala  Pro  Leu  Gly  Val  Thr  Arg  Pro  Ser
1                   5                        10                       15

Ala  Pro  Pro  Leu  Pro  His  Val  Val  Asp  Leu  Pro  Gln  Leu  Gly  Pro  Arg
               20                       25                       30

Arg
```

( 2 ) INFORMATION FOR SEQ ID NO:22:

( i ) SEQUENCE CHARACTERISTICS:
   ( A ) LENGTH: 33 amino acids
   ( B ) TYPE: amino acid
   ( D ) TOPOLOGY: linear ( i i ) MOLECULE TYPE: protein ( i i i ) HYPOTHETICAL: NO ( v i ) ORIGINAL SOURCE:
   ( C ) INDIVIDUAL ISOLATE: ORF3, 406.4- 2, MEXICO, FIGURE 8

( x i ) SEQUENCE DESCRIPTION: SEQ ID NO:22:

```
Ala Asn Gln Pro Gly His Leu Ala Pro Leu Gly Glu Ile Arg Pro Ser
1               5                   10                  15
Ala Pro Pro Leu Pro Pro Val Ala Asp Leu Pro Gln Pro Gly Leu Arg
            20                  25                  30
Arg
```

( 2 ) INFORMATION FOR SEQ ID NO:23:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
      ( C ) INDIVIDUAL ISOLATE: Fig. 11, ORF 1, aa 169-182

( x i ) SEQUENCE DESCRIPTION: SEQ ID NO:23:

```
Met Ser Pro Ser Asp Val Ala Glu Ala Met Phe Arg His Gly
1               5                   10
```

( 2 ) INFORMATION FOR SEQ ID NO:24:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
      ( C ) INDIVIDUAL ISOLATE: Fig. 11, ORF 1, aa 221-234

( x i ) SEQUENCE DESCRIPTION: SEQ ID NO:24:

```
Tyr Glu Gly Asp Thr Ser Ala Gly Tyr Asn His Asp Val Ser
1               5                   10
```

( 2 ) INFORMATION FOR SEQ ID NO:25:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: Fig. 11, ORF 1, aa 461-474

( x i ) SEQUENCE DESCRIPTION: SEQ ID NO:25:

```
Thr Ala Ile Arg Lys Ala Leu Ser Lys Phe Cys Cys Phe Met
1               5                   10
```

( 2 ) INFORMATION FOR SEQ ID NO:26:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 597-618

( x i ) SEQUENCE DESCRIPTION: SEQ ID NO:26:

```
Ser Gln Ser Thr Met Ala Ala Gly Pro Phe Ser Leu Thr Tyr Ala Ala
1               5                   10                      15

Ser Ala Ala Gly Leu Glu
                20
```

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 901-914

( x i ) SEQUENCE DESCRIPTION: SEQ ID NO:27:

```
Ala Trp Glu Arg Asn His Arg Pro Gly Asp Glu Leu Tyr Leu
1               5                   10
```

( 2 ) INFORMATION FOR SEQ ID NO:28:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 1185-1198

( x i ) SEQUENCE DESCRIPTION: SEQ ID NO:28:

```
Asp Ala Pro Gly Leu Leu Arg Glu Val Gly Ile Ser Asp Ala
1               5                   10
```

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Fig. 11, ORF 1, aa 1205-1222

(xi) SEQUENCE DESCRIPTION: SEQ ID NO:29:

```
Leu Ala Gly Gly Glu Ile Gly His Gln Arg Pro Ser Val Ile Pro Arg
1               5                   10                  15
Gly Asn
```

(2) INFORMATION FOR SEQ ID NO:30:

(i) SEQUENCE CHARACTERISTICS:
        (A) LENGTH: 18 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (vi) ORIGINAL SOURCE:
        (C) INDIVIDUAL ISOLATE: Fig. 11, ORF 1, aa 1237-1254

(xi) SEQUENCE DESCRIPTION: SEQ ID NO:30:

```
Cys Gln Ile Ser Ala Phe His Gln Leu Ala Glu Glu Leu Gly His Arg
1               5                   10                  15
Pro Val
```

(2) INFORMATION FOR SEQ ID NO:31:

(i) SEQUENCE CHARACTERISTICS:
        (A) LENGTH: 78 amino acids
        (B) TYPE: amino acid
        (C) STRANDEDNESS: single
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: Fig. 11, ORF 1, aa 1285-1362

(xi) SEQUENCE DESCRIPTION: SEQ ID NO:31:

```
Thr Phe Glu Leu Thr Asp Ile Val His Cys Arg Met Ala Ala Pro Ser
1               5                   10                  15
Gln Arg Lys Ala Val Leu Ser Thr Leu Val Gly Arg Tyr Gly Gly Arg
                20                  25                  30
```

```
        Thr  Lys  Leu  Tyr  Asn  Ala  Ser  His  Ser  Asp  Val  Arg  Asp  Ser  Leu  Ala
                  35                      40                      45

Arg  Phe  Ile  Pro  Ala  Ile  Gly  Pro  Val  Gln  Val  Thr  Thr  Cys  Glu  Leu
                  50                      55                      60

Tyr  Glu  Leu  Val  Glu  Ala  Met  Val  Glu  Lys  Gly  Gln  Asp  Gly
         65                      70                      75
```

( 2 ) INFORMATION FOR SEQ ID NO:32:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 1377-1410

( x i ) SEQUENCE DESCRIPTION: SEQ ID NO:32:

```
        Arg  Ile  Thr  Phe  Phe  Gln  Lys  Asp  Cys  Asn  Lys  Phe  Thr  Thr  Gly  Glu
         1                       5                      10                      15

Thr  Ile  Ala  His  Gly  Lys  Val  Gly  Gln  Gly  Ile  Ser  Ala  Trp  Ser  Lys
                           20                      25                      30

Thr  Phe
```

( 2 ) INFORMATION FOR SEQ ID NO:33:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 1429-1446

( x i ) SEQUENCE DESCRIPTION: SEQ ID NO:33:

```
        Ile  Glu  Lys  Ala  Ile  Leu  Ala  Leu  Leu  Pro  Gln  Gly  Val  Phe  Tyr  Gly
         1                       5                      10                      15

Asp  Ala  Phe  Asp  Asp  Thr  Val  Phe  Ser  Ala
                           20                      25
```

( 2 ) INFORMATION FOR SEQ ID NO:34:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: Fig. 11, ORF 1, aa 1505-1518

(x i) SEQUENCE DESCRIPTION: SEQ ID NO:34:

Pro Lys Glu Ser Leu Arg Gly Phe Trp Lys Lys His Ser Gly
1               5                   10

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v i) ORIGINAL SOURCE:
        (C) INDIVIDUAL ISOLATE: Fig. 11, ORF 2, aa 25-38

(x i) SEQUENCE DESCRIPTION: SEQ ID NO:35:

Pro Ser Gly Arg Arg Arg Gly Arg Arg Ser Gly Gly Ser Gly
1               5                   10

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v i) ORIGINAL SOURCE:
        (C) INDIVIDUAL ISOLATE: Fig. 11, ORF 2, aa 341-354

(x i) SEQUENCE DESCRIPTION: SEQ ID NO:36:

Leu Thr Thr Thr Ala Ala Thr Arg Phe Met Lys Asp Leu Tyr
1               5                   10

(2) INFORMATION FOR SEQ ID NO:37:

(i) SEQUENCE CHARACTERISTICS:
        (A) LENGTH: 14 amino acids
        (B) TYPE: amino acid
        (C) STRANDEDNESS: single
        (D) TOPOLOGY: unknown (i i) MOLECULE TYPE: peptide (i i i) HYPOTHETICAL: NO (i v) ANTI-SENSE: NO (v i) ORIGINAL SOURCE:
        (C) INDIVIDUAL ISOLATE: Fig. 11, ORF 2, aa 517-530

(x i) SEQUENCE DESCRIPTION: SEQ ID NO:37:

Thr Lys Val Thr Leu Asp Gly Arg Pro Leu Ser Thr Ile Gln
1               5                   10

(2) INFORMATION FOR SEQ ID NO:38:

(i) SEQUENCE CHARACTERISTICS:
        (A) LENGTH: 18 amino acids ( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: Fig. 11, ORF 3, aa 105-122

( x i ) SEQUENCE DESCRIPTION: SEQ ID NO:38:

```
Pro  Ser  Ala  Pro  Pro  Leu  Pro  His  Val  Val  Asp  Leu  Pro  Gln  Leu  Gly
1                   5                        10                       15
Pro  Arg
```

( 2 ) INFORMATION FOR SEQ ID NO:39:

( i ) SEQUENCE CHARACTERISTICS:
( A ) LENGTH: 33 amino acids
( B ) TYPE: amino acid
( C ) STRANDEDNESS: single
( D ) TOPOLOGY: unknown ( i i ) MOLECULE TYPE: peptide ( i i i ) HYPOTHETICAL: NO ( i v ) ANTI-SENSE: NO ( v i ) ORIGINAL SOURCE:
( C ) INDIVIDUAL ISOLATE: degenerate peptide, page 11, lines 22-24

( i x ) FEATURE:
( A ) NAME/KEY: Misc
( B ) LOCATION: 3..3
( D ) OTHER INFORMATION: /note= "where Xaa is either glutamine or proline"

( i x ) FEATURE:
( A ) NAME/KEY: Misc
( B ) LOCATION: 5..5
( D ) OTHER INFORMATION: /note= "where Xaa is either glycine or aspartic acid"

( i x ) FEATURE:
( A ) NAME/KEY: Misc
( B ) LOCATION: 7..7
( D ) OTHER INFORMATION: /note= "where Xaa is either leucine or serine"

( i x ) FEATURE:
( A ) NAME/KEY: Misc
( B ) LOCATION: 12..12
( D ) OTHER INFORMATION: /note= "where Xaa is either glutamic acid or valine"

( i x ) FEATURE:
( A ) NAME/KEY: Misc
( B ) LOCATION: 13..13
( D ) OTHER INFORMATION: /note= "where Xaa is either isoleucine or threonine"

( i x ) FEATURE:
( A ) NAME/KEY: Misc
( B ) LOCATION: 22..22
( D ) OTHER INFORMATION: /note= "where Xaa is either proline or histidine"

( i x ) FEATURE:
( A ) NAME/KEY: Misc
( B ) LOCATION: 24..24
( D ) OTHER INFORMATION: /note= "where Xaa is either alanine or valine"

( i x ) FEATURE:
    ( A ) NAME/KEY: Misc
    ( B ) LOCATION: 29..29
    ( D ) OTHER INFORMATION: /note= "where Xaa is either
        proline or leucine"

( i x ) FEATURE:
    ( A ) NAME/KEY: Misc
    ( B ) LOCATION: 31..31
    ( D ) OTHER INFORMATION: /note= "where Xaa is either
        leucine or proline"

( x i ) SEQUENCE DESCRIPTION: SEQ ID NO:39:

```
Ala  Asn  Xaa  Pro  Xaa  His  Xaa  Ala  Pro  Leu  Gly  Xaa  Xaa  Arg  Pro  Ser
1                  5                        10                       15
Ala  Pro  Pro  Leu  Pro  Xaa  Val  Xaa  Asp  Leu  Pro  Gln  Xaa  Gly  Xaa  Arg
               20                  25                       30
Arg
```

( 2 ) INFORMATION FOR SEQ ID NO:40:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:40:

GAATGAATAA CATGT        15

( 2 ) INFORMATION FOR SEQ ID NO:41:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:41:

TTTGCTGCGC CCATGGGTTC GC        22

( 2 ) INFORMATION FOR SEQ ID NO:42:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:42:

ACCATGCGCC CT  12

( 2 ) INFORMATION FOR SEQ ID NO:43:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:43:

TGCCCGCGCC ACCG  14

( 2 ) INFORMATION FOR SEQ ID NO:44:

( i ) SEQUENCE CHARACTERISTICS:
        ( A ) LENGTH: 44 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:44:

CCGGTCAGCC GTCTGGCCGC CGTCGTGGGC GGCGCAGCGG CGGT  44

( 2 ) INFORMATION FOR SEQ ID NO:45:

( i ) SEQUENCE CHARACTERISTICS:
        ( A ) LENGTH: 76 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:45:

CCGGCGGTGG TTTCTGGGGT GACCGGGTTG ATTCTCAGCC CTTCGCAATC CCCTATATTC  60

ATCCAACCAA CCCCTT  76

( 2 ) INFORMATION FOR SEQ ID NO:46:

( i ) SEQUENCE CHARACTERISTICS:
  ( A ) LENGTH: 10 base pairs
  ( B ) TYPE: nucleic acid
  ( C ) STRANDEDNESS: unknown
  ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:46:

CTGGACCTCG  10

( 2 ) INFORMATION FOR SEQ ID NO:47:

( i ) SEQUENCE CHARACTERISTICS:
  ( A ) LENGTH: 10 base pairs
  ( B ) TYPE: nucleic acid
  ( C ) STRANDEDNESS: unknown
  ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:47:

TTCGCCAACC  10

( 2 ) INFORMATION FOR SEQ ID NO:48:

( i ) SEQUENCE CHARACTERISTICS:
  ( A ) LENGTH: 15 base pairs
  ( B ) TYPE: nucleic acid
  ( C ) STRANDEDNESS: unknown
  ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:48:

CAGGCCCAGC GCCCC  15

( 2 ) INFORMATION FOR SEQ ID NO:49:

( i ) SEQUENCE CHARACTERISTICS:
  ( A ) LENGTH: 12 base pairs
  ( B ) TYPE: nucleic acid
  ( C ) STRANDEDNESS: unknown
  ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:49:

GCCCATGACA CC 12

( 2 ) INFORMATION FOR SEQ ID NO:50:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:50:

CAGTACCGGG TTGCCCG 17

( 2 ) INFORMATION FOR SEQ ID NO:51:

( i ) SEQUENCE CHARACTERISTICS:
( A ) LENGTH: 11 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:51:

ATCCGTTACC G 11

( 2 ) INFORMATION FOR SEQ ID NO:52:

( i ) SEQUENCE CHARACTERISTICS:
( A ) LENGTH: 11 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:52:

GCTGAGGAGG A 11

( 2 ) INFORMATION FOR SEQ ID NO:53:

( i ) SEQUENCE CHARACTERISTICS:
( A ) LENGTH: 14 base pairs
( B ) TYPE: nucleic acid
( C ) STRANDEDNESS: unknown
( D ) TOPOLOGY: unknown (i i) MOLECULE TYPE: DNA (i i i) HYPOTHETICAL: NO (i v) ANTI-SENSE: NO (v i) ORIGINAL SOURCE:
    (C) INDIVIDUAL ISOLATE: DNA sequence, Fig. 7

(x i) SEQUENCE DESCRIPTION: SEQ ID NO:53:

TGCATACATG GCTC  14

(2) INFORMATION FOR SEQ ID NO:54:

(i) SEQUENCE CHARACTERISTICS:
       (A) LENGTH: 14 base pairs
       (B) TYPE: nucleic acid
       (C) STRANDEDNESS: unknown
       (D) TOPOLOGY: unknown (i i) MOLECULE TYPE: DNA (i i i) HYPOTHETICAL: NO (i v) ANTI-SENSE: NO (v i) ORIGINAL SOURCE:
       (C) INDIVIDUAL ISOLATE: DNA sequence, Fig. 7

(x i) SEQUENCE DESCRIPTION: SEQ ID NO:54:

TATACCGGTG CCCT  14

(2) INFORMATION FOR SEQ ID NO:55:

(i) SEQUENCE CHARACTERISTICS:
       (A) LENGTH: 11 base pairs
       (B) TYPE: nucleic acid
       (C) STRANDEDNESS: unknown
       (D) TOPOLOGY: unknown (i i) MOLECULE TYPE: DNA (i i i) HYPOTHETICAL: NO (i v) ANTI-SENSE: NO (v i) ORIGINAL SOURCE:
       (C) INDIVIDUAL ISOLATE: DNA sequence, Fig. 7

(x i) SEQUENCE DESCRIPTION: SEQ ID NO:55:

TGGACTTTGC C  11

(2) INFORMATION FOR SEQ ID NO:56:

(i) SEQUENCE CHARACTERISTICS:
       (A) LENGTH: 17 base pairs
       (B) TYPE: nucleic acid
       (C) STRANDEDNESS: unknown
       (D) TOPOLOGY: unknown (i i) MOLECULE TYPE: DNA (i i i) HYPOTHETICAL: NO (i v) ANTI-SENSE: NO (v i) ORIGINAL SOURCE:
       (C) INDIVIDUAL ISOLATE: DNA sequence, Fig. 7

(x i) SEQUENCE DESCRIPTION: SEQ ID NO:56:

GAGCTTGAGT TTCGCAA  17

( 2 ) INFORMATION FOR SEQ ID NO:57:

( i ) SEQUENCE CHARACTERISTICS:
        ( A ) LENGTH: 13 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:57:

GTAACACCAA TAC          13

( 2 ) INFORMATION FOR SEQ ID NO:58:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:58:

TCCAGCACTG CTCG         14

( 2 ) INFORMATION FOR SEQ ID NO:59:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DNA sequence, Fig. 7

( x i ) SEQUENCE DESCRIPTION: SEQ ID NO:59:

GACGGGACTG C          11

( 2 ) INFORMATION FOR SEQ ID NO:60:

( i ) SEQUENCE CHARACTERISTICS:
        ( A ) LENGTH: 16 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO -continued (vi) ORIGINAL SOURCE:
  (C) INDIVIDUAL ISOLATE: DNA sequence, Fig. 7

(xi) SEQUENCE DESCRIPTION: SEQ ID NO:60:

TCGGCCGCGG GATAGC                                                                                              16

(2) INFORMATION FOR SEQ ID NO:61:

(i) SEQUENCE CHARACTERISTICS:
    (A) LENGTH: 14 base pairs
    (B) TYPE: nucleic acid
    (C) STRANDEDNESS: unknown
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: DNA sequence, Fig. 7

(xi) SEQUENCE DESCRIPTION: SEQ ID NO:61:

AACCTTGCTG ACAC                                                                                                14

(2) INFORMATION FOR SEQ ID NO:62:

(i) SEQUENCE CHARACTERISTICS:
    (A) LENGTH: 11 base pairs
    (B) TYPE: nucleic acid
    (C) STRANDEDNESS: unknown
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: DNA sequence, Fig. 7

(xi) SEQUENCE DESCRIPTION: SEQ ID NO:62:

CCGACAGAAT T                                                                                                   11

(2) INFORMATION FOR SEQ ID NO:63:

(i) SEQUENCE CHARACTERISTICS:
    (A) LENGTH: 14 base pairs
    (B) TYPE: nucleic acid
    (C) STRANDEDNESS: unknown
    (D) TOPOLOGY: unknown (ii) MOLECULE TYPE: DNA (iii) HYPOTHETICAL: NO (iv) ANTI-SENSE: NO (vi) ORIGINAL SOURCE:
    (C) INDIVIDUAL ISOLATE: DNA sequence, Fig. 7

(xi) SEQUENCE DESCRIPTION: SEQ ID NO:63:

ATTTCGTCGG CTGG                                                                                                14

(2) INFORMATION FOR SEQ ID NO:64:

(i) SEQUENCE CHARACTERISTICS:
    (A) LENGTH: 23 base pairs
    (B) TYPE: nucleic acid
    (C) STRANDEDNESS: unknown ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:64:

GTTGTCTCAG CCAATGGCGA GCC               23

( 2 ) INFORMATION FOR SEQ ID NO:65:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:65:

GAGAATGCTC AGCAGGATAA GGGT              24

( 2 ) INFORMATION FOR SEQ ID NO:66:

( i ) SEQUENCE CHARACTERISTICS:
    ( A ) LENGTH: 14 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:66:

ATTCAGGATT ATGA                         14

( 2 ) INFORMATION FOR SEQ ID NO:67:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:67:

GCCGAGTATG ACCAGTCCAC TTA               23

( 2 ) INFORMATION FOR SEQ ID NO:68:

( i ) SEQUENCE CHARACTERISTICS:
( A ) LENGTH: 11 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:68:

A A T G T T G C G A C 11

( 2 ) INFORMATION FOR SEQ ID NO:69:

( i ) SEQUENCE CHARACTERISTICS:
( A ) LENGTH: 14 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:69:

G G C G C G C A G G C C G T 14

( 2 ) INFORMATION FOR SEQ ID NO:70:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DNA sequence, Fig. 7

( x i ) SEQUENCE DESCRIPTION: SEQ ID NO:70:

C T T A T A A T T A T A A 13

( 2 ) INFORMATION FOR SEQ ID NO:71:

( i ) SEQUENCE CHARACTERISTICS:
( A ) LENGTH: 12 base pairs
( B ) TYPE: nucleic acid
( C ) STRANDEDNESS: unknown
( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: DNA sequence, Fig. 7

( x i ) SEQUENCE DESCRIPTION: SEQ ID NO:71:

CCATTTCTGC GG 12

( 2 ) INFORMATION FOR SEQ ID NO:72:

( i ) SEQUENCE CHARACTERISTICS:
    ( A ) LENGTH: 11 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:72:

GCTTTCCAGT C 11

( 2 ) INFORMATION FOR SEQ ID NO:73:

( i ) SEQUENCE CHARACTERISTICS:
    ( A ) LENGTH: 14 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:73:

ACTGTCGCTG AGCT 14

( 2 ) INFORMATION FOR SEQ ID NO:74:

( i ) SEQUENCE CHARACTERISTICS:
    ( A ) LENGTH: 11 base pairs
    ( B ) TYPE: nucleic acid
    ( C ) STRANDEDNESS: unknown
    ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DNA sequence, Fig. 7

( x i ) SEQUENCE DESCRIPTION: SEQ ID NO:74:

CAGCGCCTTA A 11

( 2 ) INFORMATION FOR SEQ ID NO:75:

( i ) SEQUENCE CHARACTERISTICS:
    ( A ) LENGTH: 35 base pairs

```
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: DNA sequence, Fig. 7

( x i ) SEQUENCE DESCRIPTION: SEQ ID NO:75:

AAGGTGGGTA  AAACTCGGGA  GTTGTAGTTT  ATTTG                                   3 5

( 2 ) INFORMATION FOR SEQ ID NO:76:

( i ) SEQUENCE CHARACTERISTICS:
        ( A ) LENGTH: 13 base pairs
        ( B ) TYPE: nucleic acid
        ( C ) STRANDEDNESS: unknown
        ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( C ) INDIVIDUAL ISOLATE: DNA sequence, Fig. 7

( x i ) SEQUENCE DESCRIPTION: SEQ ID NO:76:

CCGCGCTCCC  TGA                                                             1 3
```

HEPATITIS E VIRUS PEPTIDE ANTIGEN AND ANTIBODIES

This application is a continuation-in-part of U.S. application Ser. No. 07/822,335, filed 17 Jan., 1992, now abandoned, herein incorporated by reference, which is a continuation-in-part of U.S. application Ser. No. 07/681,078, filed 5 Apr., 1991, now abandoned, which is a continuation-in-part of U.S. application Ser. No.07/505,888, filed Apr. 5, 1990, now abandoned, herein incorporated by reference, which is a continuation-in-part of U.S. application Ser. No. 420,921, filed Oct. 13, 1989, now abandoned, herein incorporated by reference, which is a continuation-in-part of U.S. application Ser. No. 367,486, filed Jun. 16, 1989, now abandoned, herein incorporated by reference, which is a continuation-in-part of U.S. application Ser. No. 336,672, filed Apr. 11, 1989, now abandoned, herein incorporated by reference, which is a continuation-in-part of U.S. application Ser. No. 208,997, filed Jun. 17, 1988, now abandoned, herein incorporated by reference.

FIELD OF THE INVENTION

This invention relates to antigen and antibody compositions related to enterically transmitted nonA/nonB hepatitis viral agent, also referred to herein as hepatitis E virus (HEV), and to vaccine methods.

REFERENCES

Arankalle, V. A., et al., The Lancet, 550 (Mar. 12, 1988).
Bradley, D. W., et al., J Gen. Virol., 69:1 (1988).
Bradley, D. W. et al., Proc. Nat. Acad. Sci., USA, 84:6277 (1987).
Dieckmann, C. L., et al., J. Biol. Chem. 260:1513 (1985).
Engleman, E. G., et al., eds., *Human Hybridomas and Monoclonal Antibodies*, Plenum Press, 1985.
Geysen, H. M., et al., J. Immunol Methods, 102:259 (1987).
Gravelle, C. R. et al., J. Infect. Diseases, 131:167 (1975).
Hyams, K. C., et al., Lancet, in press.
Kane, M. A., et al., JAMA, 252:3140 (1984).
Khuroo, M. S., *Am. J. Med.,* 48:818 (1980).
Khuroo, M. S., et al., Am. J. Med., 68:818 (1983).
Kyte, J., et al., J Mol Biol, 157:105 (1982).
Lanford, R. E., et al., In Vitro Cellular and Devel Biol, 25 (2):174 (1989).
Larrick, J. W. and Fry, K., Huam Antibod Hybrid, 2:172 (1991).
Maniatis, T., et al. *Molecular Cloning: A Laboratory Manual*, Cold Spring Harbor Laboratory (1982).
Saiki, R. K., et al., Science, 239:487 (1988).
Seto, B., et al., Lancet, 11:941 (1984).
Sreenivasan, M. A., et al., J. Gen. Virol., 65:1005 (1984).
Tabor, E., et al., J. Infect. Dis., 140:789 (1979).
Tam, A., et al., Virology, 185:120 (1991).
Yarbough, P. O., J. Virology, 65(11):5790 (1991).
Zola, H., *Monoclonal Antibodies: A Manual of Techniques*, CRC Press, Boca Raton, La., 1987.

BACKGROUND OF THE INVENTION

Enterically transmitted non-A/non-B hepatitis viral agent (ET-NANB, also referred to herein as hepatitis E virus or HEV) is the reported cause of hepatitis in several epidemics and sporadic cases in Asia, Africa, Europe, Mexico, and the Indian subcontinent. Infection is caused usually by water contaminated with feces, although the virus may also spread by close physical contact. The virus does not seem to cause chronic infection.

The viral etiology in HEV has been demonstrated by infection of volunteers with pooled fecal isolates; immune electron microscopy (IEM) studies have shown virus particles with 27–34 nm diameters in stools from infected individuals. The virus particles reacted with antibodies in serum from infected individuals from geographically distinct regions, suggesting that a single viral agent or class is responsible for the majority of HEV hepatitis seen worldwide. No antibody reaction was seen in serum from individuals infected with parenterally transmitted NANB virus (also known as hepatitis C virus or HCV), indicating a different specificity between the two NANB types.

In addition to serological differences, the two types of NANB infection show distinct clinical differences. HEV is characteristically an acute infection, often associated with fever and arthralgia, and with portal inflammation and associated bile stasis in liver biopsy specimens (Arankalle). Symptoms are usually resolved within six weeks. HCV, by contrast, produces a chronic infection in about 50% of the cases. Fever and arthralgia are rarely seen, and inflammation has a predominantly parenchymal distribution (Khuroo, 1980).

The course of HEV is generally uneventful in healthy individuals, and the vast majority of those infected recover without the chronic sequelae seen with HCV. One peculiar epidemiologic feature of this disease, however, is the markedly high mortality observed in pregnant women; this is reported in numerous studies to be on the order of 10–20%. This finding has been seen in a number of epidemiologic studies but at present remains unexplained. Whether this reflects viral pathogenicity, the lethal consequence of the interaction of virus and immune suppressed (pregnant) host, or a reflection of the debilitated prenatal health of a susceptible malnourished population remains to be clarified.

The two viral agents can also be distinguished on the basis of primate host susceptibility. HEV, but not HCV, can be transmitted to cynomolgus monkeys. HCV is more readily transmitted to chimpanzees than is HEV (Bradley, 1987).

In the earlier-filed parent applications, HEV clones, and the sequence of the entire HEV genome sequence were disclosed. From HEV clones, recombinant peptides derived from HEV genomic coding region were produced.

SUMMARY OF THE INVENTION

In one aspect, the invention includes an immunogenic hepatitis E virus (HEV) peptide which has one of the peptides sequences identified by SEQ. I.D. NOS. 23–38.

Specific embodiments include a peptide antigen having a sequence identified by SEQ. I.D. NOS. 23–34, an antigen having a sequence identified by SEQ. I.D. NOS. 35–37, and a peptide antigen having a sequence identified by SEQ. I.D. NO. 38.

In another aspect, the invention includes a diagnostic reagent comprising a solid support, and derivatized thereto, a hepatitis E virus (HEV) peptide antigen which as one of the peptide sequences identified by SEQ. I.D. NOS. 23–38.

Specific embodiments include a reagent in which the peptide antigen has a sequence identified by SEQ. I.D. NOS. 23–34, an antigen having a sequence identified by SEQ. I.D. NOS. 35–37, and a peptide antigen having a sequence identified by SEQ. I.D. NO. 38.

Also forming part of the invention is a vaccine composition for use in immunizing an individual against hepatitis E virus (HEV). The vaccine includes a pharmacologically acceptable carrier, and an HEV peptide antigen which has one of the peptide sequences identified by SEQ. I.D. NOS. 23–38.

Specific embodiments include a composition in which the peptide antigen has a sequence identified by SEQ. I.D. NOS. 23–34, the antigen has a sequence identified by SEQ. I.D. NOS. 35–37, and a peptide having a sequence identified by SEQ. I.D. NO. 38.

The invention further includes an antibody which is immunospecific for a hepatitis E virus (HEV) peptide antigen which has one of the peptide sequences identified by SEQ. I.D. NOS. 23–38.

Specific embodiments include an antibody which is immuoreactive with a peptide antigen which has a sequence identified by SEQ. I.D. NOS. 23–34; with an antigen having a sequence identified by SEQ. I.D. NOS. 35–37, and with an antigen having a sequence identified by SEQ. I.D. NO. 38.

These and other objects and features of the invention will become more fully apparent when the following detailed description of the invention is read in conjunction with the accompanying drawings.

BRIEF DESCRIPTION OF THE DRAWINGS

FIG. 1 shows the HEV genome, the arrangement of open reading frames in the genome, and the approximate coding regions for peptides 406.3-2, GS3, and trpE-C2;

FIG. 4 shows Southern blots of PCR-amplified RNA from non-infected human primary hepatocytes (lane 4) and primary hepatocytes infected with HEV for increasing times from 3 hours to 11 days (lanes 5–11);

FIG. 5 shows Southern blots of PCR-amplified RNA from HEV-infected human primary hepatocytes in which the infective virus is preincubated with normal pre-immune rabbit serum (lanes 1 and 3) or rabbit antiserum against the HEV antigen HEV 406.3-2 (B) (lane 2) and HEV 406.4-2 (M) (lane 4);

FIG. 6 shows Southern blots of PCR-amplified RNA from HEV-infected human primary hepatocytes preincubated with normal human serum (lane 1) and one of a number of different HEV-positive immune human sera (lanes 2–12);

FIGS. 7A–7D shows the nucleotide sequences of the HEV ORF2 and ORF3 for Burma (upper line) and Mexico (lower line) strains of HEV;

FIG. 8 shows the amino acid sequences of the ORF3 peptide for Burma (upper line) and Mexico (lower line) strains of HEV;

FIGS. 9A–9B shows the amino acid sequences of the ORF2 protein for the Burma (upper line) and Mexico (lower line) strains of HEV;

FIG. 11 shows the peptide sequences of HEV identified by SEQ. I.D. NOS. 23–38.

DETAILED DESCRIPTION OF THE INVENTION

I. Definitions

Figure 2A:
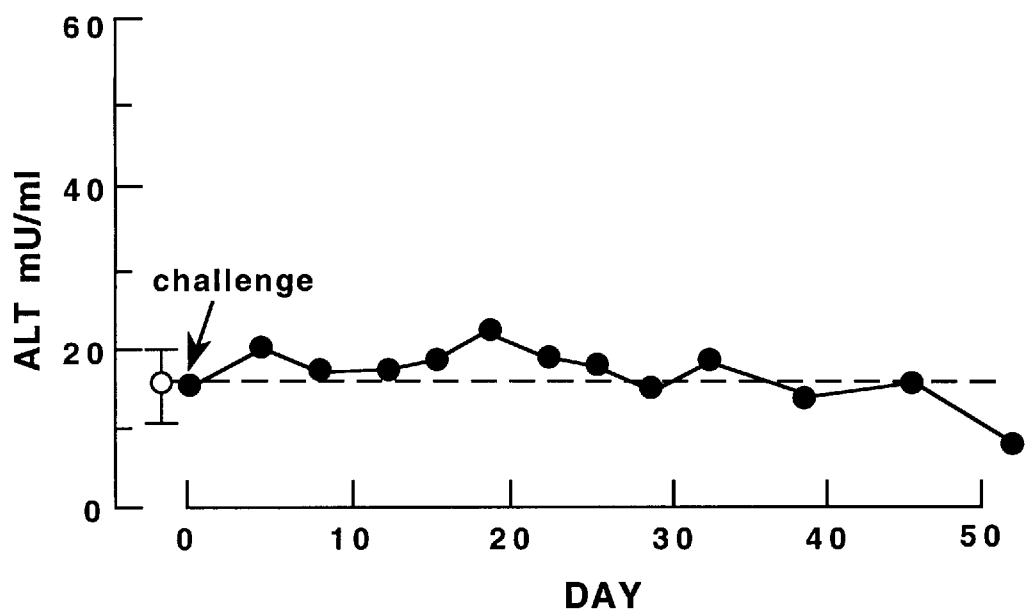
FIGS. 2A and 2B show the blood ALT levels observed after infection of cynomolgus monkeys with a Burma-strain HEV stool sample in animals which were previously immunized with a trpE-C2 HEV antigen (2A) or an alum control (2B)

The terms defined below have the following meaning herein:

1. "Enterically transmitted non-A/non-B hepatitis viral agent", "hepatitis E virus", or "HEV" means a virus, virus type, or virus class which (1) causes water-borne, infectious hepatitis, (ii) is transmissible in cynomolgus monkeys, (iii) is serologically distinct from hepatitis A virus (HAV), hepatitis B virus (HBV), hepatitis C virus (HCV), and hepatitis D virus, and (iv) includes a genomic region which is homologous to the 1.33 kb cDNA insert in plasmid pTZKF1(ET1.1) carried in *E. coli* strain BB4 identified by ATCC deposit number 67717.

2. Two nucleic acid fragments are "homologous" if they are capable of hybridizing to one another under hybridization conditions described in Maniatis et al., op. cit., pp. 320–323. However, using the following wash conditions: 2×SCC, 0.1% SDS, room temperature twice, 30 minutes each; then 2×SCC, 0.1% SDS, 50° C. once, 30 minutes; then 2×SCC, room temperature twice, 10 minutes each, homologous sequences can be identified that contain at most about 25–30% basepair mismatches. More preferably, homologous nucleic acid strands contain 15–25% basepair mismatches, even more preferably 5–15% basepair mismatches. These degrees of homology can be selected by using more stringent wash conditions for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater. See Dayhoff, M. O., in *Atlas of Protein Sequence and Structure* (1972) Vol. 5, National Biomedical Research Foundation, pp. 101–110, and Supplement 2 to this volume, pp. 1–10. The two sequences (or parts thereof, preferably at least 30 amino acids in length) are more preferably homologous if their amino acids are greater than or equal to 50% identical when optimally aligned using the ALIGN program mentioned above.

4. A DNA fragment is "derived from" an HEV viral agent if it has the same or substantially the same basepair sequence as a region of the viral agent genome.

5. A protein or peptide is "derived from" an HEV viral agent if it is encoded by an open reading frame of a DNA or RNA fragment derived from an ET-NANB viral agent.

6. In two or more known peptide sequences which are more than about 70% homologous in amino acid sequence, a third amino acid sequence will be "internally consistent with the known sequences" if each amino acid in the third sequence is identical to at least one of amino acids in the known sequences.

II. HEV Antigen Vaccine

This section describes methods for preparing and using an HEV antigen vaccine effective, when injected intramuscularly (i.m.), to prevent HEV infection.

A. HEV Genomic Sequences

HEV genomic clones, and sequences corresponding to the entire HEV genome for different HEV strains were obtained according to published methods (Tam, Yarbrough) and as described in the parent applications referenced above. Briefly, RNA isolated from the bile of a cynomolgus monkey having a known HEV infection was cloned, as cDNA fragments, to form a fragment library, and the library was screened by differential hybridization to radiolabeled cDNAs from infected and non-infected bile sources.

The basepair sequence of cloned regions of the HEV fragments in identified clones was determined by standard sequencing methods. With reference to FIG. 1, HEV is a virus with an approximately 7.5 kilobase (kb) single-stranded and polyadenylated RNA genome of positive-sense polarity. Three open reading frames (ORFs) have been assigned to HEV as ORF1, encoding polypeptides with domains of the RNA-directed RNA polymerase and a helicase, ORF2, encoding the putative capsid protein of the virus, and ORF3.

The genomic organization of HEV assigns its non-structural gene(s) at the 5' terminus with the structural gene(s) at the 3' end. Two subgenomic polyadenlated transcripts of approximately 2.0 kb and 3.7 kb in sizes are detected in infected liver and co-terminated at their 3' ends with the 7.5 kb full-length genomic transcript. The genomic organization and expression strategy of HEV suggest that it might be the prototype human pathogen for a new class of RNA virus or perhaps a separate genus within the Caliciviridae family.

The genomic and peptide sequences shown in FIG. 7 correspond to the ORF-2 and ORF-3 regions of Burma (B) (upper lines) and Mexico (M) strains (lower lines) of HEV. The bases indicated in the middle lines represent conserved nucleotides. The numbering system used in the comparison is based on the Burma sequence. The Burma sequence has SEQ ID No. 1; and the Mexico sequence, SEQ ID No. 2. The region corresponding to ORF2 has SEQ ID nos. 3 and 4 for the Burma and Mexico strains, respectively. The region corresponding to 406.3-2 has SEQ ID Nos. 5 and 6 for the Burma and Mexico strains, respectively. The region corresponding to SG3 has SEQ ID Nos. 7 and 8 for the Burma and Mexican strains, respectively. The region corresponding to C2 has SEQ ID Nos. 9 and 10 for the Burma and Mexico strains, respectively. The region corresponding to 406.4-2 has SEQ ID Nos. 11 and 12 for the Burma and Mexico strains, respectively.

B. Recombinant Peptide Antigens

The amino acid sequences corresponding to the third and second open reading frames of the Burma and Mexico strains of HEV are given in FIGS. 8 and 9, respectively. The sequence listings shown are as follows:

SEQ ID Nos. 13 and 14 correspond to the amino acid sequences for the peptides 406.3-2 (B) and 406.3-2 (M), respectively. Each peptide is a 42 amino acid peptide in the C-terminal end region of capsid protein encoded by the ORF2, as indicated in the ORF2 sequence (FIG. 9).

SEQ ID Nos. 15 and 16 correspond to the amino acid sequences for the peptides SG3 (B) and SG3 (M), respectively. Each peptide includes the carboxyl 324 amino acids of the HEV capsid.

SEQ ID Nos. 17 and 18 correspond to the amino acid sequences for the peptides C2 (B) and C2 (M), respectively. Each includes the carboxyl 461 amino acids of the HEV protein.

SEQ ID Nos. 19 and 20 correspond to the amino acid sequences for the entire putative capsid protein encoded by the Burma and Mexico strain ORF2, respectively.

SEQ ID Nos. 21 and 22 correspond to the amino acid sequences for the 406.4-2 (B) and 406.4-2 (M), respectively (FIG. 8). These are 33 amino acid sequences encoded by the ORF3.

Also contemplated are sequences which are internally consistent with the above specified sequences from different strains of HEV antigens. These include Sequence ID No. 13; Sequence ID No. 14, and internally consistent variations between Sequence ID Nos. 13 and 14; Sequence ID No. 15; Sequence ID No. 16; and internally consistent variations between Sequence ID Nos. 15 and 16; Sequence ID No. 17; Sequence ID No. 18; and internally consistent variations between Sequence ID Nos. 17 and 18; Sequence ID No. 19; Sequence ID No. 20; internally consistent variations between Sequence ID Nos. 19 and 20.

For example, the HEV 406.3-2 antigens have the sequence homology shown below for the Burma (B) and Mexico (M) strains. The single dots in the sequence comparison indicate recognized high-probability or "neutral" amino acid substitutions. The blank spaces indicate a non-neutral substitution.

```
                                 10                20                30
MEXICAN (SEQ ID NO.17)    ANQP GHL AP LGEI RP S AP P LP P VADLP QP GL RR
                          :: . :.:  ::::  .:: ::::: :..:.::: ::: ::
BURMA (SEQ ID NO.18)      ANP P DHS AP LGVTRP S AP P LP HVVDLP QLGP RR
                                 10                20                30
```

A sequence which is internally consistent with these two sequences would have one of the sequences:(SEQ ID NO:39)

AN(Q/P)P(G/D)H(L/S)APLG(E/V)(I/T)RPSAPPLP(P/H)V(A/V)DLPQ (P/L)G(L/P)RR, where X/Y means either amino acid X or amino acid Y.

The ORF3 amino acid sequences, 124 amino acids in length, for the Burma and Mexico strains have an 87.1% identity in the 124 amino acids. The ORF2 amino acid sequences, having 659 amino acids of overlap, have a 93.0% identity in the 659 amino acids.

To prepare the 406.3-2 (M) peptide, the lambda gt11 406.3-2 described in Example 3 was subcloned into the glutathione S-transferase vector pGEX to express the 3-2 (N) antigen, as detailed in Example 3, and in the Tam reference.

The 406.3-2(B) antigen can be prepared by PCR amplification of the Burma SEQ ID No. 5 from above by PCR amplification of the pBET1 plasmid (Tam). This plasmid contains a 2.3 kb insert covering the ORF2 and ORF3 for Burma strain HEV sequence. The plasmid is amplified by PCR amplification, using a 5' primer containing an NcoI site and a 3' primer containing a BamHI site (Sakai). The amplified fragment is inserted into the NcoI/BamHI site of a pGEX vector, and expressed in an E. coli expression system as described in Example 3.

The SG3(B) peptide was prepared by first amplifying the SEQ ID No. 7 sequence with 5' EcoRI-NcoI and 3' BamHI linkers, using a gt10 phage BET1 clone plasmid containing the entire ORF2 and ORF3 regions of HEV (B). The amplified fragment was inserted into the EcoRI/BamHI site of a Bluescript™ vector (Stratagene, San Diego, Calif.), according to the manufacturer's instructions. After vector propagation and harvesting, the cloned insert was released by digestion with NcoI and BamHI, and gel purified. The purified fragment was inserted into the NcoI/BamHI site of a pGEX vector, and expressed in an E. coli expression system as described in Example 3. The SG3(M) peptide can be prepared similarly, using the SEQ ID No. 8 in place of the SEQ ID No. 7.

The C2 (B) peptide is prepared as described in Example 5. Briefly, a gt10 phage BET1 plasmid was digested with EcoRI to release the SEQ ID No. 10 C2 sequence, and this fragment was inserted into a pATH10 trpE fusion vector, and the recombinant fusion protein expressed in an E. coli host.

The C2 (M) peptide can be prepared, substantially as described above, by PCR amplification of the SEQ ID No. 10, using a 5' primer containing an EcoRI site and a 3' primer containing a BamHI site. The amplified fragment is inserted into the EcoRI/BamHI site of a pGEX vector, and expressed in an E. coli expression system as described in Example 3.

The capsid protein (B) was prepared substantially as described above by PCR amplification of the SEQ ID No. 3, from a gt10 BET1 plasmid using a 5' primer containing an NcoI site and a 3' primer containing a BamHI site. The amplified fragment was inserted into the NcoI/BamHI site of a pGEX vector, and expressed in an E. coli expression system as described in Example 3. The capsid protein (M) is similarly prepared.

To prepare the 406.4-2 (M) peptide, the lambda gt11 406.4-2 described in Example 3 was subcloned into the glutathione S-transferase vector pGEX to express the 3-2 (M) antigen, as detailed in Example 3.

The 406.4-2(B) antigen can be prepared by PCR amplification of the Burma SEQ ID No. 11 from above by PCR amplification, using a 5' primer containing an NcoI site and a 3' primer containing a BamHI site. The amplified fragments is inserted into the NcoI/BamHI site of a pGEX vector, and expressed in an E. coli expression system as described in Example 3.

It will be appreciated that other HEV peptides containing selected portions, and preferably C-terminal portions of the HEV capsid protein containing the 406.3-2 sequence, can similarly be prepared, using the HEV genomic-insert plasmids above, with amplification of the desired sequences and cloning into a suitable expression vector, as outlined above, and detailed in Examples 3 and 5.

The coding sequences used in producing the recombinant peptides can be derived from the cloning vectors described above and detailed elsewhere (Tam), or from synthetic nucleotide synthesis using PCR slicing methods to join oligonucleotide fragments, according to known methods, in building up nucleotide sequences.

C. Mature Capsid Protein

HEV peptide antigens may also be obtained from purified HEV virus propagated in primary hepatocytes obtained from primate liver, preferably from human or cynomolgus monkey liver. Methods for preparing primary primate hepatocytes for culture, and culture medium conditions effective to preserve liver-specific functions for extended periods in culture are detailed for human hepatocytes in Example 1 below.

After 3 days of growth in culture, the cells are infected with a pooled inoculum of HEV-infected cynomolgus monkey stool pool (fourth passage), as detailed in Example 2. The presence and level of propagating HEV virus in the cells can be measured by indirect immunoflourescence. Where, for example, the primary cells are cynomolgus cells, the cells can be immunoreacted with human HEV anti-sera, followed by immunoreaction with rabbit anti-human IgG antibodies.

Alternatively, the HEV virus can be detected and measured by selective amplification methods involving initial cDNA formation, and PCR amplification of HEV cDNA sequences by PCR amplification, as detailed in Example 2.

Virus particles can be isolated from HEV infected human hepatocytes in culture medium by pelleing the virus through a 30% sucrose cushion by ultracentrifugation. The pelleted virus may be further purified, if desired, by zonal centrifugation through a 10–40% sucrose gradient, combining peak virus fractions.

Other methods for separating virus particles from soluble culture-medium components may be used. For example, clarified culture medium can be passed through a size-exclusion matrix, to separate soluble components by size exclusion.

Alternatively, the clarified culture medium can be passed through an ultrafiltration membrane having a 10–20 nm pore size capable of retaining virus particles, but passing solute (non-particulate) culture medium components.

The present invention allows glycosylation and other post-translation modifications in intact HEV capsid protein. Capsid isolation from the viral particles can be carried out by standard methods, such as ion exchange and size-exclusion chromatography, and HPLC purification, after solubilization of the virus particles in a solubilizing medium, such as a solution of a non-ionic surfactant. The protein may be purified by affinity chromatography, employing, for example, antibodies purified from anti-HEV antisera.

D. Preparation of Vaccine Compositions

The recombinant or intact HEV capsid or capsid fragment peptides (HEV capsid antigens) described above are incorporated into a vaccine composition, according to known procedures, to enhance the antigenicity of the injected antigens.

In one composition, the HEV antigen is covalently coupled to a carrier protein, such as keyhole limpet hemocyanin, and injected either in solution form or in combination with an adjuvant. Alternatively, where the HEV antigen is prepared as part of a fusion protein, the non-HEV moiety of the protein may serve as the carrier protein. The derivatized or fusion protein is carried in a pharmaceutically acceptable carrier, such as in solution or in an adjuvant, such as converted alum.

Alternatively, the free peptide itself, e.g., the HEV C2 peptide, may be formulated in alum or used without adjuvant. A suitable adjuvanted vaccine has a preferred antigen concentration of about 1 mg peptide antigen/mg alum, and not to exceed 80 mg of alum per injection.

III. Antigen Vaccine Method

In a related aspect, the invention is directed to a method of inhibiting infection of an individual by hepatitis E virus, by administering to the subject, by parenteral injection, e.g., intramuscular or intravenous injection, the vaccine composition of the invention.

Preferred vaccine compositions, for use in the method are those in which the HEV antigen includes the sequence in the peptides identified by:

Sequence ID No. 13; Sequence ID No. 14, and internally consistent variations between Sequence ID Nos. 13 and 14; Sequence ID No. 15; Sequence ID No. 16; and internally consistent variations between Sequence ID Nos. 15 and 16; Sequence ID No. 17; Sequence ID No. 18; and internally consistent variations between Sequence ID Nos. 17 and 18; Sequence ID No. 19; Sequence ID No. 20; internally consistent variations between Sequence ID Nos. 19 and 20.

The antigen vaccine composition is preferably administered intramuscularly in a series of innoculations, for example, two-three injections given at four week intervals.

In the method detailed in Example 7, cynomolgus monkeys were injected i.m. with the C2 fusion protein trpE-C2 (B), formulated in a converted alum adjuvant or with no adjuvant. Four animals received the alum plus trpE-C2 (B) antigen in two injections, spaced one month apart. Two other animals received alum only on the same vaccination schedule. None of the animals showed the presence of any anti-HEV serum antibody 4 weeks after the second injection, as judged by Western blotting using a fusionless C2 HEV antigen or by a separate fluorescence antibody blocking assay.

At this stage, two of the four experimental animals received a third innoculation of non-adjuvanted, insoluble trpE-C2 peptide antigen. Four weeks later, these animals showed anti-HEV antibodies, as evidenced by Western blots. These results suggest that the trpE-C2 antigen may be more effective when administered in the absence of alum, possibly because of alum-denaturation of the antigen during the alum co-precipitation procedure.

One month after the final innoculation, the animals were challenged with an intravenous injection of a third-passage human stool previously shown to be highly infectious for HEV (Burma strain) or with a Mexico-strain human HEV stool sample. At selected intervals after innoculation, serum samples from the animals were used to measure ALT (alanine transferase) levels, as an indication of necrosis and hepatocellular degradation. Liver biospy samples were also assayed for the presence of HEV antigens by a direct fluorescent antibody assay (FA).

FIG. 2A shows the change in liver ALT levels period following infection with Burma-strain HEV virus, in one of the animals which received a third dose of trpE-C2. As seen, there was no evidence of elevated ALT levels in the 7 and ½ week period following infection. The liver biopsy samples also showed no evidence of HEV antigen.

Figure 2B:
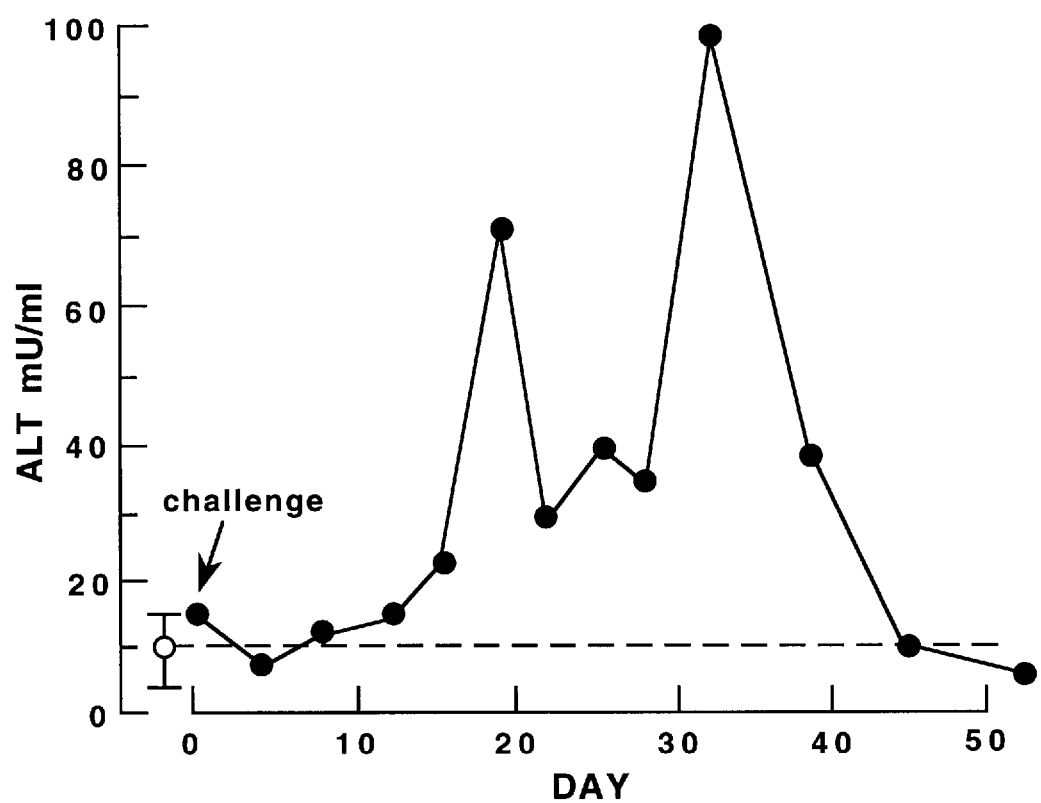

FIG. 2B shows ALT levels measured after HEV (B) infection of a control animal (alum alone injections) which was infected intravenously with the Burma strain HEV. The elevated ALT levels indicate the level of infection which is expected in the absence of vaccine protection. HEV antigen was also detected in the liver biopsy samples. A similar result was observed in the animal which received two injections of trpE-C2 alum composition, but not the third alum-free vaccination, as described above.

Figure 3A:
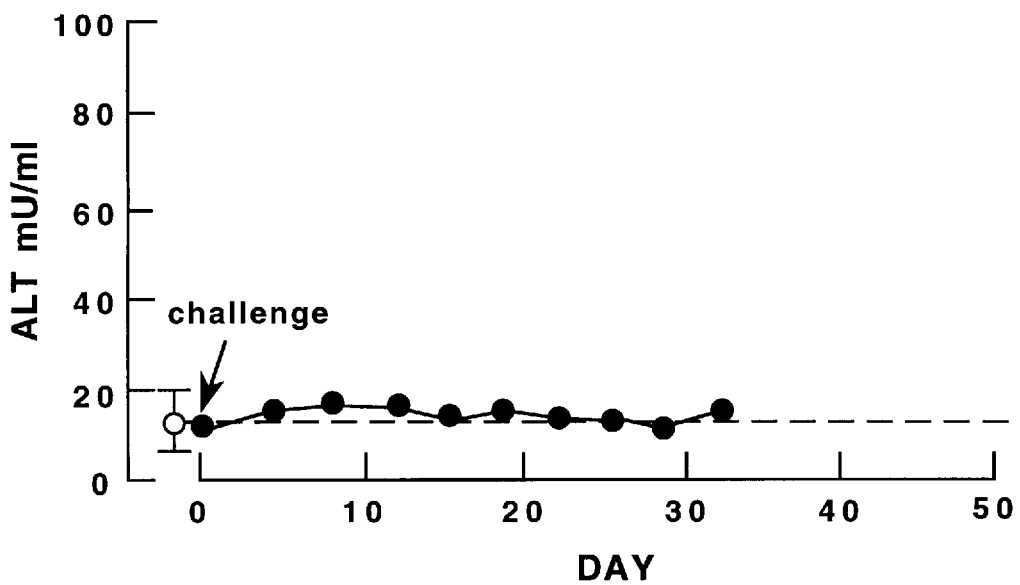
FIGS. 3A and 3B show the blood ALT levels observed after infection of cynomolgus monkeys with a Mexico-strain HEV stool sample in animals which were previously immunized with the trpE-C2 HEV antigen (3A) or an alum control (3B)

FIG. 3A shows the change in liver ALT levels following infection with Mexico-strain HEV virus, in one of the animals which received a third dose of trpE-C2. Again, there was no evidence of elevated ALT levels out to day 32 (The animal died of unrelated causes at day 32). The liver biopsy samples also showed minimal evidence of HEV antigen. This result demonstrates that an antigen vaccine directed against one HEV strain can provide protective immunity against other HEV strains.

Figure 3B:
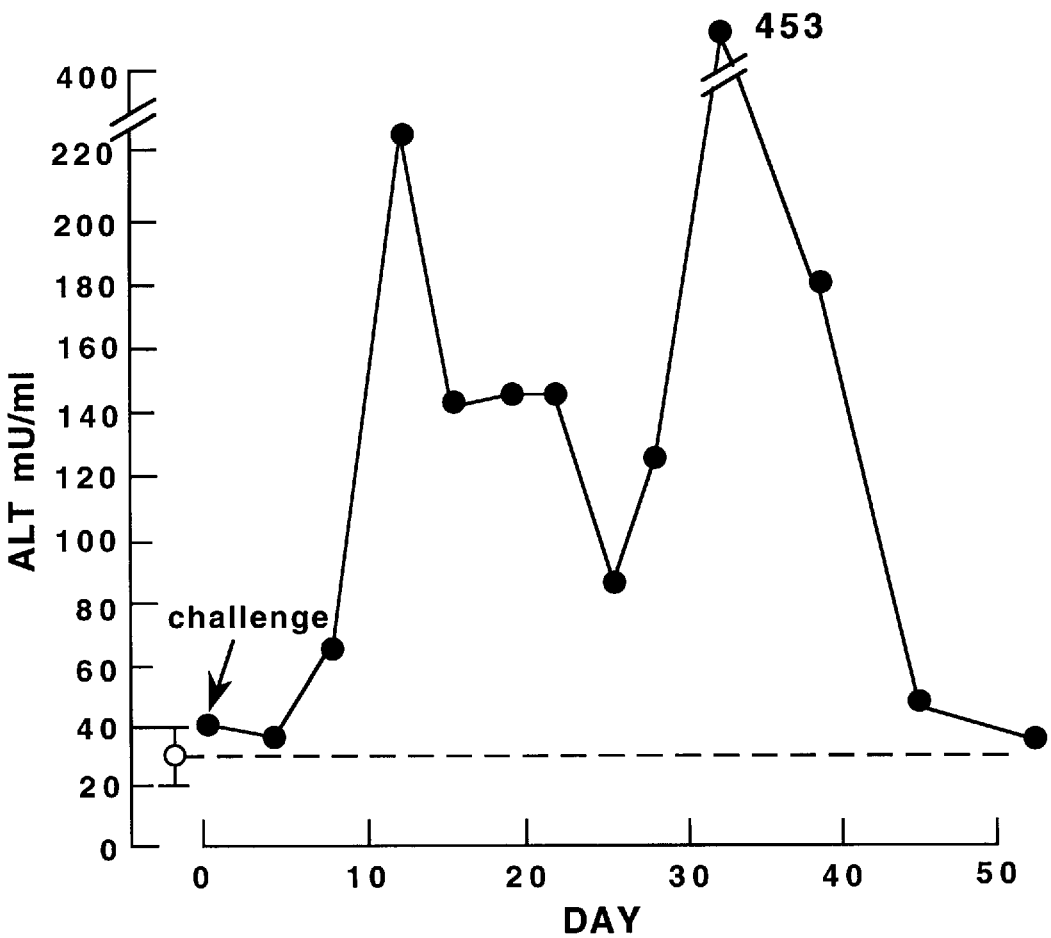

FIG. 3B shows ALT levels measured after HEV infection of a control animal (alum alone injections) which was infected intravenously with the Mexico strain of HEV. High levels of infection (ALT activity) were observed. A similar result was observed in the animal which received two injections of trpE-C2 alum composition, but not the third alum-free vaccination, as described above.

Details of the vaccination method just reported are given in Example 5.

IV. Vaccine Composition

In another aspect, the invention includes an antibody vaccine composition effective in neutralizing HEV infection, as evidenced by the ability of the composition to block HEV infection in HEV-infectable primary hepatocytes in culture. Two exemplary primary cells are human and cynomolgus monkey cells.

The antibodies in the composition are preferably immunoreactive with a peptide containing one of the sequences: Sequence ID No. 13; Sequence ID No. 14, and internally consistent variations between Sequence ID Nos. 13 and 14. As will be seen below, antibodies prepared against the 406.3-2 antigen (M) are effective to block HEV infection in human primary hepatocytes.

Antibodies which are immunoreactive with larger capsid peptides or proteins containing the carboxy terminal of SEQ ID No. 13 or 14 are also preferred. These may include, specifically Sequence ID No. 15; Sequence ID No. 16; and internally consistent variations between Sequence ID Nos. 15 and 16. As will be seen below, human sera which are effective to prevent HEV infection of human primary hepatocyes are immunoreactive with the SG3 peptides defined by these sequences.

Antibodies which are immunoreactive with the trpE-C2 peptides defined by Sequence ID No. 17; Sequence ID No. 18; and internally consistent variations between Sequence ID Nos. 17 and 18 are also preferred, as are antibodies immunoreactive with the entire capsid protein, as defined by Sequence ID No. 19; Sequence ID No. 20; internally consistent variations between Sequence ID Nos. 19 and 20.

The antibodies may be obtained as polyclonal antibodies from antisera, prepared for example, by immunization of a suitable animal, such as a rabbit or goat, with one of the HEV antigens specified above. Alternatively, polyclonal antibodies may be obtained from human or other primate HEV antisera. Anti-HEV polyclonal antibodies from the antisera may be purified or partially purified according to standard methods, such as used to obtain partially purified serum IgG fractions (see, e.g., *Antibodies: A laboratory Manual*, 1988, Cold Springs Harbor Lab). Alternatively anti-HEV antibodies can be obtained in purified form by affinity chromatography, employing a solid support derivatized with one of the capsid antigens described above.

In another embodiment, the antibodies are monoclonal antibodies secreted by hybridoma cell lines. To prepare the hybridoma cell lines, lymphocytes from an immunized animal, preferably mouse or human, are immortalized with a suitable immortalizing fusion partner, according to established methods (e.g., Engleman, Zola).

Alternatively, human monoclonal antibodies may be produced by recombinant methods, in which light and heavy human anti-HEV IgG genes obtained from cultured lymphocytes are inserted into suitable expression vectors, and used to co-infect a suitable host. Methods for obtaining and cloning light and heavy genes from human lymphocytes, and for expressing the cloned genes in a co-infected host cell are known (Larrick).

The anti-HEV antibodies are formulated in a suitable solution for injection, typically by intramuscular, subcutaneous or intravenous route, to form the vaccine composition.

B. Neutralizing Activity of Anti-406.3-2 Antibodies

To demonstrate the neutralizing capability of antibodies prepared as above, antibodies against the 406.3-2 (B) antigen were tested for their abilities to block HEV infection in human primary hepatocytes in culture.

The primary hepatocytes were prepared and cultured according to published procedures and as detailed in Example 1. The unique culture conditions allow for long-term cell growth in culture without loss of specialized hepatocyte function, as evidenced by the cells' continued ability to make and secrete liver-specific proteins, such as serum albumin, up to several months after initial culturing, as described in Example 1.

The cultured cells were innoculated with either normal human sera or a cynomolgus stool preparation. To demonstrate HEV infection in the cells, the cells were examined on days 1–11 after infection for the presence of HEV RNA, using a combination of reverse transcriptase, to form cDNA's, and polymerase chain reaction (PCR) to amplify HEV-specific cDNA. The amplified fragment is expected to have a 551 basepair length. FIG. 4 shows Southern blots of the amplified material, using an HEV ORF2 radiolabled probe for detecting amplified HEV sequence.

The results are shown in FIG. 4. Lanes 1–3 are controls. Lane 4 is total amplified material from cells inoculated with normal (non-infected) sera. Lanes 5–11 show amplified material 3 hours, 1 day, 3 days, 5 days, 7 days, 9 days, and 11 days after infection with the cyno stool sample, respectively. The results show that HEV propagated in human primary hepatocytes within one day after initial infection (lane 6). There was a time-dependent increase at the level of HEV replication up to 5 days post infection (lanes 7 and 8), which appeared to decrease thereafter (lanes 9–11). There was no evidence of HEV in total cellular RNA isolated from uninfected primary cells.

Rabbit antisera against antigen peptides 406.3-2 (B) and 406.4-2 (M) and 406.4-2 (B) were prepared. As noted above, the 406.3-2 peptide is from the carboxy terminal end region of the HEV capsid protein, and the 406.4-2 peptide, from the peptide encoded by the HEV ORF3. Preimmune rabbit serum or rabbit antiserum against one of HEV antigens was added to the cyno stool inoculum, at a 1:20 dilution, and the antibody was incubated with the viral preparation. The antibody-treated stool sample was then used to infect human primary hepatocytes. 14 days later, the cells were examined for HEV infection by the RT/PCR/Southern blot method just described, except employing primers which are expected to yield a 448 basepair amplified fragment.

The results are shown in FIG. 5. Lanes 1 and 3 in this figure show amplified RNA from cells infected with cyno stool sample previously incubated with human preimmune serum. The 448 basepair band in the figure indicates HEV infection. The second lane corresponds to cells which were exposed to anti-406.3-2 (B) rabbit antisera, and indicates virtually complete absence of HEV infection. Lane 4 shows amplified material from cells exposed to anti-406.4-2 (M) rabbit antisera. The antibody showed little or no protective effect against HEV infection.

C. Neutralizing HEV Antisera

Another source of neutralizing antibodies, in accordance with the invention, is human HEV antisera which is characterized by immunospecific reaction to the 406.3-2 antigen and the SG3 antigen, both described above.

To examine the neutralizing antibody characteristics of human HEV antisera, a panel of human antisera were tested for the ability to block HEV infection of cultured hepatocytes, substantially as described above. The ten HEV positive human antisera are shown in Table 1 below, and are from patients who developed HEV infection in India, Pakistan, and Mexico. The antisera were not tested for strain type.

Briefly, cultured cells were exposed to HEV-positive cyno stool treated with samel (Burma strain) treated with normal pooled serum or HEV antiserum, and tested for the presence of HEV-specific nucleic acid sequences, by PCR amplification and Southern blotting with an HEV radiolabled probe. The Southern blots are shown in FIG. 6. The lane numbers of the 12 serum samples are given in parentheses in Table 1 below. As seen from FIG. 6, and indicated in Table 1, the antisera which were effective in neutralizing HEV were India 10 (lane 2), India 18 (lane 3), India 210 (lane 5), India 265 (lane 8), Pak 143 (lane 9), and Pak 336 (lane 10). Other human sera, however, showed very little (lane 11, Mex 387C) or no effect (lane 4, India 29; lane 6, India 242; lane 7, India 259; lane 12, Mex 387C[IgG]) in their ability to neutralize HEV infection. As a negative control, the normal human serum pool revealed absolutely no neutralizing activity against HEV (lane 1).

TABLE 1

| Serum | Clinical | Neutralizing Activity |
|---|---|---|
| normal (1) | pooled | – |
| India 10 (2) | – | + |
| India 18 (3) | acute, import | + |
| India 29 (4) | acute, import | – |
| India 210 (5) | acute | + |
| India 242 (6) | acute, fulminant | – |
| India 259 (7) | acute, fulminant | – |
| India 265 (8) | acute | + |
| Pak 143 (9) | acute | + |
| Pak 336 (10) | acute | + |
| Mexico F387c (11) | convalescent | – |
| Mexico F387c (IgG) (12) | convalescent | – |

Several of the human antisera were tested for their IgG and IgM immunoreactivity to 406.3-2 (M), 406.4-2 (M) and 406.4-2 (B) antigens noted above. Reaction with IgM antibodies tends to indicate early-phase infection, whereas immunoreactivity with IgG is indicative of both early and later stages of infection. Reaction was measured in an ELISA test. The results are shown in Table 2A and 2B, where a "+" sign indicates a positive reaction; numbers in the table indicate dilution titre of IgG against the specific recombinant protein indicated.

TABLE 1A

| Serum Samples | IgG | | | Neutralizing Activity | Clinical |
|---|---|---|---|---|---|
| | 406.3-2 (M) | 406.4-2(B) | 406.4-2(M) | | |
| Normal Human | – | – | – | – | Pooled Human Serum |
| India 18 | + | + | + | + | acute, import |
| India 29 | – | + | – | – | acute, import |
| India 210 | + | + | + | + | acute |
| India 242 | + | + | + | – | acute, fulminant |
| India 259 | + (500) | + (>5000) | + (2000) | – | acute, fulminant |
| India 265 | + (>5000) | + (>5000) | + (1000) | + | acute |

TABLE 1B

| Serum Samples | IgM | | |
|---|---|---|---|
| | 406.3-2(M) | 406.4-2(B) | 406.4-2(M) |
| Normal Human | ND | ND | ND |
| India 18 | – | – | – |
| India 29 | – | – | – |
| India 210 | – | – | – |
| India 242 | + | + | – |
| India 259 | + | + | – |
| India 265 | + | + | – |

The data from the table indicates that those human antisera capable of neutralizing were positive by an IgG ELISA for antibodies to the HEV 3-2(M) epitope. India 29 was not positive for IgG(s) to HEV 3-2(M) and did not neutralize HEV infection (lane 4). Although India 242 and India 259 were positive for IgG(s) to HEV 406.3-2(M), they were also positive for IgM to HEV 406.3-2(M), which is indicative of an early stage HEV infection. Therefore in these particular samples, the levels of IgG(s) to HEV 3-2(M) elicited might be sufficient to neutralize HEV infection of primary human hepatocytes.

To further study the correlation of neutralizing activities of sera of HEV-infected humans with immunoreactivities to HEV3-2 epitope, Western blotting analyses were performed on these human serum samples, with the results shown in Table 3. As seen in this table, India 18, India 265, and especially India 210, previously shown to be neutralizing for HEV infection, were immunoreactive to HEV406.3-2(M) in these Western blotting analyses and their immunoreactivities correlated with their neutralizing activities.

As a confirmation for the specific immunoreactivities of these sera to HEV406.3-2(M), Western analyses were performed against the fusion protein SG3 (B), which contains the 329 carboxy-terminal amino acids (nucleotides 6146–7129) of ORF-2 of HEV Burma strain. The immunoreactivities of these sera against HEV406.3-2(M) and SG3 [or HEV406.3-2(B)] were perfectly matched (Table 3).

TABLE 3

| Serum Samples | 406.3-2(M) ELISA Titre | 406.3-2(M) Western Blot | SG3 Western Blot | Neutralizing Activity |
|---|---|---|---|---|
| Normal Human | – | – | – | – |
| India 18 | 2000 | ++ | + | + |
| India 29 | – | – | – | – |
| India 210 | 100 | ++ | + | + |
| India 242 | 500 | – | – | – |
| India 259 | 500 | ± | – | – |
| India 265 | 5000 | +++ | +++ | + |

Thus, human HEV antisera which provide a suitable source of neutralizing antibodies are those characterized by (a) immunoreactivity with a 406.3-2 antigen, and (b) the SG3 antigen, both as evidenced by immunoreactivity in a Western blot, i.e., where the antigen is in an exposed, accessible configuration.

More generally, a preferred vaccine composition of the invention contains antibodies immunospecific against the 406.3-2 antigenic and against the SG3 antigenic peptide. The vaccine composition includes the immunospecific antibodies in a suitable carrier for parenteral injection.

The antibody vaccine composition is used, according to another aspect of the invention, for preventing or treating HEV infection in humans.

V. HEV EDitopic Antigens

This section describes HEV peptide antigen which are derived from HEV regions encoded by ORF1, ORF2, and ORF3 open reading frame regions of the HEV (Burma strain) genome. The three open reading frames of the genome were used to determine overlapping peptide sequences. Peptides having these sequences were constructed as described in Example 6A.

The overlapping antigens from the three ORF's were immunoscreened with pooled HEV antisera (Example 6B). Pooled sera from patients with acute HEV were termed "reactive" with a particular peptide only if (i) the optical density resulting from the interaction of the sera and the peptide was at least 3-fold higher than the interaction of the same peptide with the pooled control sera, and (ii) the peptide was adjacent to at least one other peptide that met the same criterion. Since adjacent peptides overlapped by four amino acids, significant reactivity directed against two adjacent peptides strongly suggests the presence of an epitope that is common to both peptides.

Figure 10A:
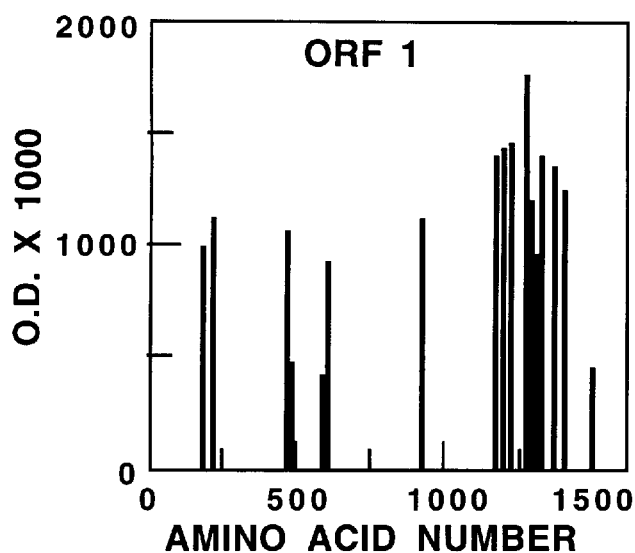
FIGS. 10A–10C are graphical representations of reactive epitopes encoded by the ORF1 (10A), ORF2 (10B), and ORF3 (10C)
Figure 10B:
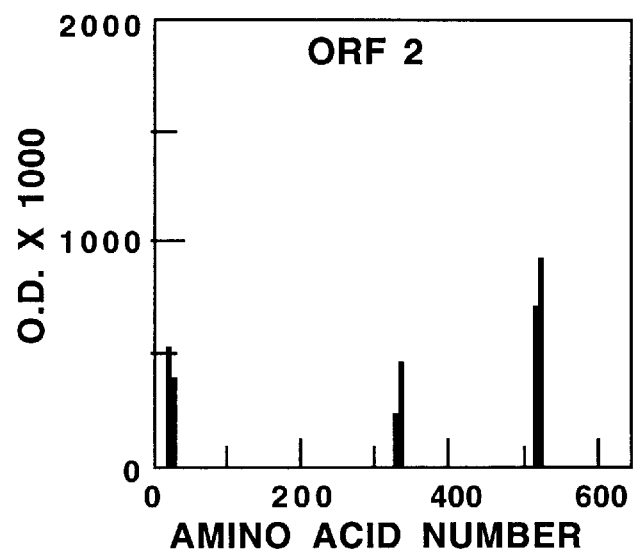
Figure 10C:
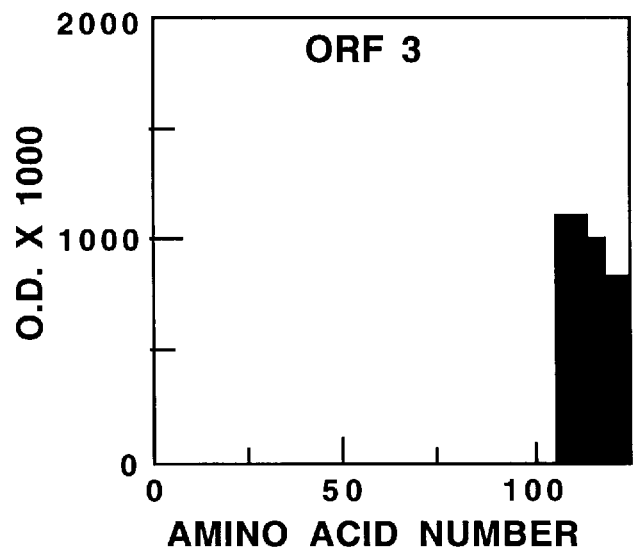

FIGS. 10A to 10C depict the optical densities at 405 nm obtained for the reactive peptides of one of the duplicate syntheses. Reactivity with antibodies is localized to epitopes contained within 12 discreet regions (FIG. 10A), identified by peptides sequences SEQ. I.D. NOS. 23–34, to three discreet of the presumed structural protein encoded by ORF2 (FIG. 10B), these regions being identified by peptide sequences SEQ. I.D. NOS. 35–37, and to one discrete region of the presumed protein encoded by ORF3 (FIG. 10C), this region being identified by peptide sequence SEQ. I.D. NO. 38.

Figure 12A:
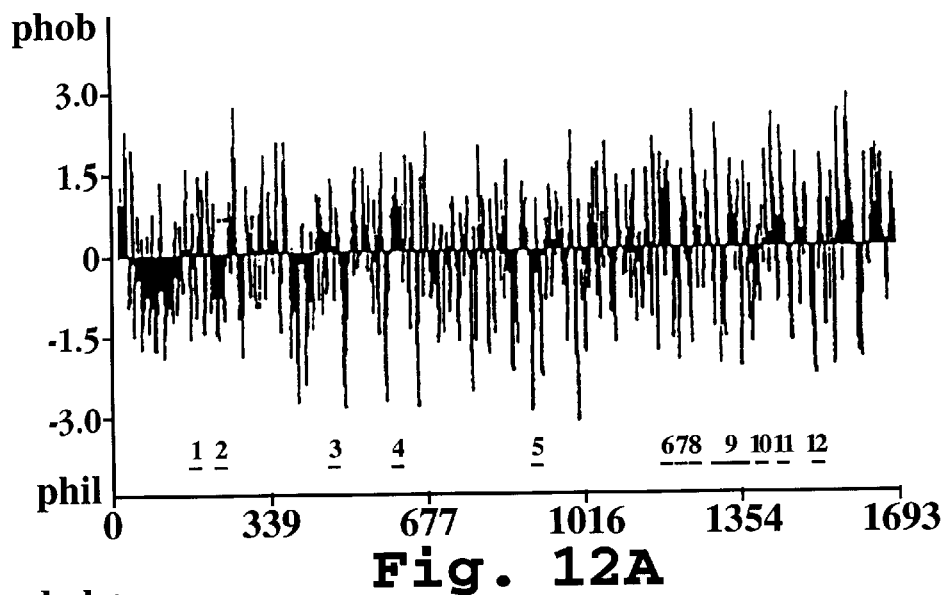
FIGS. 12A–12C are hydropathy profiles of proteins encoded by HEV ORF1 (12A), ORF2 (12B), and ORF3 (12C), where positive values on the ordinate indicate hydrophobicity and negative values indicate hydrophilicity.
Figure 12B:
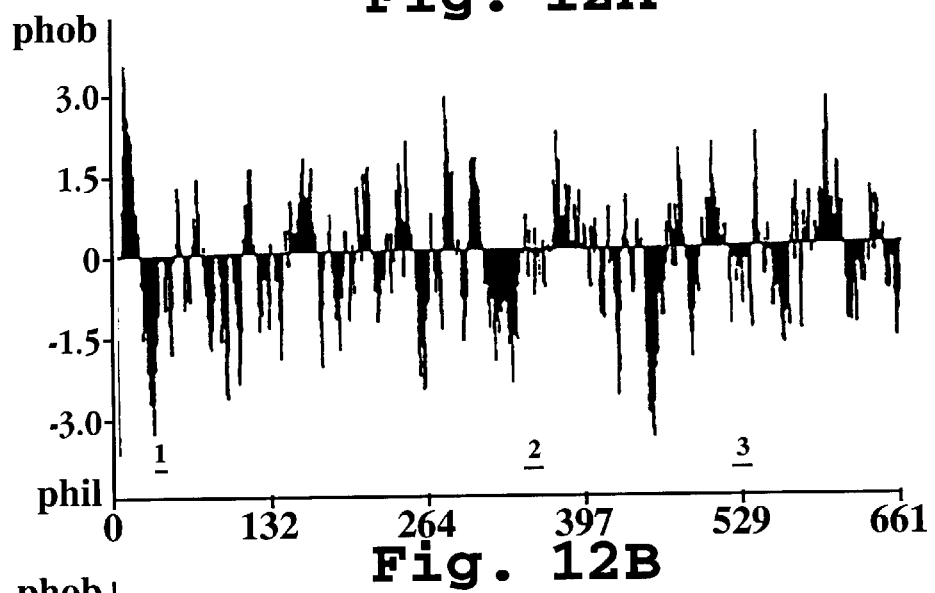
Figure 12C:
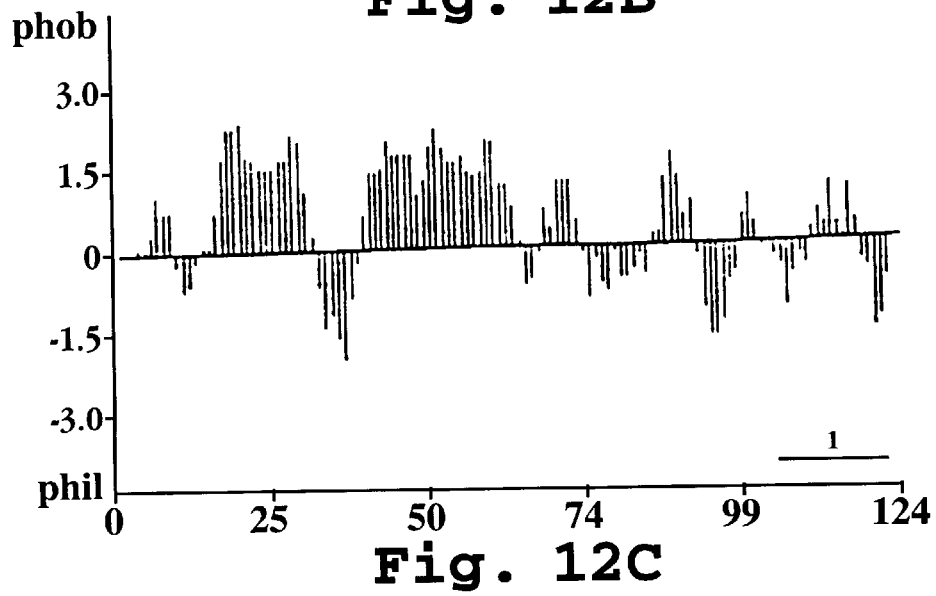

The hydropathy profiles (Kyte) of the proteins encoded by each of the three ORFs is shown in FIGS. 12A–12C for ORF1-)RF3, respectively. Analysis of each of the sixteen region shown in FIG. 11 (SEQ I.D. NOS. 23–38) indicates that each region contains at least 1 hydrophilic locus.

A. Immunogenic HEV Peptides

In one aspect, the invention includes HEV peptide antigens having the one of the sequences identified in FIG. 11 SEQ I.D. NOS 23–38. The peptide antigens derived from ORF1 are identified by the sequences with SEQ I.D. NOS. 23–34. The peptide antigens derived from ORF2 are identified by the sequences with SEQ I.D. NOS. 35–37. The peptide antigen derived from ORF3 is identified by the sequence with SEQ I.D. NO. 38. These peptides may be produced by conventional solid-phase synthesis methods or recombinant methods, and may include other peptide or protein conjugates or moieties, as as would be formed recombinantly in a fusion protein.

B. Diagnostic Reagent

One general diagnostic test for determination of HEV, in accordance with the present invention, is an enzyme-immunoassay for screening human sera for HEV infection. In this assay format, a solid phase reagent having surface-bound HEV peptide antigens, containing peptides whose sequences are identified by SEQ I.D. NOS. 23–38 is reacted with analyte serum, under conditions which allow antibody binding to the peptide on the reagent. After washing the reagent to remove unbound serum components, the reagent is reacted with an enzyme-labeled anti-human antibody, to bind enzyme to the reagent in proportion to the amount of bound anti-HEV antibody on the solid support. The reagent is again washed, to remove unbound antibody, and the amount of enzyme associated with the reagent is determined. One exemplary method employs an anti-human antibody labeled with alkaline phosphatase.

The enzyme-labeled antibody, and reagents required for enzyme detection, are also referred to herein as reporter means for detecting the presence of human antibody bound to the peptide antigen on the solid support.

The solid surface reagent in the above assay is prepared by known techniques for attaching protein material to solid support material, such as polymeric beads, dip sticks, or filter material. These attachment methods generally include non-specific adsorption of the protein to the support or the covalent attachment of the protein, typically through a free amine group, to a chemically reactive group on the solid support, such as an activated carboxyl, hydroxyl, or aldehyde group.

C. Peptide Vaccine Compositions

Also included in the invention is a vaccine composition containing an HEV peptide antigen identified by one of the above sequences SEQ I.D. NOS. 23–38, and preferably also containing an immunogenic peptide carrier to which the peptide is bound.

Particularly useful immunogenic carriers for the peptide (s) include keyhole limpet hemocyanin (KLH), tetanus toxoid, poly-1-(Lys:Glu), peanut agglutinin, poly-D-lysine, diphtheria toxoid, ovalbumin, soybean agglutinin, bovine serum albumin (BSA), human serum albumin, and the like.

The immunogenic peptide(s) may be conjugated to the carrier by a variety of known methods, including chemical derivatization and by genetic engineering techniques. Such latter technique is disclosed in more detail by Gerald Quinnan, "Proceedings of a Workshop," Nov. 13–14, 1984. Vaccines and inocula of the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the mammal to be immunized, the carrier when used, the adjuvant when used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

In any event, the immunogen contained in a vaccine or an inoculum is present in an "effective amount," which amount depends upon a variety of factors as is well known in the immunological arts, e.g., the body weight of the mammal to be immunized, the carrier moiety used, the adjuvant used, the duration of protection sought, and the desired immunization protocol.

D. Anti-HEV Antibodies

In another aspect, the invention includes an antibody composition effective in neutralizing HEV infection, as evidenced by the ability of the composition to block HEV infection in HEV-infectable primary hepatocytes in culture.

The antibodies contemplated herein are those which are immuoreactive with an HEV peptide sequence identified by SEQ I.D. NOS 23–38. In one embodiment, the antibodies are preferably immunoreactive with a peptide containing one of the sequences SEQ I.D. NOS 23–34; in another embodiment, with a peptide containing one of the sequences SEQ I.D. NOS 35–37; in a third embodiment, with a peptide sequence SEQ I.D. NO. 38.

The antibodies may be obtained as polyclonal antibodies from antisera, prepared for example, by immunization of a suitable animal, such as a rabbit or goat, with one of the HEV antigens specified above. Alternatively, polyclonal antibodies may be obtained from human or other primate HEV antisera. Anti-HEV polyclonal antibodies from the antisera may be purified or partially purified according to standard methods, such as used to obtain partially purified serum IgG fractions (see, e.g., *Antibodies: A laboratory Manual*, 1988, Cold Springs Harbor Lab). Alternatively anti-HEV antibodies can be obtained in purified form by affinity chromatography, employing a solid support derivatized with one of the capsid antigens described above.

In another embodiment, the antibodies are monoclonal antibodies secreted by hybridoma cell lines. To prepare the hybridoma cell lines, lymphocytes from an immunized animal, preferably mouse or human, are immortalized with a suitable immortalizing fusion partner, according to established methods (e.g., Engleman, Zola).

Alternatively, human monoclonal antibodies may be produced by recombinant methods, in which light and heavy human anti-HEV IgG genes obtained from cultured lymphocytes are inserted into suitable expression vectors, and used to co-infect a suitable host. Methods for obtaining and cloning light and heavy genes from human lymphocytes, and for expressing the cloned genes in a co-infected host cell are known (Larrick).

The anti-HEV antibodies are formulated in a suitable solution for injection, typically by intramuscular, subcutaneous or intravenous route, to form the vaccine composition.

The following examples, which illustrate various methods and compositions in the invention, are intended to illustrate, but not limit the scope of the invention.

Materials

Enzymes: DNAse I and alkaline phosphatase were obtained from Boehringer Mannheim Biochemicals (BMB, Indianapolis, Ind.); EcoRI, EcoRI methylase, DNA ligase, and DNA Polymerase I, from New England Biolabs (NEB, Beverly Mass.); and RNase A was obtained from Sigma (St. Louis, Mo.).

Other reagents: EcoRI linkers were obtained from NEB; and nitro blue tetrazolium (NBT), S-bromo-4-chloro-3-indolyl phosphate (BCIP) S-bromo-4-chloro-3-indolyl-B-D-galactopyranoside (Xgal) and isopropyl B-D-thiogalactopyranoside (IPTG) were obtained from Sigma. cDNA synthesis kit and random priming labeling kits are available from Boehringer-Mannheim Biochemical (BMB, Indianapolis, Ind.).

EXAMPLE 1

Human Primary Hepatocytes in Culture

A. Isolation of hepatocytes

Hepatocytes were isolated from human liver obtained from Stanford University Medical Center. The liver was either perfused in situ or excised as a wedge for perfusion in laboratory. The initial perfusion was performed for 10 minutes at 60 ml/min using $Ca^{++}$-, $Mg^{++}$-free Hanks' balanced salt solution supplemented with 10 mM HEPES (pH7.4) and 0.5 mM [ethylene bis(oxyethylenenitrillo]-tetraacetic acid. Perfusion was continued for additional 20 minutes using Williams' medium E (WME) supplemented with 10 mM HEPES (pH7.4) and 100 U/ml collagenase (type I, Sigma Chemical Co., St. Louis, Mo.).

After perfusion the liver capsule was removed using fine forceps, and hepatocytes were dislodged by gentle shaking in collagenase solution. The hepatocyte suspension was filtered through several layers of gauze and mixed with an equal volume of WMW containing 10% fetal bovine serum (FBS). Hepatocytes were sedimented by centrifugation at 50 Xg for 5 minutes and resuspended in WME containing 5% FBS. Hepatocytes were sedimented and resuspended in the manner for 2 additional times. The final cell preparation was further filtered through several layers of gauze before examining for viability using trypan blue. The cells were plated at a density of $2 \times 10^6$ cells per 60-mm Primaria plates (Falcon) pre-coated with collagen (Collaborative Research).

Cultures were incubated at 37° C. in 5% $CO_2$ for 3 hours to allow attachment and the medium was changed to a serum-free formulation and every 48 hrs thereafter. The serum-free formulation was a WME-based medium supplemented with growth factors, hormones, 10 mM HEPES (pH7.4), 100 ug/ml gentamycin, as has been described (Lanford).

B. Detection of Liver-Specific Proteins

Human hepatocyte cultures were maintained in serum-free medium for various period of time and labeled with [$^{35}$S]-methionine for 24 hrs. The medium was adjusted to contain 1 mM PMSF, 1 mM EDTA, and 1% NP40. Antibodies specific for the different plasma proteins were bound to protein A-agarose beads, the beads were washed with PBS, and aliquots of the labeled medium were incubated for 16 hrs at 4° C. with the antibody-bead complexes. The beads were washed 3 times with a buffer containing 1% NP40, and immunoprecipitated proteins were eluted with gel electrophoresis sample buffer containing 2% SDS and 2% 2-mercaptoethanol. Samples were analyzed by gradient SDS-PAGE (4 to 15%) and autoradiography.

EXAMPLE 2

In Vitro HEV Infection of Primary human Hepatocytes

A. HEV Infection of human hepatocytes

The HEV-infected cynomolgus monkey #73 stool pool (fourth passage) was used as an inoculum for infections of primary human hepatocytes. Various amounts of inoculum was diluted in 1 ml of serum-free medium (SFM) and applied to the culture during a 3 hr incubation period. This solution was then supplemented with 2 ml of fresh SFM and the entire mixture was incubated overnight. The next day, cell monolayers were washed with WME (10 mM HEPES, pH7.4) for three times and changed to fresh SFM, which was changed at two day intervals thereafter.

B. Immunofluorescence staining assay

Primary cynomolgus monkey hepatocytes were isolated and plated in tissue culture plates with collagen-coated coverslips as described. Cells on coverslips were infected with either the HEV-infected cynomolgus monkey #73 stool pool or the NIH normal human serum three days after initial plating. The infections were allowed to proceed for 2 weeks.

Cells on coverslips were fixed in 90% acetone at room temperature for 1 minute. The coverslips were then air-dried. The coverslips were blocked in 1% goat serum in PBS for 1 hour, washed with PBS for three times, and incubated with a mixture of rabbit antisera against HEV recombinant proteins 1L6, 4-2, and 6-1-4 at room temperature for 3 hours. The coverslips were again washed with PBS for 3 times and reacted with fluorescein isothiocyanate-conjugated (FITC) goat anti-rabbit IgG(H+L) (Zymed) diluted in PBS-1% goat serum for 30 minutes. After the coverslips were washed with PBS for 3 times and air-dried, they were mounted with FITC glycerol solution and examined under a fluorescent microscope.

C. Reverse transcription/polymerase chain reaction (RT/PCR)

HEV infection of primary cynomolgus macaque hepatocytes was evaluated by RT/PCR assays. The primers for cDNA synthesis and PCR were based on the nucleotide sequences of the full-length HEV cDNA (A. Tam et al.). Primers HEV3.2SF1 (nt 6578–6597) and HEV3.2SF2 (nt 6650–6668) are of sense polarity from the ORF2 region of the viral genome and HEV3.2SR1 (nt 7108–7127) and HEV3.2SR2 (nt 7078–7097) are antisense primers within the region.

Following extraction of total cellular RNA from HEV-infected cells using one-step guanidinium procedure or HEV-infected supernatants according to the method of Sherker et al., aliquots of RNA samples were heat-denatured at 95° C. for 5 minutes and subjected to reverse transcription at room temperature for 5 minutes and 42° C. for 60 minutes using 200 units per reaction of MMLV-reverse transcriptase (BRL) in a 20 ul reactin volume containing 20 units of RNasin (Promega), 1×PCR buffer (Perkin-Elmer Cetus), with a concentration of 1 mM each deoxyribonucleotide (Perkin-Elmer Cetus), and 2.5 uM of HEV3.2SR1 primer. The reaction mixture was then heat-treated at 95° C. for 5 minutes to denature the MMLV-reverse transcriptase.

Ten microliters of the cDNA synthesis product was used for PCR in a final volume of 50 ul with 0.5 uM HEV3.2SF1 primer, 1.25 units Taq DNA polymerase (AmpliTaq, Perkin-Elmer Cetus), and 1×PCR buffer, overlayed with 50 ul of mineral oil, and subjected to 40 cycles of PCR in a Perkin-Elmer thermocycler (95° C.×1 minute; 52° C.×2 minutes; 72° C.×30 seconds). Ten microliters of the first-round PCR product then underwent another 40 cycles of nested PCR (95° C.×1 minute; 55° C.×2 minutes; 72° C.×30 seconds) in a total volume of 50 ul containing the internal PCR primers HEV3.2SF2 and HEV3.2SR2.

First- and second-round PCR products were subjected to agarose electrophoresis, ethidium bromide stained and photographed under UV light. The results are shown in FIG. 4, discussed above. Southern transfer was performed and filters were hybridized with [$^{32}$P-dCTP]-labeled internal probe HEVORF2-7 exclusive of the primers (nt 6782–6997), and autoradiography performed.

EXAMPLE 3

Preparation of 406.3-2 and 406.4-2 Antigens

A TZKF1 plasmid (ET1.1), ATCC deposit number 67717, was digested with EcoRI to release the 1.33 kb HEV insert which was purified from the linearized plasmid by gel electrophoresis. The purified fragment was suspended in a standard digest buffer (0.5M Tris HCl, pH 7.5; 1 mg/ml BSA; 10 mM MnC12) to a concentration of about 1 mg/ml and digested with DNAse I at room temperature for about 5 minutes. These reaction conditions were determined from a prior calibration study, in which the incubation time required to produce predominantly 100–300 basepair fragments was determined. The material was extracted with phenol/chloroform before ethanol precipitation.

The fragments in the digest mixture were blunt-ended and ligated with EcoRI linkers. The resultant fragments were analyzed by electrophoresis (5–10 V/cm) on 1.2% agarose gel, using PhiX174/HaeIII and lambda/HindIII size markers. The 100–300 bp fraction was eluted onto NA45 strips (Schleicher and Schuell), which were then placed into 1.5 ml microtubes with eluting solution (1M NaCl, 50 mM arginine, pH 9.0), and incubated at 67° C. for 30–60 minutes. The eluted DNA was phenol/chloroform extracted and then precipitated with two volumes of ethanol. The pellet was resuspended in 20 ml TE (0.01M Tris HCl, pH 7.5, 0.001M EDTA).

B. Cloning in an Expression Vector

Lambda gt11 phage vector (Huynh) was obtained from Promega Biotec (Madison, Wisc.). This cloning vector has a unique EcoRI cloning site 53 base pairs upstream from the beta-galactosidase translation termination codon. The genomic fragments from above, provided either directly from coding sequences 5) or after amplification of cDNA, were introduced into the EcoRI site by mixing 0.5–1.0 mg EcoRI-cleaved gt11, 0.3–3 ml of the above sized fragments, 0.5 ml 10×ligation buffer (above), 0.5 ml ligase (200 units), and distilled water to 5 ml. The mixture was incubated overnight at 14° C., followed by in vitro packaging, according to standard methods (Maniatis, pp. 256–268).

The packaged phage were used to infect E. coli strain KM392, obtained from Dr. Kevin Moore, DNAX (Palo Alto, Calif.). Alternatively, E. Coli strain Y1090, available from the American Type Culture Collection (ATCC #37197), could be used. The infected bacteria were plated and the resultant colonies were checked for loss of beta-galactosidase activity-(clear plaques) in the presence of X-gal using a standard X-gal substrate plaque assay method (Maniatis). About 50% of the phage plaques showed loss of beta-galactosidase enzyme activity (recombinants).

C. Screening for HEV Recombinant Proteins

HEV convalescent antiserum was obtained from patients infected during documented HEV outbreaks in Mexico, Borneo, Pakistan, Somalia, and Burma. The sera were immunoreactive with VLPs in stool specimens from each of several other patients with ETNANB hepatitis.

A lawn of E coli KM392 cells infected with about 104 pfu of the phage stock from above was prepared on a 150 mm plate and incubated, inverted, for 5–8 hours at 37° C. The lawn was overlaid with a nitrocellulose sheet, causing transfer of expressed HEV recombinant protein from the plaques to the paper. The plate and filter were indexed for matching corresponding plate and filter positions.

The filter was washed twice in TBST buffer (10 mM Tris, pH 8.0, 150 mM NaCl, 0.05% Tween 20), blocked with AIB (TBST buffer with 1% gelatin), washed again in TBST, and incubated overnight after addition of antiserum (diluted to 1:50 in AIB, 12–15 ml/plate). The sheet was washed twice in TBST and then contacted with enzyme-labeled anti-human antibody to attach the labeled antibody at filter sites containing antigen recognized by the antiserum. After a final washing, the filter was developed in a substrate medium containing 33 ml NBT (50 mg/ml stock solution maintained at 4° C.) mixed with 16 ml BCIP (50 mg/ml stock solution maintained at 4° C.) in 5 ml of alkaline phosphatase buffer (100 mM Tris, 9.5, 100 mM NaCl, 5 mM MgC12). Purple color appeared at points of antigen production, as recognized by the antiserum.

D. Screening Plating

The areas of antigen production determined in the previous step were replated at about 100–200 pfu on an 82 mm plate. The above steps, beginning with a 5–8 hour incubation, through NBT-BCIP development, were repeated in order to plaque purify phage secreting an antigen capable of reacting with the HEV antibody. The identified plaques were picked and eluted in phage buffer (Maniatis, p. 443).

Two subclones which were selected are the 406.3-2 and 406.4-2 clones whose sequences are set forth above. These sequences were isolated from an amplified cDNA library derived from a Mexican stool. Using the techniques described in this section, polypeptides expressed by these clones have been tested for immunoreactivity against a number of different human HEV-positive sera obtained from sources around the world. As shown in Table 4 below, 8 sera immunoreactive with the polypeptide expressed by the 406.4-2, and 6 sera immunoreacted with polypeptide expressed by the 406.3-2 clone.

For comparison, the Table also shows reactivity of the various human sera with the non structural peptide Y2. Only one of the sera reacted with the polypeptide expressed by this clone. No immunoreactivity was seen for normal expression products of the gt11 vector.

TABLE 4

Immunoreactivity of HEV Recombinant Proteins: Human Sera

| Sera | Source | Stage[1] | 406.3-2 | 406.4-2 | Y2 | lgt11 |
|---|---|---|---|---|---|---|
| FVH-21 | Burma | A | − | − | − | − |
| FVH-8 | Burma | A | − | + | + | − |
| SOM-19 | Somalia | A | + | + | − | − |
| SOM-20 | Somalia | A | + | + | − | − |
| IM-35 | Borneo | A | + | + | − | − |
| IM-36 | Borneo | A | − | − | − | − |
| PAK-1 | Pakistan | A | + | + | − | − |
| FFI-4 | Mexico | A | + | + | − | − |
| FFI-125 | Mexico | A | − | + | − | − |
| F 387 IC | Mexico | C | + | + | ND | − |
| Normal | U.S.A. | − | − | − | − | − |

[1]A = acute; C = convalescent

Here Y2 represents a sequence encoded by the HEV sequence 157 basepair sequence from the first open reading frame of the HEV genome.

E. Producing the 406.3-2 Antigen

The 406.3-2 gt11 plasmid from above was digested with EcoRI and the released HEV fragment was amplified by PCR in the presence of linkers which added an NcoI site at the 5' fragment end, and a BamHI site at the 3' fragment end. The amplified material was digested with NcoI and BamHI and inserted into the NcoI/BamHI site of the glutathione S-transferase vector pGEX expression vector, according to the manufacturer's instructions.

The pGEX plasmid was used to transform E. coli host cells, and cells which were successfully transformed with the pGEX vector were identified by immunofluorescence, using anti-HEV human antisera.

F. Producing the 406.4-2 Antigen

The 406.4-2 gt11 plasmid from above was digested with EcoRI and the released HEV fragment was amplified by PCR, and the amplified fragment was inserted into the NcoI/BamHI site of the pGEX expression vector, as above. Peptide expression of the 406.4-2 peptide was similar to that described for the 406.3.2 fusion peptide.

G. Preparing Antibodies

The 406.3-2(M) and 406.4-2(M) fusion proteins, prepared as above, were used to immunize rabbits to generate HEV-specific antisera, according to standard procedures.

EXAMPLE 4

Neutralizing Activity of Anti-3.2(M) Antibody

A. In vitro Infection

To prove that primary human hepatocytes were permissive for HEV infection and replication, cells were exposed to either normal human serum (NIH normal human serum pool) or HEV-infected cynomolgus macaque stool preparation (cyno#73). Fourteen days postinfection, total cellular RNAs were prepared for reverse-transcription (RT)/polymerase chain reaction (PCR) assays to evaluate the infectability of primary human hepatocytes with HEV. The results indicated that primary human hepatocytes were capable of supporting HEV propagation (FIG. 4).

Although quantitative PCR was not applied, total cellular RNA isolated from HEV-infected primary human hepatocytes would indicate a high level of virus replication as suggested by the extent of hybridization with the a-$^{32}$P-dCTP labeled HEV-specific probe (lane 5). There was no evidence of HEV in total cellular RNA isolated from primary human hepatocytes treated with normal human serum pool (lane 4). As negative controls for RT/PCR assays, no carry-over or cross-contamination was detected (lanes 1, 2, and 3). The original HEV-infected cynomolgus macaque stool (cyno#73) was served as a positive control in the RT/PCR assays (lane 6).

B. Neutralizing Activity of Antibody

To examine the neutralizing activities of anti-3-2(M), -4-2-(M), each rabbit antiserum was used at a final dilution of 1:20 with the viral inoculum for HEV infection of primary human hepatocytes. The diluted antibody and viral inoculum were incubated together prior to infection of the cultured cells. Rabbit anti-3-2(M) exhibited a high level of neutralizing activity against HEV infection (FIG. 5, lane 2 versus lane 1). Very little neutralizing activity was observed in rabbit anti-4-2 (M) (lane 4 versus lane 3).

This result suggests that the HEV 3-2(M) but not HEV 4-2(M) or 4-2(B) recombinant protein encoded a neutralizing epitope capable of eliciting protective antibody or antibodies against HEV infection. The fact that the Mexico clone 3-2(M) and the Burma clone 3-2(B) share 90.5% homology at the amino acid level (79.8% at the nucleotide level) suggested that antibody(ies) raised against 3-2(M) should cross-neutralize or cross-protect HEV of Mexico or Burma strain from infecting permissive cells.

EXAMPLE 5

Vaccine Protection Against HEV

A. Preparation of trpE-C2 peptide

The pBET1 plasmid containing a 2.3 kb insert, corresponding to the 1.8 kb 3' end portion of HEV has been described (Tam). The plasmid was digested with EcoRI, releasing two HEV fragments having sizes of about 600 bp and 1400 bp of which 1210 bp contain coding sequence. The larger fragment was purified by electrophoresis and inserted into the EcoRI site of the pATH10 trpE fusion vector, obtained from T. J. Koerner et al. (Department of Microbiology, UCLA) The recombinant vector was used to transform $E.$ $coli$ DH5αF' host.

The recombinant typE-C2 fusion protein from pATH C2 was isolated by a modification of the procedure of Dieckmann et al. The bacterium containing the pATH C2 plasmid was grown overnight in growth media containing tryptophane. Two ml of the overnight culture was inoculated into 100 ml of fresh growth media and grown at 37° C. for an additional four hours. The bacterial broth was added to one liter of fresh growth media without tryptophane and allowed to grow at 30° C. for 1.5 hours. Ten ml indoleacrylic acid (1 mg/ml) was added and growth was continued for an additional 5 to 10 hours at 30° C. The bacterial cells were collected by centrifugation. The cell pellet was resuspended in a hypotonic solution containing lysozyme to degrade the bacterial cell wall. Sodium chloride and the detergent NP-40 were added to the suspension to cause hypertonic lysis of the cells. The lysed cell solution was sonicated. The solution was centrifuged. The resulting protein pellet was resuspended in about 5 ml of 10 mM Tris pH 7.5 using a dounce homogenizer. Approximately 75% of the protein in solution was composed of the trpE-C2 protein.

B. Preparation of Vaccine

Converted alum adjuvant was prepared according to standard methods. Briefly, a 10% alum suspension was titrated to pH 6.6 with 1N NaOH, then stirred overnight at 4° C. The suspension is clarified by low-speed centrifugation, and the supernatant decanted. A small amount of 0.9% NaCl+1:20,000 formalin was added to each pellet, and suspended by vortexing. To prepare an antigen vaccine composition, trpE-C2 fusion protein from above is added in a 0.9% NaCl solution to a desired final antigen concentration.

A non-adjuvanted insoluble trpE-C2 peptide was prepared as above in section A.

C. Vaccination

Six cynomolgus monkeys, designated 8901, 8902, 8903, 8910, 9902, and 9904, were used in the vaccination study. Four of the monkeys, 8901, and 8902 8903, and 8910 were immunized by intravenous injection with 1.0 ml of the alum adjuvanted trpE-C2 composition (containing about 50 μg of C2 peptide). The other two animals received adjuvant only. One month later the six animals were given a second vaccination, identical to the first.

4 weeks after the second vaccination, sera from the animals was tested for anti-HEV antibodies by Western blotting, using a fusionless C2 protein. At this stage, animals 8901 and 8902 each received a third vaccination with the non-adjuvanted, insoluble trpE-C2 composition (a total IV dose of about 80 μg trpE-C2 peptide each), and both animals showed anti-HEV by Western blotting 4 weeks later.

Animals 8901, 8903, and 9002 were each challenged IV with 1 ml each of a 10% third passage cyno stool (Burma strain) previously shown to be highly infectious. Animals 8902, 8910, and 9004 were each challenged IV with 1 ml of a proven infectious human stool isolate, Mexican #14, known to cause severe disease in cynos and moderate disease in chimpanzees. The results are shown in FIGS. 2A, 2B, and 3A, and 3B, discussed above.

EXAMPLE 6

HEV Epitopes Immunoreactive with Acute HEV Antisera

A. Synthesis of Overlapping Peptides

The method of Geysen et al (Geysen) was used in this synthesis. Briefly, decamers overlapping by every four amino acids were synthesized on polypropylene pin heads (Cambridge Research Biochemicals, Norwich, U.K.). All peptides were synthesized in duplicate. The amino acids used were pentafluorophenyl esters of 9-fluorenylmethoxycarbonyl derivatives. The blocks were immersed in dimethylformamide (DMF) (Baxter Healthcare, Burdick and Jackson Div., Muskegon, Mich.) for 5 min followed by deprotection in 20% piperidine in DMF for an hour. The blocks were then washed in 1% acetic acid (Mallinckrodt) in DMF for 5 min followed by a similar wash in DMF. After four washes in methanol, the blocks were air-dried for an hour.

Prior to the addition of amino acids at a concentration of 30 mM, the blocks were allowed to sit in DMF for 5 min. The amino acid derivatives were dissolved in an equimolar solution of 1-hydroxybenzotriazole (Sigma) in DMF. One hundred microliters of the desired amino acids was dispensed into appropriate wells of polypropylene microtiter plates, which were then incubated overnight at room temperature.

The following day, after the blocks were washed once in DMF and four times in methanol and air-dried as previously, deprotection was performed. The above steps were repeated until the desired number of amino acids had been added. The N-terminal amino group was then acetylated in DMF containing 10% acetic anhydride (Sigma) and 2% diisopropylethylamine (Sigma). After an incubation of 90 min at room temperature, the peptides were deblocked for 4 hr in trifluoroadetic acid (Sigma) containing 2.5% phenol (Sigma) and 2.4% 1,2-ethanedithiol (Sigma). This was followed by washes in dichloromethane (Aldrich) and in dichloromethane containing 5% diisopropylethylamine. The blocks were then air-dried and rinsed in distilled water and in methanol (Mallinckrodt). After air-drying, the blocks were stored in silica gel for at least 17 hr at room temperature prior to storage at −20° C. To monitor the synthesis, peptides with amino acid sequences PLAQ and GLAQ were simultaneously synthesized on control pins.

B. Human Sera

Serum samples from 11 Sudanese pediatric patients (14 years of age or less) with acute hepatitis E diagnosed by a Western blot assay (Hyams) were pooled and tested and reactivity to the overlapping peptides described above. Serum samples from 11 control patients in the same study (Hyams) with no evidence of acute hepatitis E (as determined by Western blot assay) were also pooled and served as a negative control.

C. Testing of Human Sera by ELISA

The blocks were allowed to reach ambient temperature before incubation for one hour at 37° C. in blocking reagent [5% bovine serum albumin (Calbiochem), 0.05% Tween 20 (Sigma), and 0.05% sodium azide (Fischer Scientific)] in phosphate-buffered saline (PBS, pH 7.2, GIBCO). The blocks were incubated overnight with the appropriate serum sample (1:100 dilution in blocking reagent) or with PBS at 4° C. All pooled sera were tested against the duplicate syntheses. The PLAQ and GLAQ pins were tested with commercially available murine sera (Cambridge Research Biochemicals).

The following day the blocks were washed four times in PBS (pH 7.2) containing 0.05% Tween 20 and 0.5% sodium azide (wash buffer) and incubated for an hour at 37° C. with alkaline phosphatase labeled goat anti-human IgG+IgM at a 1:1000 dilution in the wash buffer. The PLAQ and GLAQ pins received a similarly labeled goat anti-mouse IgG at a 1:1000 dilution. The blocks were once again washed as described earlier and the color was developed by using a commercially available phosphatase substrate kit (Kirkegaard and Perry Laboratories, Gaithersburg, Md.). The intensity of the color reaction was determined on the UV max (Molecular Devices) at 405 nm. The readings obtained for peptides incubated with PBS were then deducted from the corresponding readings obtained with the serum samples.

D. Sonication of Blocks

After use, the blocks were washed in PBS for 5 min prior to sonication at 47 kHz and 60° C. in sodium phosphate buffer containing it SDS (Sigma) and 0.1% 2-mercaptoethanol (Sigma) for 40 min. Sonication was followed by four washed in water and one wash in methanol at 60° C. The blocks were then air-dried for an hour prior to storage at −20° C.

While the invention has been described with reference to particular embodiments, methods, construction and use, it will be apparent to those skilled in the art that various changes and modifications can be made without departing from the invention.

It is claimed:

1. A hepatitis E virus (HEV) peptide selected from the group consisting of SEQ ID NOs:23–38.

2. The peptide of claim 1, which is selected from the group consisting of SEQ ID NOs:23–34.

3. The peptide of claim 1, which is selected from the group consisting of SEQ ID NOs:35–37.

4. The peptide of claim 1, which has the sequence SEQ ID NO:38.

5. A diagnostic reagent comprising a solid support, and derivatized thereto, a hepatitis E virus (HEV) peptide antigen selected from the group consisting of SEQ ID NOs:23–38.

6. The reagent of claim 5, which is selected from the group consisting of SEQ ID NOs:23–34.

7. The reagent of claim 5, which is selected from the group consisting of SEQ ID NOs:35–37.

8. The reagent of claim 5, which has the sequence SEQ ID NO:38.

* * * * *

UNITED STATES PATENT AND TRADEMARK OFFICE
CERTIFICATE OF CORRECTION

PATENT NO : 5,885,768
DATED : March 23, 1999
INVENTOR(S): Reyes et al.

It is certified that error appears in the above-identified patent and that said Letters Patent are hereby corrected as shown below:

On the first page of the patent, at number 73, insert

GeneLabs Technologies, Inc., Redwood City, California.

Signed and Sealed this

Twenty-ninth Day of May, 2001

Attest:

NICHOLAS P. GODICI

Attesting Officer

Acting Director of the United States Patent and Trademark Office